(12) United States Patent
Wedekind et al.

(10) Patent No.: US 8,158,770 B2
(45) Date of Patent: Apr. 17, 2012

(54) CONTENT DEPENDENT INHIBITORS OF CYTIDINE DEAMINASES AND USES THEREOF

(75) Inventors: Joseph E. Wedekind, Rochester, NY (US); Harold C. Smith, Rochester, NY (US)

(73) Assignee: University of Rochester, Rochester, NY (US)

(*) Notice: Subject to any disclaimer, the term of this patent is extended or adjusted under 35 U.S.C. 154(b) by 809 days.

(21) Appl. No.: 11/579,660

(22) PCT Filed: May 6, 2005

(86) PCT No.: PCT/US2005/016001
§ 371 (c)(1),
(2), (4) Date: Oct. 15, 2008

(87) PCT Pub. No.: WO2005/115410
PCT Pub. Date: Dec. 8, 2005

(65) Prior Publication Data
US 2009/0099105 A1    Apr. 16, 2009

Related U.S. Application Data

(60) Provisional application No. 60/568,490, filed on May 6, 2004.

(51) Int. Cl.
C07H 21/04    (2006.01)
(52) U.S. Cl. ...................... 536/24.1; 536/22.1; 536/23.1
(58) Field of Classification Search ........................ None
See application file for complete search history.

(56) References Cited

U.S. PATENT DOCUMENTS

| | | | |
|---|---|---|---|
| 5,468,022 | A | 11/1995 | Linder et al. |
| 5,747,319 | A | 5/1998 | Au-Young |
| 5,804,185 | A | 9/1998 | Bandman |
| 5,866,333 | A | 2/1999 | Innerarity et al. |
| 5,916,556 | A | 6/1999 | Au-Young et al. |
| 6,041,253 | A | 3/2000 | Kost et al. |
| 6,087,108 | A | 7/2000 | Bandman et al. |
| 6,331,311 | B1 | 12/2001 | Brodbeck et al. |
| 6,653,443 | B2 | 11/2003 | Zhang |
| 6,942,967 | B1 | 9/2005 | Harosh |
| 2003/0013844 | A1 | 1/2003 | Zhang et al. |
| 2004/0115184 | A1 | 6/2004 | Smith et al. |
| 2004/0234956 | A1 | 11/2004 | Kabat et al. |
| 2005/0112555 | A1 | 5/2005 | Smith et al. |
| 2005/0287648 | A1 | 12/2005 | Smith et al. |

FOREIGN PATENT DOCUMENTS

| | | |
|---|---|---|
| CH | 502 546 | 1/1971 |
| EP | 0 568 510 | 11/1993 |
| EP | 0 789 206 | 8/1997 |
| EP | 1 392 846 | 11/2008 |
| WO | WO 95/05851 | 3/1995 |
| WO | WO 02/68676 | 2/2002 |
| WO | WO 2005/024422 | 3/2005 |
| WO | WO 2005/047476 | 5/2005 |
| WO | WO 2005/118817 | 12/2005 |

OTHER PUBLICATIONS

Frick et al. Biochemistry (1989), vol. 28, pp. 9423-9430.*
Zhou et al. J. Mol. Biol. (2002), vol. 321, pp. 591-599.*
Abad et al. Single-step, multiple retroviral transduction of human T cells. *J Gene Med* 4: 27-37 (2002).
Anant et al. ARCD-1, an apobec-1-related cytidine deaminase, exerts a dominant negative effect on C to U RNA editing. *Am J Physiol Cell Physiol*. 281:C1904-16 (2001).
Anant et al., APOBEC-1, the catalytic subunit of the mammalian apoB B mRNA editing enzyme, is a novel RNA-binding protein. *J. Biol. Chem*. 270:14762-14767 (1995).
Anant et al., AU-rich RNA binding proteins Hel-N1 and AUF1 bind apolipoprotein B mRNA and inhibit posttranscriptional C to U editing. *Nucleic Acids Symp. Ser*. 36, 115-118 (1997).
Anant et al., Molecular mechanisms of apolipoportein B mRNA editing *Curr Opin Lipidol*. 12(2): 159-165 (2001).
Ashley et al., Inhibition of *Escherichia coli* cytidine deaminase by a phosphapyrimidine nucleoside, *Journal of Biological Chemistry*, 1984, vol. 259, pp. 13621-13627.
Bachl and Wabl, Enhancers of hypermutation. *Immunogenet*. 45: 59-64 (1996).
Bachl et al., Increased transcription levels induce higher mutation rates in a hypermutating cell line. *J Immunol* 166:5051-5057 (2001).
Backus and Smith, Apolipoprotein B mRNA sequences 3' of the editing site are necessary and sufficient for editing and editosome assembly. Nucleic Acids Res. 19:6781-6786 (1991).
Backus and Smith, Specific 3' sequences flanking a minimal apoB mRNA editing 'cassette' are critical for efficient editing in vitro. *Biochim. Biophys. Acta* 1217, 65-73 (1994).
Backus and Smith, Three distinct RNA sequence elements are required for efficient apoB RNA editing in vitro. *Nucleic Acids Res*. 22, 6007-6014 (1992).
Backus and, Only cytidines 5' of the apoB mRNA mooring sequence are edited. *Biochim. Biophys. Acta* 1219:1-14 (1994).
Backus JW, Eagleton MJ, Harris SG, Sparks CE, Sparks JD, Smith HC. Quantitation of endogenous liver apolipoprotein B mRNA editing. *Biochem Biophys Res Commun*. Jul. 31, 1990;170(2):513-8.
Barchi et al. The decomposition of 1-(.beta.-D-ribofuranosyl)-1,2-dihydropyrimidin-2-one (zebularine) in alkali: mechanism and products. J. Org. Chem.; 1992; 57(2) pp. 536-541.
Barchi et al., Improved synthesis of zebularine [1-(beta-D-ribofuranosyl)-dihydropyrimidin-2-one] nucleotides as inhibitors of human deoxycytidylate deaminase. *J Enzyme Inhib* 9:147-162 (1995).
Berkhout et al., HIV-1 RNA editing, hypermutation, and error-prone reverse transcription. *Science* 292(5514):7 (2001).
Bernstein et al., The rest is silence. *RNA*. Nov. 2001;7(11):1509-1521.
Bishop et al., Cytidine deamination of retroviral DNA by divers APOBEC proteins. *Curr Biol*. Aug. 10, 2004;14(15): 1392-1396.

(Continued)

*Primary Examiner* — Patrick Lewis
(74) *Attorney, Agent, or Firm* — Riverside Law LLP

(57) ABSTRACT

This invention relates to cytidine deaminase inhibitors (Cytidine deaminase inhibitors) of cytidine deaminases and uses thereof.

24 Claims, 9 Drawing Sheets

OTHER PUBLICATIONS

Blanc, V., et al. Mutagenesis of apobec-1 complementation factor reveals distinct domains that modulate RNA binding, protein-protein interaction with apobec-1, and complementation of C to U RNA-editing activity. *J Biol Chem.* 276:46386-46393 (2001).

Bogerd et al. A single amino acid difference in the host APOBEC3G protein controls the primate species specificity of HIV type 1 virion infectivity factor. *Proc Natl Acad Sci USA.* Mar. 16, 2004;101(11):3770-3774. Epub Mar 3, 2004.

Bourara et al., Generation of G-to-A and C-to-U changes in HIV-1 transcripts by RNA editing. *Science.* 289(5484);1564-1566 (2000).

Bross et al., DNA Double-Strand Breaks: Prior to but not Sufficient in Targeting Hypermutation. *J Exp Med.* 195(9):1187-1192 (2002).

Carlow et al., Role of glutamate-104 in generating a transition state analogue inhibitor at the active site of cytidine daeminase, *Biochemistry,* 1996, vol. 35, pp. 948-954.

Chan et al. RNA Editing. *Scientific American Science & Medicine.* pp. 68-77 (Mar./Apr. 1995).

Chen et al., Roles of uracil-DNA glycosylase and dUTPase in virus replication. *J Gen Virol.* 83(Pt 10): 2339-2345 (2002).

Cheng JC, Matsen CB, Gonzales FA, Ye W, Greer S, Marquez VE, Jones PA, Selker EU. Inhibition of DNA methylation and reactivation of silenced genes by zebularine. *J Natl Cancer Inst.* Mar. 5, 2003;95(5):399-409.

Cho et al., Requirement of dimerization for RNA editing activity of adenosine deaminases acting on RNA. *J Biol Chem* 278: 17093-17102 (2003).

Dance et al., APOBEC-1 dependent cytidine to uridine editing of apolipoprotein B RNA in yeast. *Nucleic Acids Res.* 28, 424-429 (2000).

Dance et al., Identification of the yeast cytidine deaminase CDD1 as an orphan C to U RNA editase. *Nucleic Acids Res.* 29,1772-1780 (2001).

Dance et al., Two proteins essential for apolipoprotein B mRNA editing are expressed from a single gene through alternative splicing. *J. Biol. Chem.* 277:12703-09 (2002).

Driscoll et al., Antitumor properties of 2(1H)-pyrimidinone riboside (zebularine) and its fluorinated analogues. *J Med Chem* 34:3280-3284 (1991).

Eliopoulos N, Cournoyer D, Momparler RL. Drug resistance to 5-aza-2'-deoxycytidine, 2',2'-difluorodeoxycytidine, and cytosine arabinoside conferred by retroviral-mediated transfer of human cytidine deaminase cDNA into murine cells. *Cancer Chemother Pharmacol.* 1998;42(5):373-8.

Frick et al., Binding of pyrimidin-2-one ribonucleoside by cytidine deaminase as the transition-state analogue 3,4-dihydrouridine and the contribution of the 4-hydroxyl group to its binding affinity. *Biochemistry* 28:9423-9430 (1989).

Gerber et al., An adenosine deaminase that generates inosine at the wobble position of tRNAs. *Science* 286(5442): 1146-1149 (1999).

Gott and Emeson, Functions and mechanisms of RNA editing. *Annu. Rev. Genet.* 34:499-531 (2000).

Gulick AM, Bauer CB, Thoden JB, Pate E, Yount RG, Rayment I. X-ray structures of the *Dictyostelium discoideum* myosin motor domain with six non-nucleotide analogs. *J Biol Chem.* Jan. 7, 2000;275(1):398-408.

Harris et al., RNA editing enzyme APOBEC1 and some of its homologs can act as DNA mutator. *Mol. Cell* 10(5): 1247-1253 (2002).

Henzler et al., Fully functional, naturally occurring and C-terminally truncated variant human immunodeficiency virus (HIV) Vif does not bind to HIV Gag but influences intermediate filament structure *J Gen Virol.* Mar. 2001;82(Pt 3):561-573.

Hersberger and Innerarity, Two efficiency elements flanking the editing site of cytidine 6666 in the apolipoprotein B mRNA support mooring dependent editing. *J. Biol. Chem.* 273, 9435-9442 (1998).

Hersberger et al., Phylogenetic analysis of the apolipoprotein B mRNA editing region. Evidence for a secondary structure between the mooring sequence and the 3' efficiency element. *J. Biol. Chem.* 274, 34590-34597 (1999).

Hughes et al. Gene Transfer of Cytidine Deaminase apoBEC-1 Lowers Lipoprotein(a) in Transgenic Mice and Induces Apolipoprotein B mRNA Editing in Rabbits. *Hum. Gene Ther.* 7:39-49 (Jan. 1, 1996).

Hung ML, Chao P, Chang KY. dsRBM1 and a proline-rich domain of RNA helicase A can form a composite binder to recognize a specific dsDNA. *Nucleic Acids Res.* Oct. 1, 2003;31(19):5741-53.

Itakura et al., Synthesis and use of synthetic oligonucleotides. *Annu Rev Biochem.* 1984;53:323-56.

Jayan GC, Casey JL. Inhibition of hepatitis delta virus RNA editing by short inhibitory RNA-mediated knockdown of ADAR1 but not ADAR2 expression. *J Virol.* Dec. 2002;76(23):12399-404.

Jeong et al., Carbocyclic analogues of the potent cytidine deaminase inhibitor 1-(b-D-ribofuranosyl)-1, 2-dihydropyrimidin-2-one (Zebularine), *J. Med. Chem.,* 1998, vol. 41, pp. 2572-2578.

Kim CH, Marquez VE, Mao DT, Haines DR, McCormack JJ. Synthesis of pyrimidin-2-one nucleosides as acid-stable inhibitors of cytidine deaminase. *J Med Chem.* Aug. 1986;29(8):1374-80.

Laliberte J, Marquez VE, Momparler RL. Potent inhibitors for the deamination of cytosine arabinoside and 5-aza-2'-deoxycytidine by human cytidine deaminase. *Cancer Chemother Pharmacol.* 1992;30(1):7-11.

Lehmann KA, Bass BL. The importance of internal loops within RNA substrates of ADAR1. *J Mol Biol.* Aug. 6, 1999;291(1):1-13.

Liu B, Yu X, Luo K, Yu Y, Yu XF. Influence of primate lentiviral Vif and proteasome inhibitors on human immunodeficiency virus type 1 virion packaging of APOBEC3G. J Virol. Feb. 2004;78(4):2072-81.

Maas and Rich, Changing genetic information through RNA editing. *BioEssays* 22, 790-802 (2000).

MacGinnitie et al., Mutagenesis of apobec-1, the catalytic subunit of the mammalian apolipoprotein B mRNA editing enzyme, reveals distinct domains that mediate cytosine nucleoside deaminase, RNA binding, and RNA editing activity. *J Biol Chem.* Jun. 16, 1995;270(24):14768-14775.

Mehta and Driscoll, Identification of domains in apobec-1 complementation factor required for RNA binding and apolipoprotein-B mRNA editing. *RNA.* Jan. 2002;8(1):69-82.

Mehta et al., Molecular cloning of apobec-1 complementation factor, a novel RNA-binding protein involved in the editing of apolipoprotein B mRNA. *Mol Cell Biol.* Mar. 2000;20(5):1846-1854.

Nakamuta et al., Complete phenotypic characterization of apobec-1 knockout mice with a wild-type genetic background and a human apoB transgenic background, and restoration of apoB mRNA editing by somatic gene transfer of APOBEC-1. *J. Biol. Chem.* 271:25981-25988 (1996).

Navaratnam et al., Apolipoprotein B mRNA editing is associated with UV crosslinking of proteins to the editing site. *Proc Natl Acad Sci U S A.* 90(1): 222-226 (1993).

Paddison et al., Short hairpin RNAs (shRNAs) induce sequence-specific silencing in mammalian cells. *Genes Dev.* 16(8):948-958 (2002).

Petersen-Mahrt and Neuberger, 2003. In vitro deamination of cytosine to uracil in single-stranded DNA by APOBEC1. *J. Biol. Chem.* in press (2003).

Renda et al., Mutation of the methylated tRNA(Lys)(3) residue A58 disrupts reverse transcription and inhibits replication of human immunodeficiency virus type 1. *J Virol* 75(20):9671-8 (2001).

Richardson et al., Secondary structure for the apolipoprotein B mRNA editing site. AU binding proteins interact with a stem loop. *J. Biol Chem.* 1998;273:31707-31717.

Rueter et al. Regulation of alternative splicing by RNA editing. *Nature.* 399(6731):75-80 (1999).

Rueter et al., Adenosine-to-inosine conversion in mRNA. In Modification and Editing of RNA (Grosjean, H. and Benne, R., eds.), pp. 343-361, *American Society for Microbiology Press*, Washington. (1998).

Schwarze et al. In Vivo Protein Transduction: Delivery of a Biologically Active Protein into the Mouse. *Science.* 285:1569-1572 (Sep. 3, 1999).

Schwarze et al. In vivo protein transduction: intracellular delivery of biologically active proteins, compounds, and DNA. *TiPS.* 21:45-48 (Feb. 2000).

Schwarze et al. Protein transduction: unrestricted delivery into all cells. *Trends Cell Biol.* 10:290-295 (Jul. 2000).

Shah et al., Sequence requirements for the editing of apolipoprotein B mRNA. *J. Biol. Chem.* 1991;266:16301-16304.

Smith and Sowden, Base modification RNA editing. *Trends in Genetics* 1996;12:418-424.

Smith et al., A guide to RNA editing. *RNA* 1997;3:1105-1123.

Smith et al., In vitro Apolipoprotein B mRNA editing: identification of a 27 S editing complex. *Proc. Natl. Acad. Sci. U.S.A.* 1991;88:1489-1493.

Smith, Analysis of protein complexes assembled on apolipoprotein B mRNA for mooring sequence-dependent RNA editing. *Methods*. May 1998;15(1):27-39.

Smith, Apo B mRNA editing: the sequence to the event. Seminars in Cell Biology (Stuart, K., ed.) Saunders Sci. Publications/Academic Press, London, 4, 267-278 (1993).

Sova et al., Efficiency of viral DNA synthesis during infection of permissive and nonpermissive cells with vif-negative human immunodeficiency virus type 1. *J Virol*. 67(10): 6322-6 (1993).

Sowden and Smith, Commitment of apolipoprotein B RNA to the splicing pathway regulates cytidine-to-uridine editing-site utilization. *Biochem J* 2001;359(Pt 3):697-705.

Sowden et al., ApoB RNA sequence 3' of the mooring sequence and cellular sources of auxiliary factors determine the location and extent of promiscuous editing. *Nucleic Acids Res*. 26, 1644-1652 (1998).

Sowden et al., Determinants involved in regulating the proportion of edited apolipoprotein B RNAs. *RNA* 1996;2:274-288.

Sowden et al., Multiple cooperative interactions constrain BPV-1 E2 dependent activation of transcription. *Nucleic Acids Res*. 1989;17:2959-2972.

Sowden et al., Over-expression of APOBEC-I results in mooring sequence dependent promiscuous RNA editing. J. Biol. Chem. 1996;271:3011-3017.

Sowden et al., The editosome for cytidine to uridine mRNA editing has a native complexity of 27S: identification of intracellular domains containing active and inactive editing factors. *J. Cell Science* 2002;115:1027-1039.

Veliz EA, Easterwood LM, Beal PA. Substrate analogues for an RNA-editing adenosine deaminase: mechanistic investigation and inhibitor design. *J Am Chem Soc*. Sep. 10, 2003;125(36):10867-76.

Wedekind and McKay, Purification, crystallization, and X-ray diffraction analysis of small ribozymes. *Methods Enzymol* 2000;317:149-168.

Wedekind et al., Messenger RNA editing in mammals: new members of the APOBEC family seeking roles in the family business. *Trends Genet*. 2003;19:207-216.

Xiang S, Short SA, Wolfenden R, Carter CW Jr. Cytidine deaminase complexed to 3-deazacytidine: a "valence buffer" in zinc enzyme catalysis. *Biochemistry*. Feb. 6, 1996;35(5):1335-41.

Xiang S, Short SA, Wolfenden R, Carter CW Jr. The structure of the cytidine deaminase-product complex provides evidence for efficient proton transfer and ground-state destabilization. *Biochemistry*. Apr. 22, 1997;36(16):4768-74.

Xiang S, Short SA, Wolfenden R, Carter CW Jr. Transition-state selectivity for a single hydroxyl group during catalysis by cytidine deaminase. *Biochemistry*. Apr. 11, 1995;34(14):4516-23.

Xie et al. "The structure of a yeast RNA-editing deaminase provides insight into the fold and function of activation-induced deaminase and APOBEC-1," PNAS 1(21):8114-8119, May 25, 2004.

Xu, Y and Kool, ET. A novel 5'-iodonucleoside allows efficient nonenzymatic ligation of single-stranded and duplex DNAs. Tetrahedron Lett., 1997, 38:5595-5598.

Yang and Smith, In vitro reconstitution of apolipoprotein B RNA editing activity from recombinant APOBEC-1 and McArdle cell extracts. *Biochem. Biophys. Res. Commun*. 1996;218:797-801.

Yang et al., Apolipoprotein B mRNA editing and the Reduction in Synthesis and secretion of the atherogenic risk factor apoB100 is reduced through TAT-mediated protein transduction of an mRNA editase into hepatocytes. Molec. Pharm. 61:269-276 (2002).

Yang et al., Induction of cytidine to uridine editing on cytoplasmic apolipoprotein B mRNA by overexpressing APOBEC-1. *J. Biol. Chem*. 2000;275, 22663-22669.

Yang et al., Intracellular trafficking Determinants in APOBEC-1, the Catalytic Subunit for Cytidine to Uridine Editing of Apolipoprotein B mRNA. Exp. *Cell Res*. 2001;267:153-164.

Yang et al., Multiple protein domains determine the cell type-specific nuclear distribution of the catalytic subunit required for apolipoprotein B mRNA editing. *Proc. Natl. Acad. Sci. U.S.A.* 1997;94:13075-13080.

Yang et al., Partial characterization of the auxiliary factors involved in apoB mRNA editing through APOBEC-1 affinity chromatography, *J Biol. Chem*., 1997;272:27700-27706.

Yang et al., Potent Suppression of Viral Infectivity by the Peptides That Inhibit Multimerization of Human Immunodeficiency virus Type 1 (HIV-1) Vif Proteins. *J. Biol Chem*. 2003;278(8):6596-6602.

Yi-Brunozzi HY, Easterwood LM, Kamilar GM, Beal PA. Synthetic substrate analogs for the RNA-editing adenosine deaminase ADAR-2. *Nucleic Acids Res*. Jul. 15, 1999;27(14):2912-7.

Yu et al. Single-strand specificity of APOBEC3G accounts for minus-strand deamination of the HIV genome. *Nat Struct Mol Biol*. 11(5):435-442 (2004).

Zhang H, Yang B, Pomerantz RJ, Zhang C, Arunachalam SC, Gao L. The cytidine deaminase CEM15 induces hypermutation in newly synthesized HIV-1 DNA. Nature. Jul. 3, 2003;424(6944):94-8.

Zhou et al., Zebularine: a novel DNA methylation inhibitor that forms a covalent complex with DNA methyltransferases. *J Mol Biol* 2002;321:591-599.

03767199.7, Smith, Aug. 5, 2003, Supplementary Partial European Search Report, Jan. 23, 2007.

03767199.7, Smith, Aug. 5, 2003, Supplementary Partial European Search Report, Nov. 3, 2006.

03767199.7, Smith, Aug. 5, 2003, Amendment to Claims, Mar. 15, 2006.

2003257181, Smith, Feb. 7, 2005, Examination Report, Sep. 24, 2007.

U.S. Appl. No. 10/934,090, filed Sep. 3, 2004, Smith, Final Rejection, May 30, 2008.

U.S. Appl. No. 10/934,090, filed Sep. 3, 2004, Smith, Final Rejection, Sep. 11, 2007.

U.S. Appl. No. 10/934,090, filed Sep. 3, 2004, Smith, Non-Final Rejection, Dec. 15, 2006.

U.S. Appl. No. 10/934,090, filed Sep. 3, 2004, Smith, Response to Election/Restriction, Nov. 6, 2006.

U.S. Appl. No. 10/934,090, filed Sep. 3, 2004, Smith, Restriction Requirement/Election, Oct. 5, 2006.

PCT/US04/28796, Smith, Sep. 3, 2004, International Preliminary Report on Patentability, Jul. 24, 2006.

PCT/US04/28796, Smith, Sep. 3, 2004, International Search Report, Jun. 29, 2006.

PCT/US04/28796, Smith, Sep. 3, 2004, Written Opinion, Jun. 26, 2006.

04788573.6, Smith, Mar. 30, 2006, Examination Report, Feb. 4, 2008.

04788573.6, Smith, Mar. 30, 2006, Supplementary Partial European Search Report, Oct. 12, 2007.

04788573.6, Smith, Mar. 30, 2006, Supplementary Partial European Search Report, Jul. 19, 2007.

04788573.6, Smith, Mar. 30, 2006, Amendment to Claims, Sep. 21, 2006.

PCT/US04/28796, Smith, Sep. 3, 2004, International Search Report, May 2, 2008.

PCT/US04/28796, Smith, Sep. 3, 2004, Written Opinion, May 2, 2008.

U.S. Appl. No. 10/468,987, filed Jan. 9, 2004, Smith, Response to Final Rejection, Jul. 17, 2008.

U.S. Appl. No. 10/468,987, filed Jan. 9, 2004, Smith, Final Rejection, Mar. 31, 2008.

U.S. Appl. No. 10/468,987, filed Jan. 9, 2004, Smith, Response to Office Action, Jul. 17, 2007.

U.S. Appl. No. 10/468,987, filed Jan. 9, 2004, Smith, Office Action, Aug. 22, 2007.

U.S. Appl. No. 10/468,987, filed Jan. 9, 2004, Smith, Response to Final Rejection, May 29, 2007.

U.S. Appl. No. 10/468,987, filed Jan. 9, 2004, Smith, Final Rejection, Nov. 29, 2006.

U.S. Appl. No. 10/468,987, filed Jan. 9, 2004, Smith, Response to Office Action, Jan. 29, 2004.

U.S. Appl. No. 10/468,987, filed Jan. 9, 2004, Smith, Office Action, Mar. 20, 2006.
U.S. Appl. No. 10/468,987, filed Jan. 9, 2004, Smith, Response to Restriction Requirement, Feb. 23, 2006.
U.S. Appl. No. 10/468,987, filed Jan. 9, 2004, Smith, Election/Restriction, Dec. 23, 2005.
PCT/US02/05824, Smith, Feb. 26, 2002, International Preliminary Report on Patentability, Mar. 21, 2004.
PCT/US02/05824, Smith, Feb. 26, 2002, International Search Report, Oct. 27, 2003.
2439472, Smith, Aug. 27, 2003, Office Action, Sep. 5, 2007.
02731102.6, Smith, Feb. 26, 2002, Decision to Grant, May 16, 2008.
02731102.6, Smith, Feb. 26, 2002, Intention to Grant, Dec. 21, 2007.
02731102.6, Smith, Feb. 26, 2002, Response to Examination, Mar. 27, 2007.
02731102.6, Smith, Feb. 26, 2002, Examination Report, Nov. 27, 2006.
02731102.6, Smith, Feb. 26, 2002, Response to Examination, Sep. 22, 2006.
02731102.6, Smith, Feb. 26, 2002, Examination Report, Mar. 21, 2006.
02731102.6, Smith, Feb. 26, 2002, Supplementary European Search Report, Aug. 4, 2005.
U.S. Appl. No. 10/523,038, filed Feb. 2, 2005, Smith, Response to Office Action, Jul. 15, 2008.
U.S. Appl. No. 10/523,038, filed Feb. 2, 2005, Smith, Office Action, Feb. 15, 2008.
U.S. Appl. No. 10/523,038, filed Feb. 2, 2005, Smith, Response to Office Action, Dec. 3, 2007.
U.S. Appl. No. 10/523,038, filed Feb. 2, 2005, Smith, Office Action, Oct. 1, 2007.
PCT/US03/24458, Smith, Aug. 5, 2003, International Search Report, Nov. 18, 2005.
03767199.7, Smith, Aug. 5, 2003, Examiner Report, Jul. 16, 2008.
03767199.7, Smith, Aug. 5, 2003, Amendment to Claims, Nov. 27, 2007.
03767199.7, Smith, Aug. 5, 2003, Examiner Report, May 31, 2007.

* cited by examiner

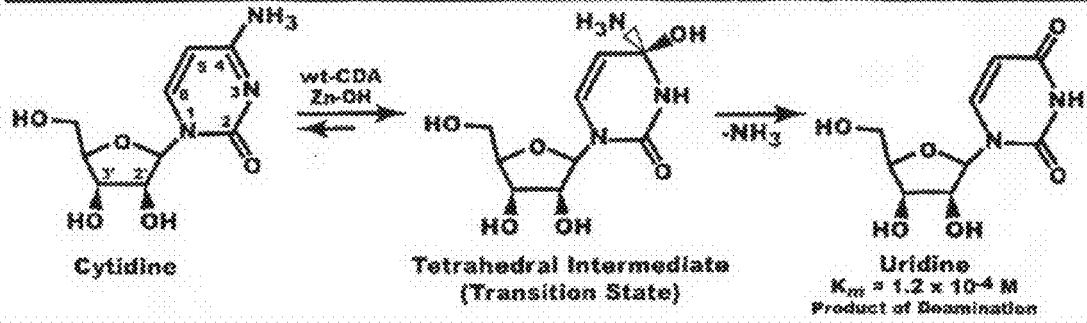
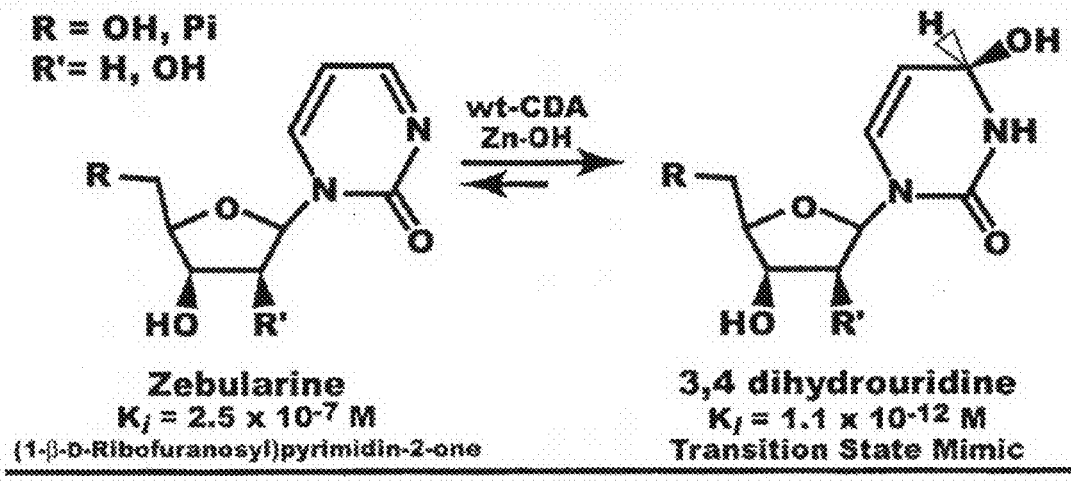
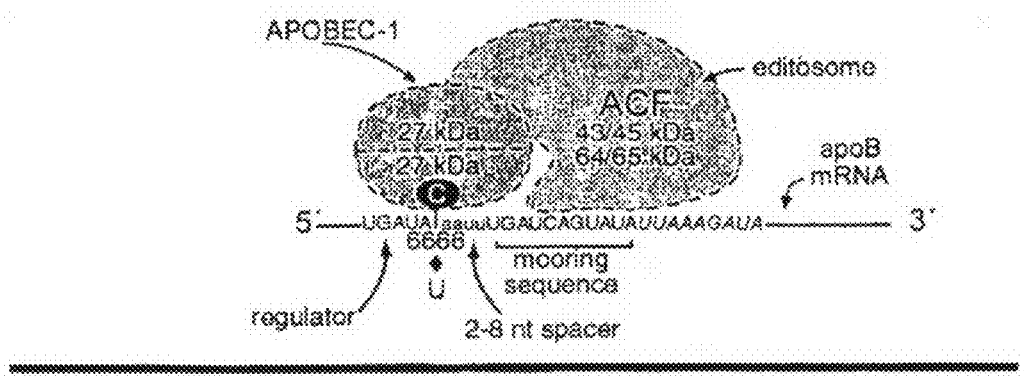

Figure 4: Zebularine Mimics for CDA Inhibition

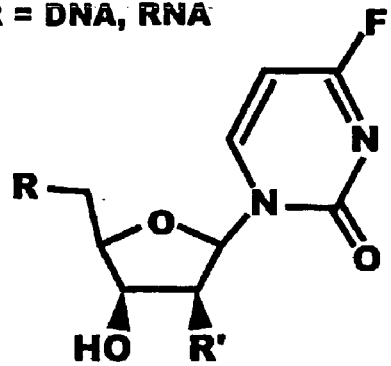

4-Fluoro Zebularine

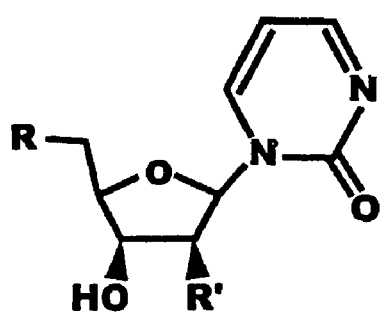

2'-deoxy, 2'-Fluoro Zebularine

Figure 5: Context Dependent Inhibition single stranded (ss) DNA or RNA* double stranded DNA or RNA* double stranded DNA or RNA* with ss 'replication' bubble

*Flanking RNA or DNA could be made more stable [resistant to chemical or enzymatic (nuclease) degradation] by use of phosphorothioate strands, 2'-OMe, 2'-F, or 2'-NH$_3$ substitution incorporated at the level of chemical synthesis.

Figure 6.
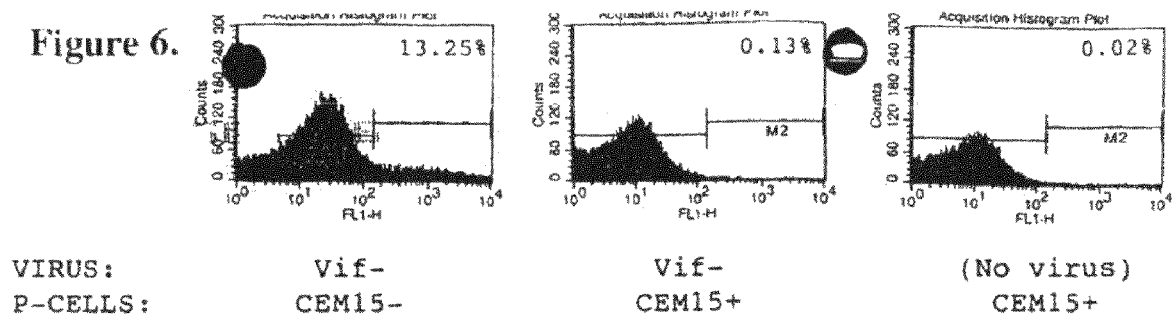
VIRUS:        Vif−         Vif−        (No virus)
P-CELLS:    CEM15−      CEM15+       CEM15+
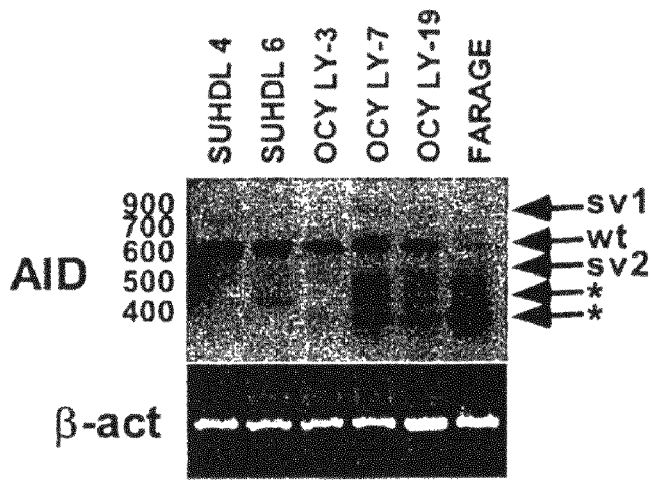
Figure 7

CONTENT DEPENDENT INHIBITORS OF CYTIDINE DEAMINASES AND USES THEREOF

CROSS REFERENCE TO RELATED APPLICATIONS

This application claims priority to U.S. Provisional Application 60/568,490, filed May 6, 2004.

This invention was made with government support under Grants DK43739 and AI54369 and RR15934 awarded by the National Institutes of Health, and a grant from the Air Force Office for Scientific Research. Therefore, the government may have certain rights in the invention.

BACKGROUND OF THE INVENTION

Cytidine deaminases (CDAs) represent a novel class of enzymes involved in pyrimidine metabolism in both lower and higher organisms. The fundamental cytidine deaminase reaction requires a cytidine deaminase with bound $Zn^{2+}$, which serves as a Lewis acid in a reaction that activates a water. The activated water serves as a nucleophile that attacks the C4 ($sp^2$) position of the cytosine ring leading to a transition state that proceeds through a tetrahedral intermediate ($sp^3$). A subsequent change from the enol to keto base tautamer results in an aprotic exocylic oxygen at C4, accompanied by the elimination of ammonia. The product is the uridine nucleoside. The reverse reaction is unfavorable and does not occur to any measurable extent on the enzyme.

The synthesis and inhibitory activity of cytidine deaminase inhibitors have been described in the art (Kim, C. H., et al., J Med Chem, 29(8):1374-80, 1996; Laliberte, J. Cancer Chemother Pharmacol, 30(1): 7-11, 1992; Driscoll, J. S., et al., J Med Chem, 34(11):3280-4, 1991; Xiang, S., et al., Biochemistry, 36(16):4768-74, 1997; Xiang, S., et al., Biochemistry, 35(5):1335-41, 1996; Xiang, S., et al., Biochemistry, 34(14):4516-23, 1995; Frick, L., et al., Biochemistry, 28(24):9423-30, 1989.)

Historically the development of the zebularine nucleoside was based on the need for an inhibitory agent to impair the function of cytidine deaminases that metabolize antileukemic nucleosides such as 5-aza-2'-deoxycytidine (5-aza-dC) and cytidine arabinoside (ara-C) (Foubister, V., Drug Discov Today 8(10):430-1, 2003.) Such undesirable cytidine deaminase activity renders these therapeutics ineffective as antileukemia drugs. By comparison to 5-aza-dC and ara-C, zebularine is considerably less cytotoxic and more chemically stable, up to pH 12, in aqueous solution (Barchi, J. J., Jr., J. Organic Chem., 57:536-541, 1992; Kelley, J. A., et al., J Med Chem, 29(11):2351-8, 1986). Interest in zebularine as a therapeutic has emerged due to its efficacy as an anti-DNA methyltransferase drug Cheng, J. C., et al., J Natl Cancer Inst, 95(5):399-409, 2003; Zhou, L., et al., J Mol Biol, 321(4):591-9, 2002). In many types of cancers, tumor suppressor genes become inactivated due to abnormal methylation of their promoter regions. Clinical studies have demonstrated that oral administration of zebularine can reactivate genes that naturally suppress cancer through a mechanism that inhibits methylation. However, in animal studies, the efficacy of zebularine in free nucleoside form was limited due to the very high oral doses needed (1 g per kg body weight in mouse models Foubister, V., Drug Discov Today, 8(10):430-1, 2003). Furthermore, zebularine is cytotoxic due to its non-specific action against the enzymes of pyrimidine metabolism and indiscriminate targeting of DNA methyltransferases. What is needed in the art are inhibitors that selectively target cytidine deaminases with the property that inhibition has little or no cytotoxicity.

In this regard, cytidine deaminases active on cytidine or deoxycytidine in RNA or DNA (respectively) and that belong to a family of enzymes known as APOBEC-1 Related Proteins (ARPs) have been shown to play a role in modifying nucleic acid sequences and thereby giving rise to altered protein expression and/or serving as antiviral agents. ARPs modify select cytidines or deoxycytidines in RNA or DNA through targeting sequence specific signals within 5' and/or 3' sequences flanking the modified base. The flanking sequences represent a unique context within which the target cytidine of deoxycytidine is embedded.

SUMMARY

The invention discloses context dependent inhibitors of cytidine deaminases, (Cytidine deaminase inhibitors) and methods for their use.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 1 shows a summary of the relevant chemical mechanism and stereochemical aspects of the fundamental cytidine deaminase reaction. The noteworthy aspect of the reaction is that it requires a cytidine deaminase with bound $Zn^{2+}$, which serves as a Lewis acid in the reaction to activate water. Activated water serves as a nucleophile that attacks the C4 ($sp^2$) position of the cytosine ring leading to a transition state that proceeds through a tetrahedral intermediate ($sp^3$), for which the enzyme exhibits its greatest affinity. A change from enol to keto base tautamer results in a keto oxygen at C4, accompanied by the elimination of ammonia. The product is the uridine nucleoside. The reverse reaction is unfavorable and does not occur to any measurable extent on the enzyme.

FIG. 2 shows the stereochemical property of zebularine that makes it such an effective inhibitor of cytidine deaminase activity. The enzyme modifies the analog base in a mechanism-based manner. Specifically, when the zebularine nucleoside is bound by the enzyme active site, the de-oxo C4 position undergoes nucleophilic attack in a manner analogous to that observed for the cytidine substrate seen in FIG. 1. However, due to the absence of a suitable leaving group (i.e. hydrogen in lieu of ammonia), the enzyme remains trapped in complex with the C4-hydroxylated analog, which mimics the tetrahedral geometry of the transition state. Hence, the enzyme exhibits much greater affinity for the 3,4 dihydrouridine adduct than the zebularine ground-state. Therefore, an inhibitor need not be one that is chemically susceptible to nucleophilic attack, but can be one that mimics the chemical properties of the intermediate in geometry and charge.

FIG. 3 shows how representative substrate specificity is achieved for the cytidine deaminase APOBEC-1 whose target site interaction is conferred through direct interaction with an auxiliary factor, ACF. The latter complementation factor binds APOBEC-1, as well as an RNA sequence that flanks the deaminated site (C6666) known as the 'mooring sequence. RNA recognition by ACF requires 3 tandem RNA recognition motifs (RRMs) that interact with high affinity ($K_d$=~8 nM) on the mooring sequence. Due to their sequence homology to APOBEC-1, APOBEC related proteins (ARPs) can require similar high-specificity auxiliary factors in substrate targeting. One analysis of the ARP known as the activation induced deaminase (AID) showed that deoxycytidine is targeted for modification within immunoglobulin genes in the context of single stranded DNA sequence (A/G-G-C-A/T (RGYW) or A/T-A/G-C-C/T (WRCY) within Ig genes for SHM, CSR and on reporter DNAs. However, many other sites were modified as well (Harris, R. S., Petersen-Mahrt, S. K. and Neuberger, M. S. (2002). *Mol Cell* 10, 1247-53; Petersen-Mahrt, S. K., et al., (2002). *Nature* 418, 99-104; Yu, K., et al., (2003). *J. Biol. Chem.* 279, 6496-6500. Targeting of deoxycytidines within the HIV-1 single stranded minus strand intermediates during viral reverse transcription demonstrated a target sequence preference of ACCC or GCCC in which the third C is deaminated (Zhang et al., (2003) *Nature* 424, 94-8; Lecossier et al., *Science* 300, 1112).

In the editosome deamination model, APOBEC-1 is the core editing enzyme of a macromolecular complex required for site specific C to U deamination of the mRNA encoding the serum lipoprotein apoB. By itself APOBEC-1 exhibits little RNA binding specificity; however, through interactions with APOBEC-1 complementation factor, ACF, the editing enzyme is guided to the correct target site to perform its natural biochemical C to U deamination function because ACF binds selective to the mooring sequence. This paradigm of auxiliary proteins and their selective interaction with target sequences is a theme with the ARP family described throughout.

FIG. 4 shows several other context dependent inhibitors (Cytidine deaminase inhibitors) of ARP-related cytidine deaminases other than zebularine.

FIG. 5 shows a description of the sequence environment employed for the synthesis and application of cytidine deaminase inhibitors containing embedded zebularine. The single stranded construct is envisioned for APOBEC-1, which entails incorporating specific sequences of the tripartite apoB mRNA substrate; Z marks the position of zebularine. A single-stranded or double-stranded "bubble" target provides a substrate mimic for AID.

FIG. 6 shows that the expression of CEM15 in 293T cells resulted in at least a 100-fold decrease in Vif-viral infectivity compared to particles generated in parental 293T cells. The low level of GFP expression from vif(−), CEM15+ particles is indistinguishable from background fluorescence in control cells [0.2%]. This assay is amenable to the use of existing HIV-1 proviral isotyped vectors that are deleted for different regions and different amounts of the HIV-1 genome. Deleted genes can be provided in trans by co-transfection of suitable expression plasmids.

FIG. 7 shows expression of AID transcripts in human B cell lymphoma lines. Total RNA was extracted from the cell lines indicated, reverse transcribed and subjected to PCR amplifications with primers to AID and α-actin as described (McCarthy et al. (Blood (94) Feb. 13, 2003). Amplified fragments were separated on 1.2% agarose gels. AID PCR products were then transferred onto Hybond nylon filters, hybridized to a $^{32}$P-labeled internal AID oligonucleotide, and the hybridization signal was detected using phosphorimager screens. Note the different AID band patterns present in the individual lymphoma lines. (wt, wild-type-size AID band (646 bp); sv1/sv2, bands compatible with size of known splice variants; *, potential novel splice variants.)

Figure 8:
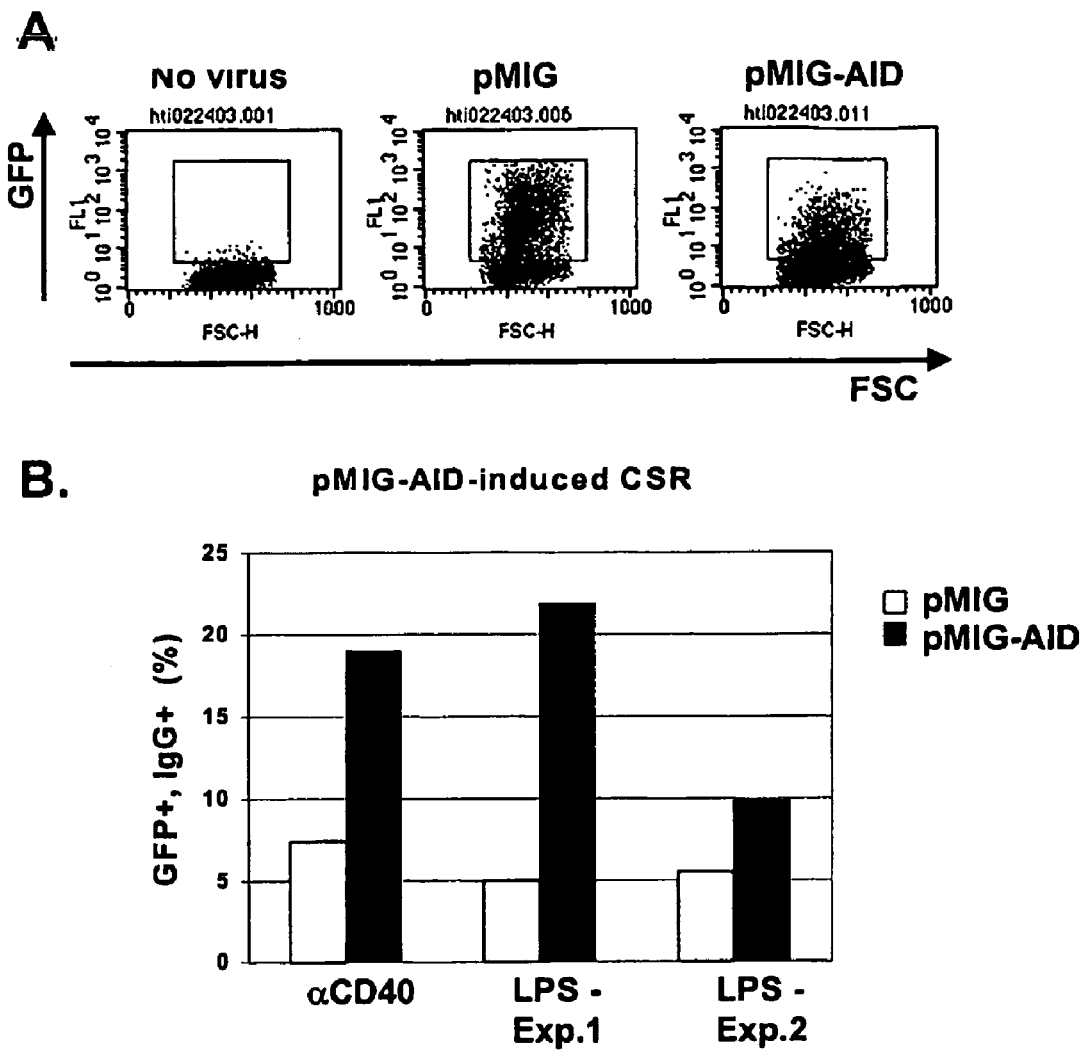

FIG. 8 shows retroviral expression of AID. His-tagged murine AID cDNA was cloned into the pMIG retroviral vector (Pear et al. Blood 92:378-3792, 1998) and retroviral particles were generated using the Phoenix-Eco packaging cell line. Viral supenatants were used to transduce in vitro activated B cell. Panel A: Day1 LPS-activated lymphoblasts were incubated with Phoenix-Eco virus-free supernatant (No virus), pMIG virus containing supernatants and pMIG-AID containing supernatants, in the presence of 4 μg/ml polybrene. At day 5 of culture, cells were harvested and analyzed by flow cytometry (FSC/SSC live-gated cells shown in plots). Transduction efficiencies average 30-40% with the pMIG virus, and 20-30% with pMIG-AID. Note that GFP expression is lower for pMIG-AID than for pMIG, probably because the AID in the first cistron position diminished expression of the IRES-GFP module (therefore, transduction efficiencies with pMIG-AD may be somewhat underestimated). Panel B: Day 5 cells from αCD40- (one experiment) and LPS-stimulated cultures transduced with either pMIG (open bars) or pMIG- were stained with PE-conjugated anti-IgG antibodies (αIgG1 for CD40 culture, αIgG2b/αIgG3 for the LPS cultures), analyzed by flow cytometry, and rates of IgG switching in transduced, GFP+ cells compared. Note how pMIG-AID transduction increases IgG switching rates by 2-4 folds, indicating expression of functional A/D.

Figure 9:
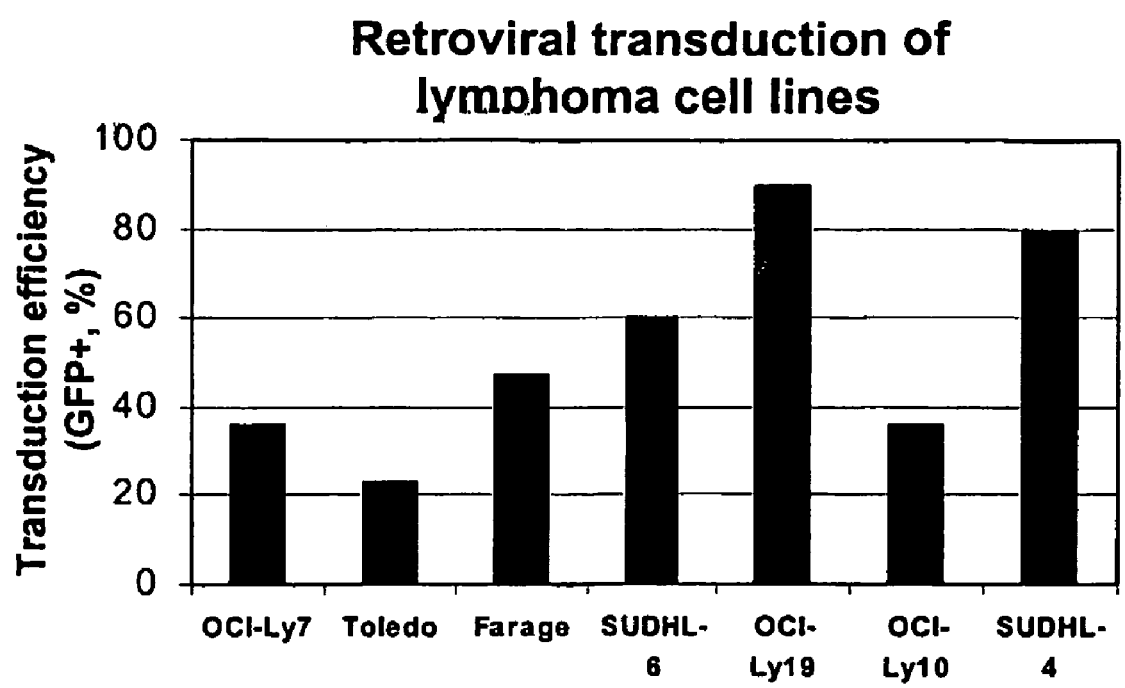

FIG. 9 shows retroviral transduction of human B lymphoma cells. Cultured cells from the indicated lymphoma lines were transduced with an RD114-packaged GFP-expressing retrovirus using the flow-through method (Chuck et al. Hum Gene Ther 7:743-750, 1996). 48 hours after transduction, cells were analyzed by flow cytometry for GFP expression. Efficiencies vary between 20% and >80%.

Figure 10:
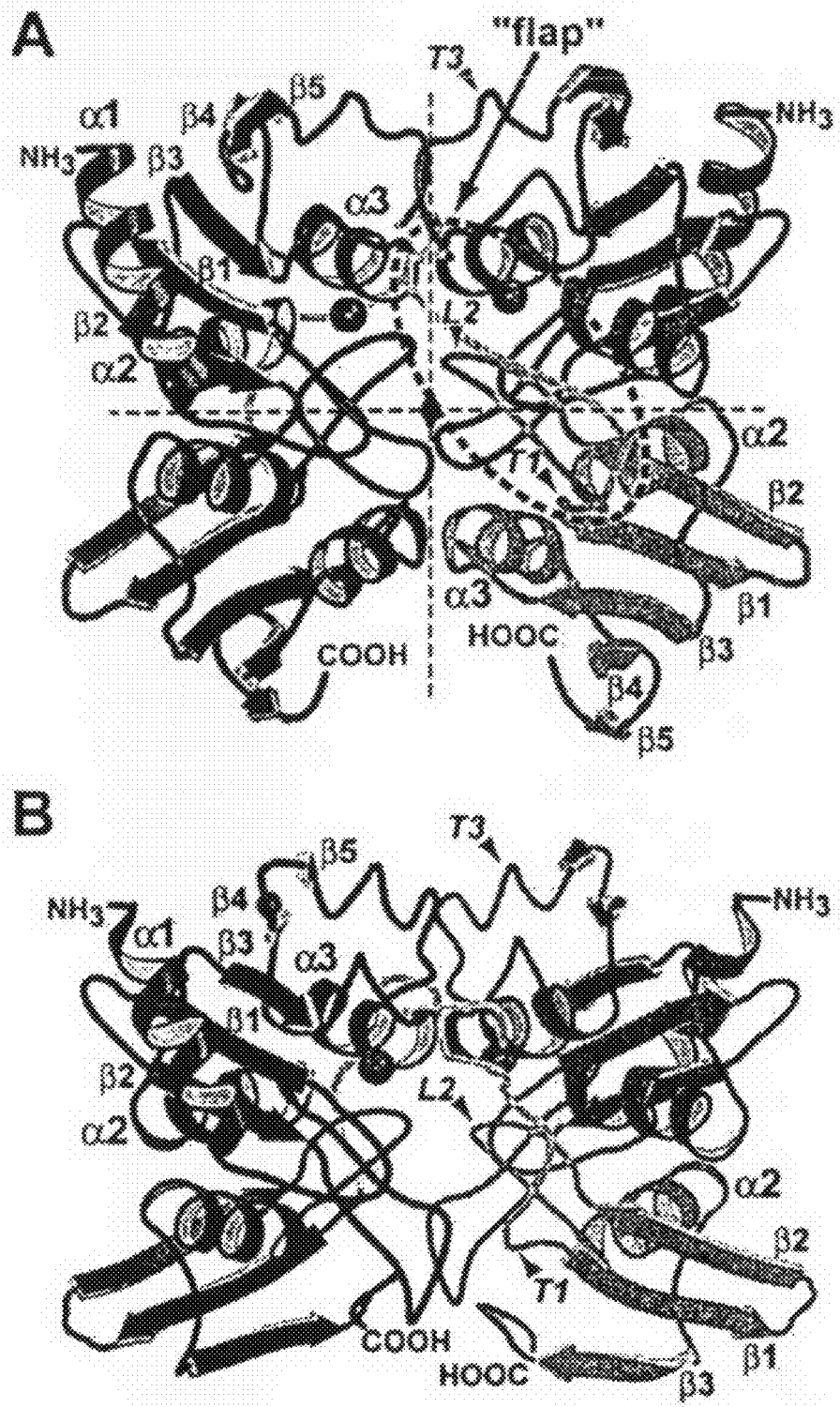

FIG. 10 Ribbon representations of HsAPOBEC-1 and HsAID comparative models. (A) The dimeric APOBEC-1 model with polypeptide chains colored: purple and red (NTCD and NCCTD); and blue and green (NTCD and NCCTD). A central flap (cyan with hatched oval) connects the NTCD to the NCCTD. Each NTCD coordinates $Zn^{2+}$ (dark green sphere). Trans-acting structure elements that form the purple active site are: T1 and L2 (green NCCTD), flap (cyan with hatched circle) and T3 (blue NTCD). The symmetry axis in black represents a proper dyad; the blue axes represent improper (pseudo) 2-fold rotations. (B) The dimeric AID structure as in 2B. The subunit interface of AID obeys $D_2$ symmetry analogous to APOBEC-1, but axes were omitted for clarity.

Figure 11:
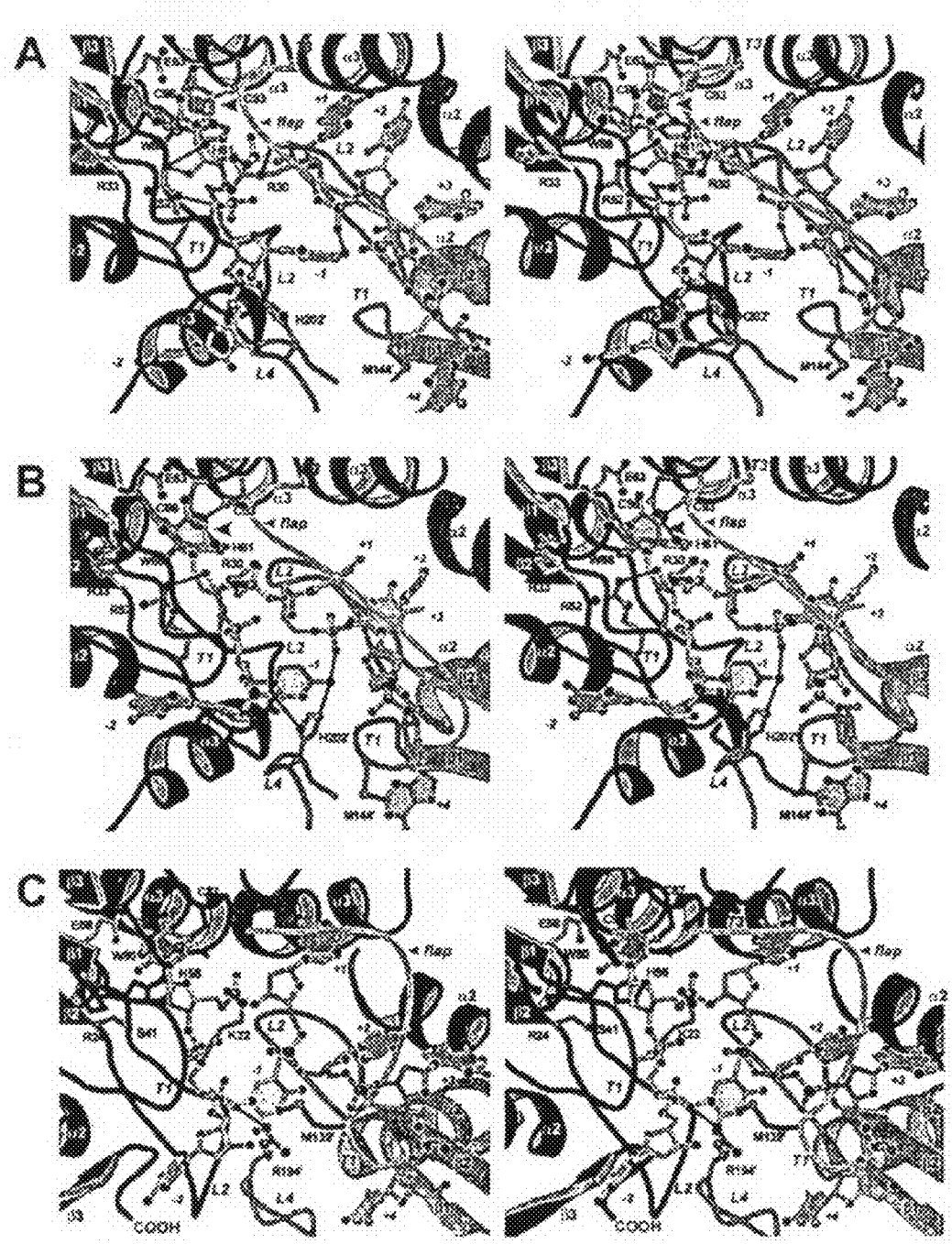

FIG. 11 Stereo views of the HsAPOBEC-1 and HsAID active sites with bound RNA and DNA substrates depicted as ball-and-stick models (yellow). (A) The APOBEC-1 active site with bound apoB mRNA substrate 5′-GAUAU$_{6666}$AA-3′. (B) The APOBEC-1 active site with bound DNA substrate 5′-d(ATCTC*CG)-3′, described as an rpoB mutation hot spot (13). (C) The AID active site with bound DNA substrate 5′-d(TAAGU*TA)-3′, described as an SHM hot spot (14). Residues mutated in HIGM2 syndrome are colored red. For all diagrams, the protein Cα backbone is drawn as a ribbon showing contributions of both polypeptides chains of the dimer (i.e. magnified views of FIGS. 10A and 10B). Basic residues (light blue), acidic residues (pale pink), and aromatic residues (gray) are drawn as stick representations. Predicted hydrogen bonds and ionic interactions with $Zn^{2+}$ are depicted as black lines. The sites of base deamination are indicated by red arrowheads. For clarity, not all amino acids are shown.

Figure 12:
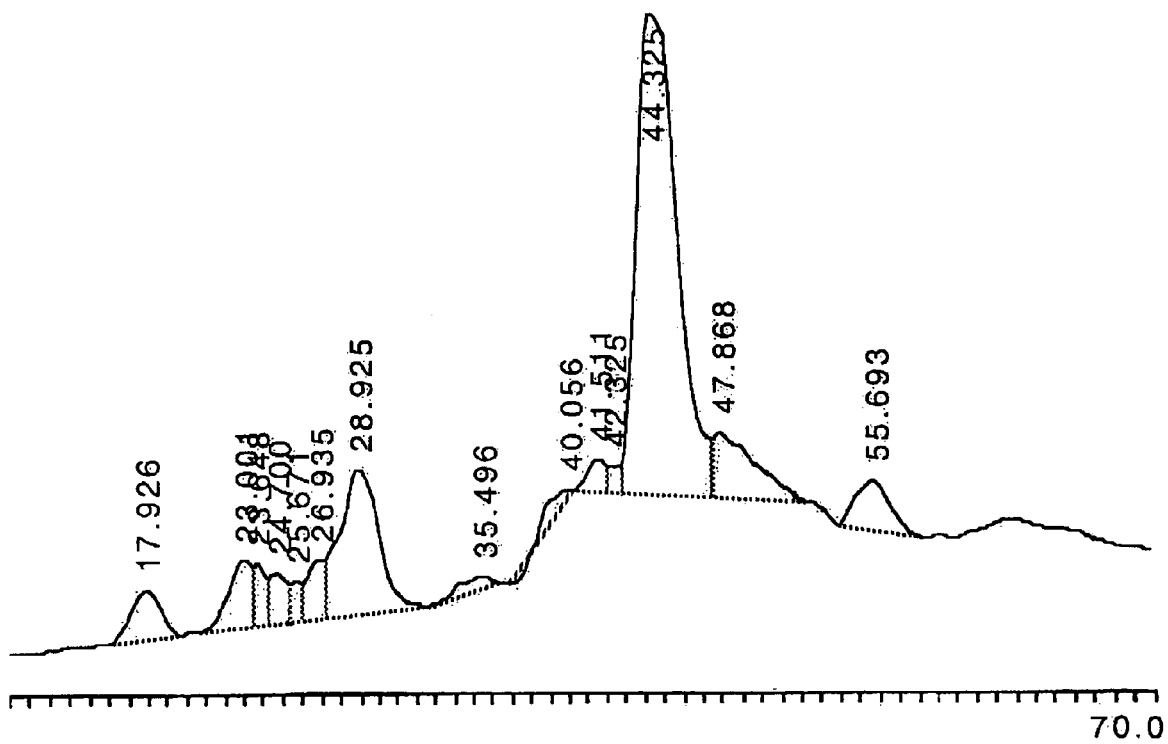

FIG. 12 shows the product eluted in the synthesis of a context dependent inhibitor of DNA harboring 5-methyl-2′-deoxyzebularine. A sequence was synthesized was a 15-mer comprising: 5′-d(AGC-TAG-(dmZ)-TAA-GTT-AT)-3′ (SEQ ID NO: 22), where one of the edited positions has been replaced by 5-methyl-2′-deoxyzebularine denoted (dmZ) (Example 1). The product eluted as a single peak with a retention time of 44.3 min; failure sequences and impurities were clearly separated in this step. The DNA was detected at 260 nm and the pooled material was lyophilized to dryness. The yield was 25% (nearly 2 mg).

Figure 13:
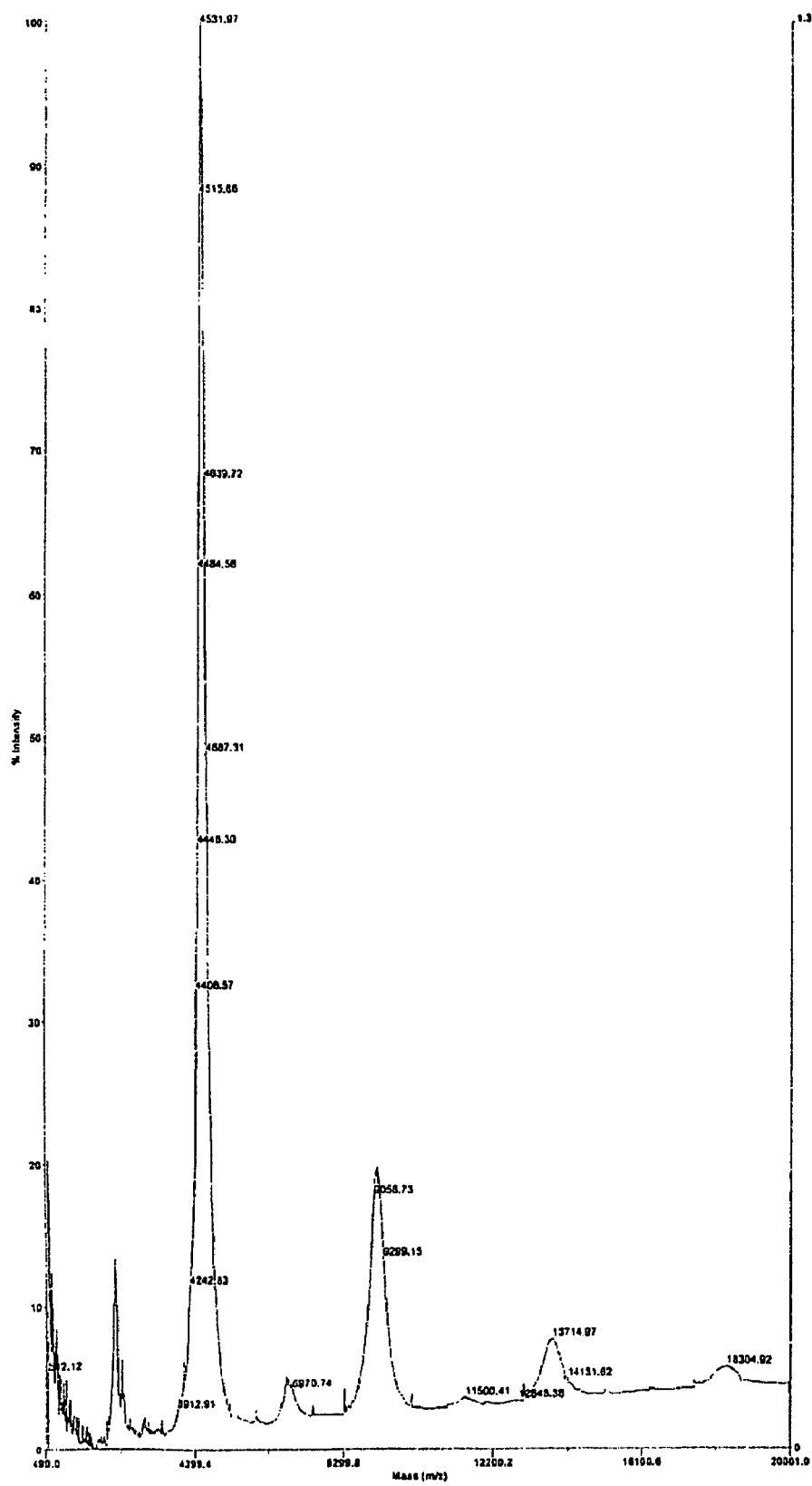

FIG. 13 shows MALDI/TOF mass spectrometry for 5-methyl-2'-deoxyzebularine. The major peak was observed at an m/z of 4532. This result demonstrates the existence of an oligomer of the correct molecular weight that represents the largest component of the sample.

DESCRIPTION OF THE PREFERRED EMBODIMENTS

The invention provides compounds that inhibit cytidine deaminase, as well as methods of using, identifying, and making such compounds. The compounds, cytidine deaminase inhibitors (also referred to as Cytidine deaminase inhibitors), are useful in preventing or treating a variety of diseases as well as aiding in combination with other treatment therapies. Described herein are cytidine deaminase inhibitors of cytidine deaminases, including APOBEC-1 and APOBEC-1 related proteins (ARPs).

Cytidine deaminase inhibitors comprise a polymeric substrate having a targeting function and an inhibiting moiety. The targeting polymeric substrate can be directed to a cytidine deaminase or a cytidine deaminase auxiliary protein. The inhibiting moiety can be a nucleoside. The nucleic acid sequence of the polymeric substrate can contain a sequence that binds the cytidine deaminase. For example, the sequence can be a RNA or DNA and can flank the zebularine nucleotide 5', 3' or both 5' and 3' (as is the case with the tripartite motif containing the mooring sequence within apoB mRNA i.e., the mooring sequence of APOBEC-1, is located 3' of the edited site at C6666, a spacer sequence lies immediately 3' of C6666 and an enhancer element lies immediately 5' of C6666). Alternately, the polymeric substrate binds the auxiliary protein The cytidine deaminase inhibitor can inhibit a cytidine deaminase or an auxiliary protein, by, for example, complexing with the cytidine deaminase or the auxiliary protein in a manner that blocks the cytidine deaminase function. The cytidine deaminase inhibitors can also chemically or structurally alter the cytidine deaminase or auxiliary protein so as to inhibit its ability to deaminate.

Optimally, the chemical property of cytidine deaminase inhibitors that causes them to be effective inhibitors of cytidine deaminase activity is that the enzyme modifies the analog base in a mechanism-based manner. For example, when a zebularine nucleoside is bound by the enzyme active site, the de-oxo C4 position undergoes nucleophilic attack (FIG. 2) in a manner analogous to that observed for the cytidine substrate (FIG. 1). However, due to the absence of a suitable leaving group (such as ammonia), the enzyme remains trapped in complex with the hydroxylated analog, which mimics the tetrahedral geometry characteristic of the transition state. Hence, the enzyme exhibits much greater affinity for the 3,4 dihydrouridine adduct than the zebularine ground-state. However, the nature of the cytidine deaminase inhibitor need not be one that requires strict chemical reactivity (defined as geometric transformation). The cytidine deaminase inhibitor functions by mimicking the tetrahedral intermediate preferred by the enzyme as representative of the charge and geometry observed in the transition state. For example, 3,4 5,6-tetrahydrouridine embedded within the substrate can act in an inhibitory manner. There are several examples of cellular and viral mRNA editing reactions in mammalian cells. (Grosjean and Benne (1998) Modification and Editing of RNA, ASM Press, Washington D.C.; Smith et al. (1997) RNA 3: 1105-23). Two examples of such editing mechanisms are the adenosine to inosine and cytidine to uridine conversions. (Grosjean and Benne, 1998; Smith et al. Trends in Genetics 12:418-24, 1996; Krough et al. J. Mol. Biol. 235:1501-31, 1994). The latter enzymes can be expected to be inhibited by cytidine deaminase inhibitors with the form of nebularine (which is the purine version of zebularine). Editing can also occur on both RNA and on DNA, and typically these functions are performed by different types of deaminases.

Cytidine deaminases are responsible for cytidine to uridine conversions. This group of enzymes also includes deoxycytidine deaminases, which are responsible for deoxycytidine to uridine conversions. The term "cytidine deaminase" used throughout the application is interchangeable with "deoxycytidine deaminase." "Cytidine deaminases" also include those deaminases active on both DNA and RNA. As described in the foregoing section, this simplification stems from the fact that APOBEC-1 and ARPs can act on single stranded RNA and/or single stranded DNA.

The most highly studied Cytidine Deaminase Active on RNA (CDAR), which acts upon polymeric nucleic acid substrates, is the apoB editing catalytic chain-1, APOBEC-1 (Wedekind, J. E., et al., Trends Genet, 19(4):207-16, 2003). The selectivity requirements of APOBEC-1 in editing of apoB RNA reporters was similar to that of the yeast enzyme CDD1 when the respective proteins were overexpressed in yeast (Dance et al., (2000) *Nucleic Acids Res.* 28, 424-49; Dance et al., (2001) *Nucleic Acids Res.* 29, 1772-80). Hence, the structure of CDD1 provided a tenable connection between known CDA and yeast cytosine deaminase (ScCD) enzymes, and the family of mammalian APOBEC related proteins. Consequently, four empirically derived deaminase structures were employed in comparative modeling of HsAPOBEC-1 and HsAID. Preparation of a structural template revealed major differences in the modes of substrate binding by CDA and ScCD enzymes. Comparative modeling of APOBEC-1 and AID suggested that the domain interface between subunits influences the positioning of ribose binding loops as in CDAs and that a variably-sized flap at the catalytic site regulates access based on substrate size, which was corroborated by functional data. Both AID and APOBEC-1 targeted DNA in vivo (Harris, R. S. (2002) *Mol. Cell.* 10, 1247-53; Petersen-Mahrt, S. K., (2002) *Nature* 418, 99-103.). However, APOBEC-1 did not substitute for AID in CSR or SHM (Eto, T., (2003) *Proc. Natl. Acad. Sci. U.S.A.* 100, 12895-8) and AID could not substitute for APOBEC-1 in apoB mRNA editing (Muramatsu, M. (1999) *J. Biol. Chem.* 274, 18470-6) showing each enzyme has an inherent specificity for its own substrate. Specifically, models of APOBEC-1 and AID (FIGS. 10 and 11) indicated either DNA or RNA substrates could be accommodated by their active sites, but only in single-stranded form.

APOBEC-1 is the core editing enzyme of a macromolecular complex or editosome required for site specific C to U deamination of the mRNA encoding the serum lipoprotein apoB. By itself APOBEC-1 exhibits little RNA binding specificity; however, in the presence of the APOBEC-1 complementation factor (ACF) the editing enzyme is guided to the correct target site to perform its natural biochemical C to U deamination function (Mehta, A., et al., *Mol Cell Biol* 20, 1846-54, 2000). APOBEC-1 target specificity is conferred through direct interaction with ACF, which mediates contact with a flanking RNA 'mooring sequence' located 3' of the edited site at C6666 (FIG. 3). RNA recognition by ACF requires 3 tandem RNA recognition motifs (RRMs) that interact with high affinity ($K_d$=~8 nM) on the mooring sequence (FIG. 3) (Smith, H. C., *Cell Biol,* 4:267-78, 1993; Mehta, A. and D. M. Driscoll, RNA, 8(1):69-82, 2002; Blanc, V., et al., *J Biol Chem,* 276: 46386-93, 2000.)

Due to the tripartite substrate sequence motif of apoB mRNA, which includes (i) a mooring sequence, (ii) an "enhancer" sequence and (iii) a "spacer" sequence, which collectively flank the C6666 editing site in apoB mRNA, the site appears unique compared to all other mammalian mRNA, rRNA and tRNA sequences. Hence the intermolecular interactions between APOBEC-1, ACF, and the RNA substrate can be selectively targeted by incorporating the unique tripartite sequence features into the cytidine deaminase inhibitor.

As a therapeutic, an understanding of APOBEC-1 is relevant to heart disease and stroke. Current lipid-lowering therapies, such as statins, have shown effective potency as inhibitors of hydroxymethylglutaryl (HMG)-CoA reductase, which catalyzes the committed step in the synthesis of cholesterol. The other lipid-lowering bile-acid-binding resin therapy has shown efficacy via sequestering the bile acids in the intestine, thereby interrupting the enterohepatic circulation of bile acids and increasing the elimination of cholesterol from the body. These are valid therapies for patients with hyperlipidemia. However, up to 30% of the patients have been observed to indicate adverse reactions to these therapies, showing that alternative therapies have a market. Moreover the latter therapies are less effective on patient suffering from metabolic syndrome.

Cholesterol is carried in the blood from one tissue to another as lipoprotein particles by specific carrier proteins called apolipoproteins. Apolipoprotein B (apoB) is an integral and non-exchangeable structural component of lipoprotein particles referred to as chylomicrons, very-low-density lipoprotein (VLDL) and low-density lipoprotein (LDL). ApoB circulates in human plasma as two isoforms, ApoB100 and apoB48. ApoB100 can be converted into ApoB48 by the enzyme APOBEC-1 (ApoB mRNA editing catalytic subunit-1). With the help of auxiliary factors, APOBEC-1 can stop the synthesis (production) of ApoB100 form and start the synthesis of ApoB48 form in cells. ApoB100 and ApoB48 play different roles in lipid metabolism. Various studies indicated that ApoB100-associated lipoproteins (VLDL and LDL) are much more atherogenic than ApoB48-associated lipoproteins.

Stimulating hepatic ApoB mRNA editing is a way to reduce serum LDL through the reduction in synthesis and secretion of ApoB100 containing VLDL. In most mammals (including humans), ApoB mRNA editing is carried out only in the small intestine. Studies found that the presence of substantial editing in liver is associated with a less atherogenic lipoprotein profile compared with animals that do not have liver editing activity. APOBEC-1 is expressed in all tissues that carry out ApoB mRNA editing. Human liver does not express APOBEC-1 but it does express sufficient auxiliary proteins to complement exogenous APOBEC-1 in ApoB mRNA editing in transfected cells. Therefore, induction of editing in human liver reduces apoB100 synthesis and thereby reduce the levels of circulating LDL cholesterol.

Based on population studies the etiology of atherosclerosis falls into four causalities (i) hypercholesterolemia (described above), (ii) pro-inflamatory reactions, (iii) pro clotting, and (iv) metabolic syndrome (Corestti, J. P. et al., (2003) *Atherosclerosis* 171, 351-8; Moss, A. J. (1999) *Circulation* 99, 2517-22, herein incorporated by reference in their entireties). Cytidine deaminase inhibitor-based compounds are indicated for the latter causality as it is intestinally derived B48 containing reminants of chylomicrons that are small and accumulate within the walls of arteries due to their heightened affinity and high abundance in the blood of approximately 25% of the total population at risk for atherogenic disease. Chylomicron reminants appear in blood maximally within 1-2 hours following a meal (as a consequence of intestinal absorption) and are present in proportion to the fat content of the meal.

The small intestine from all mammals edits 80-100% of apoB mRNA produced (Backus, J. W. (1990) *Biochem. Biophys. Res. Commun.* 170, 513-8; Greeve, J. (2003) *J. Lipid Res.* 34, 1367-83, herein incorporated by reference in their entireties) and secretes B48 chylomicrons assembled in response to the presence of dietary lipids into the lymphatic system. Transgenic apobec-1 gene knock-out mice do not edit apoB mRNA and as a consequence assemble chylomicrons on apoB100 protein. These mice have a normal phenotype (Farese, R. V. et al., (1996) *PNAS USA* 93, 6393-8; Nakamuta, M. et al., (1996) *J. Biol. Chem.* 271, 25981-8, herein incorporated by reference in their entireties), but do have an elevated risk of atherosclerosis due to the lack of hepatic editing. This leads to hepatic apoB100 VLDL secretion into the blood steam and subsequent metabolism to apoB100 LDL. cytidine deaminase inhibitors selective for APOBEC-1 inhibits apoB mRNA editing within intestinal cells thereby resulting in exclusive secretion of apoB100 containing chylomicrons that are metabolized to large particles that are cleared by the liver with reduced rates of artery wall accumulation.

In addition to the established apoB mRNA editing activity of APOBEC-1, C to U modifications have been detected in the tumors of approximately one quarter of individuals afflicted with the disease neurofibromatosis type I (NF1) (Skuse, G. R., et al., (1996) *Nucleic Acids Res,* 24, 478-85, herein incorporated by reference in its entirety). The translation product of NF1 mRNA, is a tumor suppressor GTPase activating protein (GAP), neurofibromin, which inhibits cell growth signaling mediated by the GTPase dependent Ras oncogene product. Due to the presence of a mooring-sequence-like segment downstream of C3916 in the neurofibromin mRNA, this site can be edited converting an Arg to an in-frame translation stop codon. If the product of the edited mRNA escapes nonsense mediated decay, the result is a truncated protein missing the C-terminal GAP domain providing a potential mechanism for disease. APOBEC-1 mRNA editing of neurofibromin mRNA appears to play a direct role in NF1 disease (Mukhopadhyay, D., et al., (2002) *Am J Hum Genet,* 70, 38-50, herein incorporated by reference in its entirety). Due to the unique tripartite motif in NF1 mRNA editing of C3916 in NF1 mRNA can be selectively inhibited by cytidine deaminase inhibitors. This is an instance where in the same enzyme (APOBEC-1) can be targeted by two different cytidine deaminase inhibitors (one mimicking NF1 and the other apoB RNA) with the possibility of tissue specific effects due to the differential affinity and competition of the cytidine deaminase inhibitor with the endogenous mRNA substrate that is selectively expressed in each tissue (e.g. NF1 cytidine deaminase inhibitor inhibits APOBEC-1 editing only in neuronal tissue and apoB cytidine deaminase inhibitor inhibits editing only in liver and intestine).

Unregulated transgenic expression of APOBEC-1 confers susceptibility to liver cancer (Sowden, M., (1996) *J Biol Chem,* 271:3011-7; Yamanaka, S., et al., (1995) *PNAS USA,* 92, 8483-7, herein incorporated by reference in its entirety), possibly as a result of nonspecific mRNA editing affecting the NAT1 translational repressor. Another novel mechanism leading to neoplasia that can be related to the observation that APOBEC-1-mediates stabilization of mRNA transcripts of c-myc (Anant, S. and Davidson, N. O. (2000) *Mol Cell Biol,* 20, 1982-92, herein incorporated by reference in its entirety). Although APOBEC-1 itself has marginal affinity for apoB mRNA, it has been demonstrated that it exhibits modest affinity for tandem AU-rich sequences. Disruption of this interaction by cytidine deaminase inhibitor compound can decrease c-myc stabilization, which could significantly impact the half-life of the proto oncogene product.

Two loci of APOBEC-1 related proteins (ARPs) were discovered in humans, as well as related proteins in mice and yeast (Dance, G. S., et al., (2001) *Nucleic Acids Res*, 29, 1772-80; Anant, S., et al., (2001) *Am J Physiol Cell Physiol*, 281, C1904-16; Jarmuz, A., et al., (2002) *Genomics*, 79, 285-96 all herein incorporated by reference in their entireties). A summary of human ARP proteins is provided in Table I and in Wedekind, J. E., et al., (2003) *Trends in Genet*, 19, 207-16. The cytidine deaminase inhibitors described herein can target the ARPs or their auxiliary proteins in a manner similar to APOBEC-1. For example, context dependent inhibitors applications are specifically indicated for metabolic syndrome, while apoB mRNA editing is indicated for treatment in the small intestine.

The activation-induced cytidine deaminase (AID) (e.g. a novel ARP) is required for somatic hypermutation (SHM) of immunoglobulin (Ig) genes in germinal center (GC) B cells (Muramatsu, M., et al., (1999) *J Biol Chem*, 274, 18470-6;

Oppezzo, P., et al., (2003) *Blood*, 101, 4029-32, herein incorporated by reference in their entireties). In CLL samples, AID expression was specifically associated with poor prognostic features. Paradoxically, poor prognosis in CLL correlates with the absence of Ig gene SHM (Damle, R. N., et al., (1997) *Blood*, 94, 1840-7; Hamblin, T. J., et al., (1999) *Blood*, 94, 1848-54 herein incorporated by reference in their entireties), showing that AID function is altered in these cells. AID expression in the absence of ongoing SHM is also observed in certain diffuse large B-cell lymphomas (DLBCLs), specifically those defined as "activated B cell-like" based upon gene expression profiles and surface markers (Lossos, I. S., et al., (2000) *PNAS USA*, 97, 10209-13, herein incorporated by reference in its entirety). Here too, a worse outcome is associated with the non-mutating phenotype compared to DLBCLs in which ongoing Ig SHM is detected, such as those of GC-like phenotype (Rosenwald, A., et al., (2003) *N Engl J Med*, 346, 1937-47; Alizadeh, A. A., et al., (2000) *Nature*, 403, 503-11, herein incorporated by reference in their entireties).

TABLE 1

Genetic Location and Properties of human APOBEC-1 Related Proteins (ARPs)

| Gene | Locus | Accession Number | Equivalent Names | Expressed Sequence | C to U Activity |
|---|---|---|---|---|---|
| APOBEC-1 | 12p13.1 | AAD00185 | — | Small & Large Intestine | apoB mRNA |
| APOBEC-2 | 6p21 | NP_006780 | CAB44740/ARCD1 | Cardiac & Skeletal Muscle | — |
| AID | 12p13 | NP_065712 | — | B lymphocytes | DNA |
| APOBEC-3A | 22q13.1 | NP_663745 | Phorbolin-1 | Keratinocytes | — |
| APOBEC-3B | 22q13.1 | Q9UH17 | Phorbolin-3 Phorbolin-1-related Phorbolin-2 APOBEC-1L ARCD-3 | Keratinocytes, colon | — |
| APOBEC-3C | 22q13.1 | CAB45271 | Phorbolin-1 ARCD-2/ARCD-4 | Spleen, testes, heart, thymus, prostate, ovary, uterus, PBLs, | — |
| APOBEC-3D + E | 22q13.1 | NM_145298 | — | uterus | — |
| APOBEC-3D | 22q13.1 | BF841711 | — | head and neck cancers | — |
| APOBEC-3E | 22q13.1 | Pseudogene | ARCD-6 | — | — |
| APOBEC-3F | 22q13.1 | BG_758984 | ARCD-5 | B lymphocytes | — |
| APOBEC-3G | 22q13.1 | NP_068594 | Phorbolin-like-protein, MDS019, HsCEM15 | Spleen, breast, heart, thymus, PBLs, colon, stomach, kidney, uterus, pancreas, placenta, prostate | Viral DNA |
| 22q13.1 | 22q13.1 | XP_092919 | — | — | — |
| 12q23 | — | XP_115170 | — | — | — |

Muramatsu, M., et al., (2000) *Cell*, 102, 553-63). AID is also known to be deficient in human patients afflicted with hyper IgM syndrome type II (Revy, P., et al., (2000) *Cell*, 102, 565-75). Although AID displays significant homology to APOBEC-1, it can act directly on DNA (Petersen-Mahrt, S. K., (2000) *Nature*, 418, 99-103; Harris, R. S., et al., (2002) *Mol Cell*, 10, 1247-53, herein incorporated by reference in their entireties). In GC B cells, SHM is usually restricted to Ig genes, however, AID is constitutively expressed in human B cell malignancies such as diffuse large B cell lymphomas (DLBCL) and some chronic lymphocytic leukemias (CLL), as well as in other lymphomas of both germinal center (GC) and non-GC origin (Greeve, J., et al., (2003) *Blood*, 101, 3574-80; McCarthy, H., et al., (2003) *Blood*, 101, 4903-8;

In subsets of DLBCL and CLL, AID expression is uncoupled from somatic hypermutation activity, a feature that correlates with more aggressive forms of these diseases. These characteristics show that AID function is aberrant in B cell cancers. In fact, oncogene mutations with patterns resembling SHM have been found at high frequency in B cell lymphomas. One explanation for these data is that loss of target specificity during the SHM process may be involved in the transformation and/or progression of B lymphoid malignancies. Constitutive AID expression in transgenic mice was shown to cause T cell lymphomas and pulmonary adenomas, formally demonstrating AID's oncogenic potential. Finally, and most significantly, transgenic expression of AID under a ubiquitous promoter induces T cell lymphomas and pulmonary adenomas, accompanied by extensive mutations in the c-myc protooncogene, confirming that AID can act as a bona fide oncogene when ectopically expressed (Okazaki, I. M., et al., (2003) *J Exp Med,* 197, 1173-81,). Hence, the oncogenic effect of AID appears to be attributable to loss of regulation over a "normal" DNA mutase activity, as a consequence of over-expression of AID isoforms with altered function, or defects in cofactors involved in determining specificity of SHM targeting. The consequence is genome-wide mutagenesis contributing to rapid accumulation of multiple oncogenic hits, resulting in accelerated tumor progression. Therefore, selectively disabling the deaminase activity of AID in neoplastic cells using a cytidine deaminase inhibitor is a useful therapeutic strategy.

Another ARP of immediate medical relevance is hsCEM15/APOBEC-3G (Table 1), which has been described as a broad antiviral agent that reduces the infectivity of the human lentivirus, HIV-1 (Mangeat, B., et al., 2003, *Nature* 424, 99-103). The virus contains a 10-kb single-stranded, positive-sense RNA genome that encodes three major classes of gene products. One class known as "auxiliary" proteins (Vpr, Vif, Vpu, Nef) are not required for efficient virus replication in at least some settings in cell culture. One of these proteins, Vif (virion infectivity factor), is required for efficient virus replication in vivo, as well as in certain host cell types in vitro (Fisher, A. G., et al., (1987) *Science,* 237:888-93; Strebel, K., et al., (1987) *Nature,* 328:728-30), because of its ability to overcome the action of a cellular antiviral system (Simon, J. H., et al., (1998) *Nat Med,* 4, 1397-400; Madani, N. and D. Kabat, (1998) *J Virol,* 72, :10251-5).

The in vitro replicative phenotype of vif-deleted molecular clones of HIV-1 is strikingly different in vif-permissive cells (such as 293T cells, and the SUPT1 and CEM-SS T cell lines), as compared to vif-non-permissive cells (such as primary T cells and macrophages). In the former cells, vif-deleted HIV-1 clones replicate with an efficiency that is essentially identical to that of wild-type virus, whereas in the latter cells, replication of vif-negative HIV-1 mutants is arrested due to a failure to accumulate reverse transcripts and to generate infectious proviral integrants in the host cell (Courcoul, M., et al., (1995) *J Virol,* 69, :2068-74; Simon, J. H. and M. H. Malim, (1996) *J Virol,* 70, 5297-305; von Schwedler, U., et al., (1993) *J Virol,* 67, 4945-55; Sova, P. and D. J. Volsky (1993) *J Virol,* 67, 6322-6). These defects are due to the expression of host cell protein CEM15 in vif-non-permissive cells (Sheehy, A. M., et al., (2002) *Nature,* 418, 646-50). The instability of viral reverse transcripts in vif-non-permissive cells in the absence of Vif, and the fact that both Vif and CEM15 are present in HIV-1 virions (Sheehy, A. M., et al., (2002) *Nature,* 418, 646-50; Camaur, D. (1996) *J Virol,* 70, 6106-11; Liu, H., et al., (1995) *J Virol,* 69, 7630-8), strongly suggests that the CEM15 antiviral activity may be derived from effects on viral RNA or reverse transcripts (viral DNA). This HIV RNA/DNA modification hypothesis is the most likely explanation for the CEM15 effect on viral infectivity. Due to the "broad" anti-viral activity described for CEM15, cytidine deaminase inhibitors can be used in the context of retroviral-based expression of exogenous nucleic acids.

The reason(s) for the modest success of retroviral mediated delivery of gene therapy (Chang, L. J. and E. E. Gay, (2001) *Curr Gene Ther,* 1, 237-51) can be at least in part due to the activity of enzymes like CEM15. It is likely that editing enzymes in general act to prevent retroviral infection through the body. ARPs and Adenosine Deaminase active on RNA (ADRA1 and ADAR2) are selectively expressed tissues and regions within tissues (Barbon, A. et al. (2003) *Brain Res.* *Mol Brain Res.* 117, 168-78; Sowden et al., (2000) *J. Cell Sci.* 115, 1027-39, herein incorporated by reference in their entireties). Each enzyme requires a unique flanking sequence context for cytidine, deoxycytidine or adenosine editing. CEM15 (Zhang et al., (2003) *Nature* 424, 94-8; Lecossier et al., *Science* 300, 1112) and ADAR1 (George, C. X. & Samuel, C. E. (1999) *PNAS USA* 96, 4621-26; Jayan, G. C. & Casey, J. I. (2002) *J. Virol.* 76, 12399-404, Casey, J. L. (2002) *J. Virol.* 76, 7385-97, herein incorporated by reference in their entireties) use target sequence and RNA secondary structure to edit viral RNA and DNA. Inactivating CEM15, ADARs or other ARPs with cytidine deaminase inhibitors can be used to selectively inhibit editing in tissues where these enzymes are expressed while allowing enzymes that were not targeted with cytidine deaminase inhibitors to remain active in other tissues. Tissues in which cytidine deaminase inhibitor therapy inactivated editing enzymes are not be able to edit retrovirus and thereby become more susceptible to gene therapy, whereas all other tissues are refractory to retroviral infection because their editing enzymes does not interact with the cytidine deaminase inhibitors and therefore remain active to modify and inactive the retroviral genome and transgenes. Cytidine deaminase inhibitor and retrovirus vectors are used in combination to not only enhance the efficiency of gene delivery but also enable retroviral delivery which are used tissue specifically.

The results of x-ray crystallographic structural studies and comparative modeling show that the overall molecular architecture and enzyme active sites of cytidine deaminases share common features that enable binding and activity on large nucleic acid substrates. Furthermore, these active sites are susceptible to inhibition by cytidine deaminase inhibitors that target all related enzymes indiscriminately. Therefore, embedding the cytidine deaminase inhibitor within specific polynucleotide target sequences preferred by each respective cytidine deaminase causes selective inhibition of the cytidine deaminase. In this context, it is possible to direct inhibition of only selected cytidine deaminase activities. The large size of the embedded cytidine deaminase inhibitor precludes interaction and cytotoxicity associated with many cytidine deaminases involved in pyrimidine metabolism.

DEFINITIONS

As used in the specification and the appended claims, the singular forms "a," "an" and "the" include plural referents unless the context clearly dictates otherwise. Thus, for example, reference to "an inhibitor" includes mixtures of the inhibitors.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

The terms "higher," "increases," "elevates," "enhances," or "elevation" refer to increases above basal levels, e.g., as compared to a control. The terms "low," "lower," "reduces," "suppresses" or "reduction" refer to decreases below basal levels, e.g., as compared to a control. For example, basal levels are normal in vivo levels prior to, or in the absence of, or addition of an agent such as a cytidine deaminase inhibitor or another molecule or ligand.

The term "test compound" is defined as any compound to be tested for its ability (efficacy) to inhibit a cytidine deaminase molecule or a deoxycytidine deaminase molecule. Also, "test compounds" include drugs, molecules, and compounds that come from combinatorial libraries where thousands of such ligands are screened by drug class.

By "subject" is meant an individual. Preferably, the subject is a mammal such as a primate, and, more preferably, a human. The term "subject" can include domesticated animals, such as cats, dogs, etc., livestock (e.g., cattle, horses, pigs, sheep, goats, etc.), and laboratory animals (e.g., mouse, rabbit, rat, guinea pig, etc.).

The terms "control levels" or "control cells" are defined as the standard by which a change is measured, for example, the controls are not subjected to the experiment, but are instead subjected to a defined set of parameters, or the controls are based on pre- or post-treatment levels.

By "contacting" is meant an instance of exposure by close physical contact of at least one substance to another substance. For example, contacting can include contacting a substance, such as a pharmacologic agent, with a cell. A cell can be contacted with a test compound, for example, a cytidine deaminase inhibitor, or putative cytidine deaminase inhibitor by adding the agent to the culture medium (by continuous infusion, by bolus delivery, or by changing the medium to a medium that contains the agent) or by adding the agent to the extracellular fluid in vivo (by local delivery, systemic delivery, intravenous injection, bolus delivery, or continuous infusion). The duration of contact with a cell or group of cells is determined by the time the test compound is present at physiologically effective levels or at presumed physiologically effective levels in the medium or extracellular fluid bathing the cell.

"Treatment" or "treating" means to administer a composition to a subject or a system with an undesired condition or at risk for the condition. The condition can include a disease or a predisposition to a disease. The effect of the administration of the composition to the subject can have the effect of but is not limited to reducing or preventing the symptoms of the condition, a reduction in the severity of the condition, or the complete ablation of the condition.

By "effective amount" is meant a therapeutic amount needed to achieve the desired result or results, e.g., inhibiting editing of nucleic acids, interrupting selective cytidine deaminase activity, reducing viral production or infectivity, inhibiting class switch recombination, inhibiting somatic hypermutation, enhancing or blunting physiological functions, enhancing viral vector therapy, altering the qualitative or quantitative nature of the proteins expressed by cell or tissues, and eliminating or reducing disease causing molecules and/or the mRNA or DNA that encodes them, etc.

Herein, "inhibition" or "suppression" means to reduce activity as compared to a control (e.g., basal activity in the absence of such inhibition). It is understood that inhibition or suppression can mean a slight reduction in activity to the complete ablation of all activity. An "inhibitor" or "suppressor" can be anything that reduces the targeted activity. For example, suppression of CEM15 by a cytidine deaminase inhibitor can be determined by assaying the amount of CEM15 activity in the presence of the cytidine deaminase inhibitor to the amount of CEM15 activity in the absence of the cytidine deaminase inhibitor. In this example, if the amount of CEM15 activity is decreased in the presence of the context dependent inhibitor as compared to the amount of CEM15 activity in the absence of the context dependent inhibitor, the cytidine deaminase inhibitor can be said to suppress CEM15 activity.

Methods disclosed herein may refer to "systems." It is understood that systems can be, for example, cells, columns, or batch processing containers (e.g., culture plates). A system is a set of components, any set of components that allows for the steps of the method to performed. Typically a system will comprise one or more components, such as a protein(s) or reagent(s). One type of system disclosed would be a cell that comprises both a cytidine deaminase and a cytidine deaminase inhibitor, for example. Another type of system would be one that comprises a cell (e.g., a cancer cell). A third type of system might be a chromatography column that has CEM15, AID, or other deaminase or putative deaminase, bound to the column.

"Context dependent inhibitor" or cytidine deaminase inhibitor means any inhibitor found within the context of a polymeric substrate that has a targeting function. The polymeric substrate can be a nucleic acid, but it is not limited to such molecules.

A "cytidine deaminase-positive cell" means any cell that expresses one or more cytidine deaminases or deoxycytidine deaminases. Such expression can be naturally occurring or the cell can include an exogenous nucleic acid that encodes one or more selected deaminases.

By "polymeric substrate" is meant a nucleic acid sequence into which the cytidine deaminase inhibitor has been incorporated. The polymeric substrate of the cytidine deaminase inhibitor can comprise an oligonucleotide or a polynucleotide, for example. The nucleic acid sequence can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 or more residues in length. Also, the nucleic acid sequence can be an RNA or a DNA sequence, can comprise naturally occurring or nonnaturally occurring nucleotides, and can comprise double or single stranded sequences. A double stranded sequence can comprise a single stranded region such as a replication bubble, but is not limited to such duplex structures. Double-stranded need not imply Watson-Crick base pairing interactions as the sole feature that holds the two-stranded molecule together (e.g. there can be non-base-paired as well as base paired regions etc).

Variables such as $R^1$-$R^{10}$, W, $X^1$, $X^2$, Y, and Z used throughout the application are the same variables as previously defined unless stated to the contrary.

The term "alkyl group" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "alkenyl group" is defined as a hydrocarbon group of 2 to 24 carbon atoms and structural formula containing at least one carbon-carbon double bond.

The term "alkynyl group" is defined as a hydrocarbon group of 2 to 24 carbon atoms and a structural formula containing at least one carbon-carbon triple bond.

The term "halogenated alkyl group" is defined as an alkyl, alkenyl, or alkynyl group as defined above with one or more hydrogen atoms present on these groups substituted with a halogen (F, Cl, Br, I).

The term "cycloalkyl group" is defined as a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorous.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "aralkyl" is defined as an aryl group having an alkyl, alkynyl, or alkenyl group as defined above attached to the aromatic group. An example of an aralkyl group is a benzyl group.

The term "amine group" is represented by the formula —NRR', where R and R' can be, independently, hydrogen, an alkyl, alkenyl, alkynyl, aryl, aralkyl, cycloalkyl, halogenated alkyl, or heterocycloalkyl group described above.

The term "amide group" is represented by the formula —C(O)NRR', where R and R' can be hydrogen, an alkyl, alkenyl, alkynyl, aryl, aralkyl, cycloalkyl, halogenated alkyl, or heterocycloalkyl group described above.

The term "ester" is represented by the formula —OC(O)R, where R can be an alkyl, alkenyl, alkynyl, aryl, aralkyl, cycloalkyl, halogenated alkyl, or heterocycloalkyl group described above.

The term "hydroxyl group" is represented by the formula —OH. The term "alkoxy group" is represented by the formula —OR, where R can be an alkyl, alkenyl, alkynyl, aryl, aralkyl, cycloalkyl, halogenated alkyl, or heterocycloalkyl group described above.

The term "aldehyde" is represented by the formula —C(O)H.

The term "keto group" is represented by the formula —C(O)R, where R is an alkyl, alkenyl, alkynyl, aryl, aralkyl, cycloalkyl, halogenated alkyl, or heterocycloalkyl group described above.

The term "acyl" is represented by the formula —OC(O)R, where R is hydrogen, an alkyl, alkenyl, alkynyl, aryl, aralkyl, cycloalkyl, halogenated alkyl, or heterocycloalkyl group described above.

The term "sulfone" is represented by the formula —S(O)$_2$R, where R is hydrogen, an alkyl, alkenyl, alkynyl, aryl, aralkyl, cycloalkyl, halogenated alkyl, or heterocycloalkyl group described above.

The term "halo" is defined as F, Cl, Br, or I.

The term "monophosphate" (or monophosphoryl) is represented by the formula (RO)$_2$(O)PO—, where each R can be, independently, hydrogen, an alkyl, alkenyl, alkynyl, aryl, aralkyl, cycloalkyl, halogenated alkyl, heterocycloalkyl group as described above, or the salt thereof.

The term "diphosphate" (or diphosphoryl) is a double phosphoanhydride bond represented by the formula (RO)$_2$(O)P—O—P(O)(OR)O—, where each R can be, independently, hydrogen, an alkyl, alkenyl, alkynyl, aryl, aralkyl, cycloalkyl, halogenated alkyl, heterocycloalkyl group as described above, or the salt thereof.

The term "triphosphate" (or triphosphoryl) is a triple phosphoanhydride bond represented by the formula (RO)$_2$(O)P—O—P(O)(OR)O—P(O)(OR)O—, where each R can be, independently, hydrogen, an alkyl, alkenyl, alkynyl, aryl, aralkyl, cycloalkyl, halogenated alkyl, heterocycloalkyl group as described above, or the salt thereof.

The term "phosphorothioate" is a P—S bond represented by the formula (RO)$_2$(SR)PO—, where S is a sulfur (and can be a thiolate), and each R can be, independently, hydrogen, an alkyl, alkenyl, alkynyl, aryl, aralkyl, cycloalkyl, halogenated alkyl, heterocycloalkyl group as described above, or the salt thereof.

The term "phosphoroamidate" is a P—N bond represented by the formula (RO)$_2$(NRR')PO—, where each R and R' can be, independently, hydrogen, an alkyl, alkenyl, alkynyl, aryl, aralkyl, cycloalkyl, halogenated alkyl, heterocycloalkyl group as described above, or the salt thereof.

The term "phosphonate" is a P—C bond represented by the formula (RO)$_2$(CRR')PO—, where each R and R' can be, independently, hydrogen, an alkyl, alkenyl, alkynyl, aryl, aralkyl, cycloalkyl, halogenated alkyl, heterocycloalkyl group as described above, or the salt thereof.

A 2'-5' (2'-to-5') phosphodiester linkage is a phosphoanhydride linkage between the 2'-oxygen of the nucleotide ribose sugar and the 5'-phosphorus of the flanking nucleotide. This bond is chemically distant from the typical 3'-5' phosphodiester bond observed in cellular (natural) DNA or RNA synthesis via polymerase enzymes. The linkage is resistant to cellular degradation enzymes.

$R^1$-$R^{10}$, W, $X^1$, $X^2$, Y, and Z can, independently, possess two or more of the groups listed above. For example, if $R^1$ is a straight chain alkyl group, one of the hydrogen atoms of the alkyl group can be substituted with a hydroxyl group, an alkoxy group, etc. Depending upon the groups that are selected, a first group may be incorporated within second group or, alternatively, the first group may be pendant (i.e., attached) to the second group. For example, with the phrase "an alkyl group comprising an ester group," the ester group may be incorporated within the backbone of alkyl group. Alternatively, the ester can be attached to the backbone of the alkyl group. The nature of the group(s) that is (are) selected will determine if the first group is embedded or attached to the second group.

Disclosed are compounds, compositions, and components that can be used for, can be used in conjunction with, can be used in preparation of, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a number of different nucleosides and polymeric substrates are disclosed and discussed, each and every combination and permutation of the nucleoside and the polymeric substrate are specifically contemplated unless specifically indicated to the contrary. Thus, if a class of molecules A, B, and C are disclosed as well as a class of molecules D, E, and F, and an example of a combination molecule, A-D is disclosed, then even if each is not individually recited, each is individually and collectively contemplated. Thus, in this example, each of the combinations A-E, A-F, B-D, B-E, B-F, C-D, C-E, and C—F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Compounds and Compositions

Cytidine deaminases are a class of enzymes involved in pyrimidine metabolism. The mechanism for cytidine deaminase activity involves nucleophilic attack at the C4 position of the cytosine ring by water coordinated to $Zn^{2+}$, where the zinc ion is bound to the enzyme. Thus, any nucleoside susceptible to nucleophilic attack or one that mimics the tetrahedral $sp^3$ geometry of the intermediate (but need not be chemically reactive) can be used in any of the methods described herein as a component of a cytidine deaminase inhibitor. In one aspect, one or more cytidine deaminase inhibitors can be used in the polymeric substrate to inhibit cytidine deaminases.

The C4 position of cytosine is a $sp^2$ carbon center, which is susceptible to nucleophilic attack by the enzyme. In one aspect, the cytidine deaminase inhibitor used herein is a nucleoside comprising a $sp^2$ carbon center susceptible to nucleophilic attack giving rise to the enzyme's preferred $sp^3$ intermediate. Methods for making a compound susceptible to nucleophilic attack and those whose geometry are preferred by the enzyme are known in the art. For example, attaching an electron-withdrawing group on the atom where nucleophilic attack is desired can be performed. As used herein, the term "electron-withdrawing group" is defined as any group that makes a compound more susceptible to nucleophilic when compared to the same compound that does not contain the electron-withdrawing group. In one aspect, the cytidine deaminase inhibitor is a nucleoside comprising a $sp^2$ carbon center with an electron-withdrawing group attached to the $sp^2$ carbon center. Examples of electron-withdrawing groups include, but are not limited to, a nitro group, a cyano group, an ester group, an aldehyde group, a keto group, a sulfone group, a carbonyl group, an imino group, an alkenyl, an amide group, a hydroxyl group, or a combination thereof. Two or more electron-withdrawing groups can be used in combination with one another. For example, the electron-withdrawing group can be an enol represented by the formula —C=C—OH, which is composed of an alkenyl group and a hydroxyl group. In this example, the enol can tautomerize to the corresponding keto compound —HC—C(O).

As described above, in one aspect, the cytidine deaminase inhibitor of cytidine deaminases described herein are susceptible to nucleophilic attack. In one aspect, the Cytidine deaminase inhibitor of cytidine deaminases are susceptible to nucleophilic attack by a metal-bound hydroxide such as, for example, zinc hydroxide.

In one aspect, the cytidine deaminase inhibitor of cytidine deaminases (or its family members the adenosine deaminases acting on RNA or ADARs, including those with activity on mRNA, tRNA or rRNA) used herein comprise a purine or pyrimidine. The terms "purine" and "pyrimidine" include any natural and non-natural purines and pyrimidines. When the Cytidine deaminase inhibitor of cytidine deaminases comprise a pyrimidine, nucleophilic attack can occur at the C4 position by the cytidine deaminase. Likewise, when the cytidine deaminase inhibitor of cytidine deaminases comprise a purine, nucleophilic attack can occur at the C6 position of the purine by the cytidine deaminase. In order to enhance nucleophilic attack at these positions, one or more electron-withdrawing groups can be placed at the C4 position of the pyrimidine or C6 position of the purine. However, the cytidine deaminase inhibitor can function by simply mimicking the sp3 intermediate at the C4 or C6 positions of pyrimidine or purine bases.

In one aspect, any of the nucleosides described herein are provided as the indicated enantiomer and substantially in the absence of its corresponding enantiomer (i.e., in enantiomerically enriched form). As used herein, the term "enantiomerically pure" refers to a nucleoside composition that includes at least approximately 95%, and preferably approximately 97%, 98%, 99%, or 100% of a single enantiomer of that nucleoside. In one aspect, the nucleoside is the naturally occurring D-enantiomer or the L-enantiomer.

In one aspect, the cytidine deaminase inhibitor of cytidine deaminases includes a nucleoside having the formula I or II

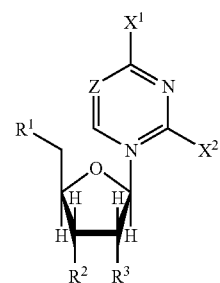

I

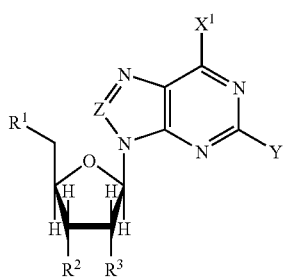

II wherein
R$^1$, R$^2$, and R$^3$ can be, independently, hydrogen, hydroxyl, alkoxy, halo, alkyl, acyl, aryl, aralkyl, monophosphate, diphosphate, triphosphate, phosphorothioate, phosphoramidate, phosphonate, or a 2'-5' phosphodiester linkage, N$_3$, NR$^4$R$^5$, NO$_2$, NOR$^6$, CN, —C(O)NH$_2$, SH, —S-alkyl, —S-aryl, Se-alkyl, Se-aryl, or a residue of the polymeric substrate, wherein at least one of R$^2$ or R$^3$ is hydroxyl;

X$^1$, X$^2$, and Y can be, independently, hydrogen, hydroxyl, alkoxy, alkyl, acyl, aryl, aralkyl, NR$^4$R$^5$, or an electron-withdrawing group;

wherein R$^4$, R$^5$, and R$^6$ can be, independently, alkyl, aryl, aralkyl, alkaryl, acyl, or hydrogen; and Z can be nitrogen or CR$^7$, wherein R$^7$ is hydrogen, hydroxyl, alkoxy, halo, alkyl, acyl, aryl, or aralkyl.

Any of the Cytidine deaminase inhibitors described herein can be incorporated in the polymeric substrate. By "incorporated into" is meant bracketed by (1) the polymeric substrate, (2) at either terminus (e.g. 5' or 3') of the polymeric substrate, or (3) a combination thereof. In one aspect, when the context-dependent cytidine deaminase inhibitor having the formula I or II is bracketed by the polymeric substrate, R$^1$ and R$^2$ are a residue of the polymeric substrate. In another aspect, when the cytidine deaminase inhibitor having the formula I or II is the terminus of the polymeric substrate, R$^1$ or R$^2$ is a residue of the polymeric substrate. The term "residue" as used in the specification and claims, refers to any moiety of the polymeric substrate including the moiety attached to any of the nucleosides described herein after the nucleoside has been incorporated (e.g., within the polymeric substrate or at the terminus or both) into the polymeric substrate.

In one aspect, X in formulae I and II is any of the electron-withdrawing groups described above. In one aspect, when the nucleoside is formula I, R$^2$ is hydroxyl and R$^3$ can be hydroxyl, halo, or alkoxy. In another aspect, when the nucleoside has the formula I, X$^1$ can be halo such as fluoro, chloro, bromo, or iodo, and X$^2$ is hydroxyl. In a further aspect, when the nucleoside is I, Z is CH. The nucleoside having the formula I can have any combination of these aspects.

In another aspect, when the nucleoside has formula II, R$^2$ is hydroxyl and R$^3$ can be hydroxyl, halo, or alkoxy. In a further aspect, when the nucleoside has the formula II, X$^1$ can be hydrogen, hydroxyl, or NR$^4$R$^5$. In another aspect, when the nucleoside has the formula II, Y is hydrogen. In yet another aspect, when the nucleoside has the formula II, Z can be nitrogen or CR$^7$, wherein R$^7$ can be hydrogen or hydroxyl. When R$^7$ is hydroxyl, the resulting enol can tautomerize to the keto form. The nucleoside having the formula II can have any combination of these aspects.

In another aspect, any of the nucleosides described herein has at least one group capable of hydrogen bonding in a manner similar to cytosine or uracil. In one aspect, R$^2$ and/or R$^3$ in formulae I-VII, where formulae III-VII are discussed below, is a hydroxyl group. Nucleosides having at least one group capable of hydrogen bonding increases the nucleoside's affinity for the cytidine deaminase.

Mechanistic studies have indicated that cytidine deaminases exhibit greater affinity for the tetrahedral intermediate (sp$^3$) than the corresponding s center prior to nucleophilic attack. In one aspect, the nucleosides described herein have at least one stable sp center that mimics the intermediate at C4 or C6 of pyrimidine or purine. In a related aspect, a compound such as cacodylic acid also known as dimethyl arsenic acid ((CH$_3$)$_2$—As—O$_2$H) mimics the sp$^3$ geometry and can serve as a cytidine deaminase inhibitor as long as it is tethered to the flanking sequences at 5' and 3' termini. The group at C4 need not be carbon, and can be replaced by As in the latter instance. In another aspect, the nucleoside has at least one sp$^3$ carbon center, wherein the sp$^3$ carbon center has at least one —WR group, wherein W is O, S, Se, or NR, wherein R is hydrogen, alkyl, aryl, aralkyl, alkenyl, alkynyl, or acyl as described above. In a further aspect, when the nucleoside includes a pyrimidine or purine, the nucleoside comprises a sp$^3$ carbon center at C4 of the pyrimidine or C6 of the purine.

In one aspect, the cytidine deaminase inhibitor includes a nucleoside having the formula III or IV

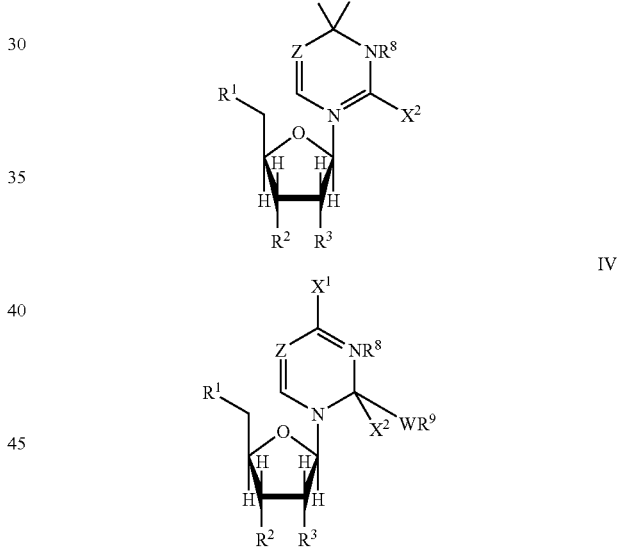

wherein
R$^1$, R$^2$, and R$^3$ can be, independently, hydrogen, hydroxyl, alkoxy, halo, alkyl, acyl, aryl, aralkyl, monophosphate, diphosphate, triphosphate, phosphorothioate, phosphoramidate, phosphonate, or a 2'-5' phosphodiester linkage, N$_3$, N$^4$R$^5$, NO$_2$, NOR$^6$, CN, —C(O)NH$_2$, SH, —S-alkyl, —S-aryl, Se-alkyl, Se-aryl, or a residue of the polymeric substrate, wherein at least one of R$^2$ or R$^3$ is hydroxyl;

X$^1$, X$^2$, and Y can be, independently, hydrogen, hydroxyl, alkoxy, alkyl, acyl, aryl, aralkyl, NR$^4$R$^5$, or an electron-withdrawing group;

W can be O, S, Se, or NR$^{10}$;

wherein R$^4$, R$^5$, R$^6$, R$^8$, R$^9$, and R$^{10}$ can be, independently, alkyl, aryl, aralkyl, alkaryl, acyl, or hydrogen; and Z can be nitrogen or CR$^7$, wherein R$^7$ is hydrogen, hydroxyl, alkoxy, halo, alkyl, acyl, aryl, or aralkyl.

In one aspect, $X^1$ and $X^2$ in formulae III and IV can be any of the electron-withdrawing groups described above. In one aspect, when the nucleoside is formula III, $R^2$ is hydroxyl and $R^3$ can be hydroxyl, halo, or alkoxy. In another aspect, when the nucleoside has the formulae III or IV, $X^1$ can be halo such as fluoro, chloro, bromo, or iodo, and $X^2$ is hydroxyl. In a further aspect, when the nucleoside is III, Z is CH. The nucleoside having the formulae III or IV can have any combination of these aspects.

Examples of nucleosides useful in the methods described herein include, but are not limited to, any of the phosphoramidites (distinct from phosphoramidates) manufactured by Glen Research Corporation. In one aspect, the nucleoside can be 5'-dimethoxytrityl-N-acetyl-2'-O-acetyl-cytisine arabinoside, 3'-[(2-cyanoethyl)-(N,N-diisopropyl)]-phosphoramidite 5'-dimethoxytrityl-N-benzoyl-adenosine, 2'-O-methyl-3'-[(2-cyanoethyl)-(N,N-diisopropyl)]-phosphoramidite 5'-dimethoxytrityl-N-benzoyl-cytidine, 2-'O-methyl-3'-[(2-cyanoethyl)-(N,N-diisopropyl)]-phosphoramidite 5'-dimethoxytrityl-N-acetyl-cytidine, 2-'O-methyl-3'-[(2-cyanoethyl)-(N,N-diisopropyl)]-phosphoramidite 5'-dimethoxytrityl-N-dimethylaminomethylidene-guanosine, 2'-O-methyl-3'-[(2-cyanoethyl)-(N,N-diisopropyl)]-phosphoramidite 5'-dimethoxytrityl-uridine, 2'-O-Me-3'-[(2-cyanoethyl)-(N,N-diisopropyl)]-phosphoramidite 5'-dimethoxytrityl-N-phenoxyacetyl-2'-adenosine, 2'-O-methyl-3'-[(2-cyanoethyl)-(N,N-diisopropyl)]-phosphoramidite 5'-dimethoxytrityl-N2-isopropylphenoxyacetyl-2'-O-methyl-guanosine, 3'-[(2-cyanoethyl)-(N,N-diisopropyl)]-phosphoramidite 5'-dimethoxytrityl-N-benzoyl-2'-adenosine, 2'-O-methyl-3'-succinoyl-long chain alkylamino-CPG 5'-dimethoxytrityl-N-benzoyl-2'-cytidine, 2'-O-methyl-3'-succinoyl-long chain alkylamino-CPG 5'-dimethoxytrityl-N-acetyl-cytidine, 2'-O-methyl-3'-succinoyl-long chain alkylamino-CPG 5'-dimethoxytrityl-N-dimethylformamidine-guanosine, 2'-O-methyl-3'-succinoyl-long chain alkylamino-CPG 5'-dimethoxytrityl-uridine, 2'-O-methyl-3'-succinoyl-long chain alkylamino-CPG N-(6-(O-dimethoxytrityl)-hexyl)-(2-carboxamide)-phthalimidyl-lcaa-CPG 5'-dimethoxytrityl-N-acetyl-adenosine, 2'-O-acetyl-3'-succinoyl-long chain alkylamino-CPG 5'-dimethoxytrityl-N-acetyl-cytidine, 2'-acetate-3'-succinoyl-long chain alkylamino-CPG 5'-dimethoxytrityl-N-acetyl-guanosine, 2'-O-acetyl-3'-succinoyl-long chain alkylamino-CPG 5'-dimethoxytrityl-inosine, 2'-O-triisopropylsilyloxymethyl-3'-[(2-cyanoethyl)-(N,N-diisopropyl)]-phosphoramidite 5'-dimethoxytrityl-4-(2-cyanoethylthio)-uridine, 2'-O-triisopropylsilyloxymethyl-3'-[(2-cyanoethyl)-(N,N-diisopropyl)]-phosphoramidite 5'-dimethoxytrityl-5-Methyl-uridine, 2'-O-triisopropylsilyloxymethyl-3'-[(2-cyanoethyl)-(N,N-diisopropyl)]-phosphoramidite 5'-dimethoxytrityl-N-acetyl-5-methyl-cytidine, 2'-O-triisopropylsilyloxymethyl-3'-[(2-cyanoethyl)-(N,N-diisopropyl)]-phosphoramidite 5'-dimethoxytrityl-N-acetyl-2'-deoxypurineriboside, 2'-O-triisopropylsilyloxymethyl-3'-[(2-cyanoethyl)-(N,N-diisopropyl)]-phosphoramidite 5'-dimethoxytrityl-N2-(diacetyl)-2,6-diaminopurineriboside, 2'-O-triisopropylsilyloxymethyl-3'-[(2-cyanoethyl)-(N,N-diisopropyl)]-phosphoramidite 5'-dimethoxytrityl-5-bromo-uridine, 2'-O-triisopropylsilyloxymethyl-3'-[(2-cyanoethyl)-(N,N-diisopropyl)]-phosphoramidite 5'-dimethoxytrityl-5-iodo-uridine, 2'-O-triisopropylsilyloxymethyl-3'-[(2-cyanoethyl)-(N,N-diisopropyl)]-phosphoramidite 5'-dimethoxytrityl-[6-methyl-pyrrolo-[2,3-d]-pyrimidine-2 (3H)-one]-2'-O-triisopropylsilyloxymethyl-3'-[(2-cyanoethyl)-(N,N-diisopropyl)]-phosphoramidite 5'-O-methyl-2'-deoxythymidine, 3'-[(2-cyanoethyl)-(N,N-diisopropyl)]-phosphoramidite 5'-monomethoxytritylamino-2'-deoxythymidine, 3'-[(2-cyanoethyl)-(N,N-diisopropyl)]-phosphoramidite 5'-dimethoxytrityl-N-benzoyl-3'-deoxyadenosine, 2'-succinoyl-long chain alkylamino-CPG 5'-dimethoxytrityl-N-benzoyl-3'-deoxycytosine, 2'-succinoyl-long chain alkylamino-CPG 500

5'-dimethoxytrityl-N-dimethylformamidine-3'-deoxyguanosine, 2'-succinoyl-long chain alkylamino-CPG 5'-dimethoxytrityl-3'-deoxythymidine, 2'-succinoyl-long chain alkylamino-CPG 5'-dimethoxytrityl-N-succinoyl-long chain alkylamino-CPG, 2',3'-deoxyCytosine N6-diisobutylaminomethylidene-2',3'-dideoxyadenosine, 5'-[(2-cyanoethyl)-(N,N-diisopropyl)]-phosphoramidite N4-diisobutylaminomethylidene-2',3'-dideoxycytidine, 5'-[(2-cyanoethyl)-(N,N-diisopropyl)]-phosphoramidite N2-dimethylaminomethylidene-2',3'-dideoxyguanosine, 5'-[(2-cyanoethyl)-(N,N-diisopropyl)]-phosphoramidite 2',3'-dideoxythymidine, 5'-[(2-cyanoethyl)-(N,N-diisopropyl)]-phosphoramidite 5'-dimethoxytrityl-N-phenoxyacetyl-2'-deoxyadenosine, 3'-[(2-cyanoethyl)-(N,N-diisopropyl)]-phosphoramidite 5'-dimethoxytrityl-N-acetyl-2'-deoxycytidine, 3'-[(2-cyanoethyl)-(N,N-diisopropyl)]-phosphoramidite 5'-dimethoxytrityl-N-p-isopropyl-phenoxyacetyl-deoxyguanosine, 3'-[(2-cyanoethyl)-(N,N-diisopropyl)]-phosphoramidite 5'-dimethoxytrityl-N-benzoyl-5-methyl-2'-deoxycytidine, 2'-succinoyl-long chain alkylamino-CPG 500

5'-dimethoxytrityl-N2,N6-bis(diisobutylaminomethylidene)-2,6-diamino-2'-deoxypurineriboside-3'-[(2-cyanoethyl)-(N,N-diisopropyl)]-phosphoramidite 5'-dimethoxytrityl-N4-ethyl-2'-deoxycytidine, 3'-[(2-cyanoethyl)-(N,N-diisopropyl)]-phosphoramidite 5'-dimethoxytrityl-N-benzoyl-2'-deoxyadenosine, 3'-[(methyl)-(N,N-diisopropyl)]-phosphonamidite 5'-dimethoxytrityl-N-isobutyryl-2'-deoxycytidine, 3'-[(methyl)-(N,N-diisopropyl)]-phosphonamidite 5'-dimethoxytrityl-N4-acetyl-2'-deoxycytidine, 3'-[(methyl)-(N,N-diisopropyl)]phosphonamidite 5'-dimethoxytrityl-N-isobutyryl-2'-deoxyguanosine, 3'-[(methyl)-(N,N-diisopropyl)]-phosphonamidite 5'-dimethoxytrityl-2'-deoxythymidine, 3'-[(methyl)-(N,N-diisopropyl)]-phosphonamidite 5'-dimethoxytrityl-N-phenoxyacetyl-2'-deoxyadenosine, 3'-[methyl-(N,N-diisopropyl)]-phosphoramidite 5'-dimethoxytrityl-N-acetyl-2'-deoxycytidine, 3'-[methyl-(N,N-diisopropyl)]-phosphoramidite 5'-dimethoxytrityl-N-p-isopropyl-phenoxyacetyl-guanosine, 3'-[methyl-(N,N-diisopropyl)]-phosphoramidite 5'-dimethoxytrityl-2'-deoxythymidine, 3'-[(O-methyl)-(N,N-diisopropyl)]-phosphoramidite 5'-dimethoxytrityl-N-benzoyl-2'-deoxyadenosine, 3'-H-phosphonate, TEA salt 5'-dimethoxytrityl-N-benzoyl-2'-deoxycytidine, 3'-H-phosphonate, DBU salt 5'-dimethoxytrityl-N-isobutyryl-2'-deoxyguanosine, 3'-H-phosphonate, TEA salt 5'-dimethoxytrityl-2'-deoxythymidine, 3'-H-phosphonate, TEA salt 5'-Dimethoxytrityl-5-methyl-pyrimidin-2-one-2'-deoxyriboside, 3'-[(2-cyanoethyl)-(N,N-diisopropyl)]-phosphoramidite (5-Me-2'-deoxyZebularine)

5'-Dimethoxytrityl-2'-deoxyNebularine, 3'-[(2-cyanoethyl)-(N,N-diisopropyl)]-phosphoramidite (5-Me-2'-deoxyNebularine)

5'-Dimethoxytrityl-N-acetyl-deoxyCytidine, 2'-fluoro-3'-[(2-cyanoethyl)-(N,N-diisopropyl)]-phosphoramidite 5'-Dimethoxytrityl-deoxyUridine, 2'-fluoro-3'-[(2-cyanoethyl)-(N,N-diisopropyl)]-phosphoramidite 5'-Dimethoxytrityl-Uridine, 2'-methylseleno-3'-[(2-cyanoethyl)-(N,N-diisopropyl)]-phosphoramidite 5'-Dimethoxytrityl-N-benzoyl-3'-deoxyAdenosine, 2'-[(2-cyanoethyl)-(N,N-diisopropyl)]-phosphoramidite 5'-Dimethoxytrityl-N-benzoyl-3'-deoxyCytidine, 3'-[(2-cyanoethyl)-(N,N-diisopropyl)]-phosphoramidite 5'-Dimethoxytrityl-N-dimethylformamidine-3'-deoxyGuanosine, 3'-[(2-cyanoethyl)-(N,N-diisopropyl)]-phosphoramidite 5'-Dimethoxytrityl-3'-deoxyThymidine, 2'-[(2-cyanoethyl)-(N,N-diisopropyl)]-phosphoramidite 5'-Dimethoxytrityl-N-acetyl-2'-O-acetyl-Cytisine Arabinoside, 3'-[(2-cyanoethyl)-(N,N-diisopropyl)]-phosphoramidite In another aspect, the nucleoside can be zebularine, 5-methylzebularine, 4-fluorozebularine, 2'-deoxy, 2'-fluorozebularine, nebularine, 8-azanebularine, coformycin, 3,4,5,6-tetrahydro-2'-deoxyuridine, 5-fluorozebularine, diazepinone riboside, or inosine.

Also described herein are nucleosides that, when incorporated into a polymeric substrate, can facilitate the inhibition of cytidine deaminases. In one aspect, nucleoside has the formula V

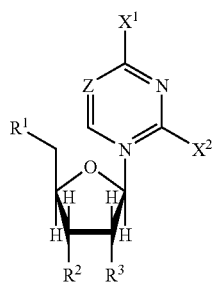

V wherein $R^1$, $R^2$, and $R^3$ can be, independently, hydrogen, hydroxyl, alkoxy, halo, alkyl, acyl, aryl, aralkyl, monophosphate, diphosphate, triphosphate, phosphorothioate, phosphoramidate, phosphonate, or a 2'-5' phosphodiester linkage, $N_3$, $NR^4R^5$, $NO_2$, $NOR^6$, CN, —C(O)NH$_2$, SH, —S-alkyl, —S-aryl, Se-alkyl, or Se-aryl, wherein at least one of $R^2$ or $R^3$ is hydroxyl;

wherein $R^4$, $R^5$, and $R^6$ can be, independently, alkyl, aryl, aralkyl, alkaryl, acyl, or hydrogen;

$X^1$ and $X^2$ can be electron-withdrawing groups, and

Z can be nitrogen or $CR^7$, wherein $R^7$ can be hydrogen, hydroxyl, alkoxy, halo, alkyl, acyl, aryl, or aralkyl, wherein the nucleoside is not uracil, thymine, cytosine, zebularine.

Any of the electron-withdrawing groups described above can be used in formula V. In one aspect, $X^1$ and $X^2$ can be a nitro group, a halo group such as fluoro, chloro, bromo, or iodo, a cyano group, an ester group, an aldehyde group, a keto group, a sulfone group, an amide group, an imino group, an alkenyl group, a hydroxyl group, or a combination thereof. In another aspect, $R^1$ and $R^2$ are hydroxyl, and $R^3$ can be hydroxyl, halo, or alkoxy. In a further aspect, Z is CH. The nucleoside having the formula V can have any combination of these aspects. In one aspect, the nucleoside having the formula V is 4-fluorozebularine or 2'-deoxy, 2'-fluorozebularine.

In another aspect, the nucleoside has the formula VI or VII

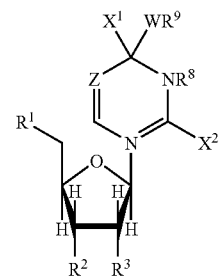

VI

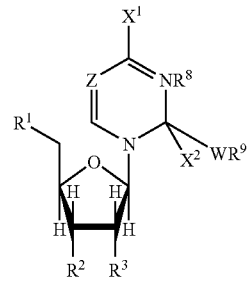

VII wherein $R^1$, $R^2$, and $R^3$ can be, independently, hydrogen, hydroxyl, alkoxy, halo, alkyl, acyl, aryl, aralkyl, monophosphate, diphosphate, triphosphate, phosphorothioate, phosphoramidate, phosphonate, or a 2'-5' phosphodiester linkage, $N_3$, $NR^4R^5$, $NO_2$, $NOR^6$, CN, —C(O)NH$_2$, SH, —S-alkyl, —S-aryl, Se-alkyl, or Se-aryl, wherein at least one of $R^2$ or $R^3$ is hydroxyl;

$X^1$ and $X^2$ can be electron-withdrawing groups;

W can be O, S, Se, or $NR^{10}$;

wherein $R^4$, $R^5$, $R^6$, $R^8$, $R^9$, and $R^{10}$ can be, independently, alkyl, aryl, aralkyl, alkaryl, acyl, or hydrogen; and Z can be nitrogen or $CR^7$, wherein $R^7$ can be hydrogen, hydroxyl, alkoxy, halo, alkyl, acyl, aryl, or aralkyl.

The nucleosides having the formulas VI and VII can be readily prepared by reacting nucleosides having the formula I with a nucleophile. For example, a nucleoside having the formula I can be reacted with an alcohol ($R^{10}$OH) or alkoxide ($R^{10}O^-$) to produce a nucleoside having the formula VI or VII. In one aspect, $X^1$ and $X^2$ in formulae VI and VII can be any of the electron-withdrawing groups described above. In one aspect, when the nucleoside is formula VI or VII, $R^2$ is hydroxyl and $R^3$ can be hydroxyl, halo, or alkoxy. In another aspect, when the nucleoside has the formula VI or VII, $X^1$ or $X^2$ can be halo such as fluoro, chloro, bromo, or iodo. In a further aspect, when the nucleoside is VI or VII, Z is CH. The nucleoside having the formula VI or VII can have any combination of these aspects.

Disclosed are cytidine deaminase inhibitors that can comprise a nucleoside as described above, incorporated in a polymeric substrate, wherein the polymeric substrate targets a cytidine deaminase. The polymeric substrate can comprise an oligonucleotide or a polynucleotide, and can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 or more residues in length. Particularly, the nucleic acid residues can comprise up to about 18 residues.

The nucleic acids of the cytidine deaminase inhibitor can be any length, particularly from about 2 to about 1000 residues, or any amount in between, from about 5 to about 500 residues, from about 10 to about 100 residues, or from about 15 to about 50 residues, or in particular about 18-20 residues. Large oligos can be made from smaller pieces joined together by 5'-I to 3'-phosphorothioate ligation as described by Y. Z. Xu and E. T. Kool, Tetrahedron Lett., 1997, 38, 5595-5598, herein incorporated in its entirety by reference.

The nucleic acids of the cytidine deaminase inhibitor can comprise RNA residues from a single stranded RNA, a double stranded RNA, or a single stranded replication bubble. Alternatively, the nucleic acids also comprise DNA residues. The DNA residues can form a single stranded DNA, a double stranded DNA, or a single stranded replication bubble. Furthermore, the nucleic acids of the cytidine deaminase inhibitor can comprise stretches of RNA and DNA alternating on the same strand of a single stranded oligonucleotide, or on double strands. Furthermore, in a double stranded oligonucleotide, one strand can comprise RNA, while the other comprises DNA.

Optimally, the targeted cytidine deaminase can be APOBEC-1, which is encoded by the following nucleic acid sequence:

```
                                              (SEQ ID NO: 2)
gatcccagag gaggaagtcc agagacagag caccatgact tctgagaaag gagaagaatc gaaccctggg agtttgacgt cttctatgac cccagagaac ttcgtaaaga ggcctgtctg ctctacgaaa tcaagtgggg catgagccgg aagatctggc gaagctcagg caaaaacacc accaatcacg tggaagttaa ttttataaaa aaatttacgt cagaaagaga ttttcaccca tccatcagct gctccatcac ctggttcttg tcctggagtc cctgctggga atgctcccag gctattagag agtttctgag tcggcaccct ggtgtgactc tagtgatcta cgtagctcgg ctttttggc acatggatca acaaatcgg caaggtctca gggaccttgt taacagtgga gtaactattc agattatgag agcatcagag tattatcact gctggaggaa ttttgtcaac tacccacctg gggatgaagc tcactggcca caatacccac ctctgtggat gatgttgtac gcactggagc tgcactgcat aattctaagt cttccaccct gtttaaagat ttcaagaaga
```

```
                                              -continued
tggcaaaatc atcttacatt tttcagactt catcttcaaa actgccatta ccaaacgatt ccgccacaca tccttttagc tacagggctg atacatcctt ctgtggcttg gagatgaata ggatgattcc gtgtgtgtac tgattcaaga acaagcaatg atgacccact aaagagtgaa tgccatttag aatctagaaa tgttcacaag gtacccaaa actctgtagc ttaaaccaac aataaatatg tattacctct ggc
```

The targeted cytidine deaminase of the cytidine deaminase inhibitor can also be an APOBEC-related protein, such as AID. The full length nucleic acid sequence that encodes AID is:

```
                                              (SEQ ID NO: 6)
atggacagcc tcttgatgaa ccggaggaag tttctttacc aattcaaaaa tgtccgctgg gctaagggtc ggcgtgagac ctacctgtgc tacgtagtga agaggcgtga cagtgctaca tcctttcac tggactttgg ttatcttcgc aataagaacg gctgccacgt ggaattgctc ttcctccgct acatctcgga ctgggaccta gaccctggcc gctgctaccg cgtcacctgg ttcacctcct ggagcccctg ctacgactgt gcccgacatg tggccgactt tctgcgaggg aaccccaacc tcagtctgag gatcttcacc gcgcgcctct acttctgtga ggaccgcaag gctgagcccg aggggctgcg gcggctgcac cgcgccgggg tgcaaatagc catcatgacc ttcaaagatt attttactg ctggaatact tttgtagaaa accatgaaag aactttcaaa gcctgggaag ggctgcatga aaattcagtt cgtctctcca gacagcttcg gcgcatcctt ttgcccctgt atgaggttga tgacttacga gacgcatttc gtactttggg actttga
```

The cytidine deaminase inhibitor for AID can comprise WRZY (SEQ ID NO: 7), wherein W is A or T, wherein R is a purine, wherein Z is the nucleoside, and wherein Y is a pyrimidine.

The cytidine deaminase inhibitor can also be directed towards CEM15. The full length nucleic acid that encodes CEM15 (APOBEC-3G) is represented by:

```
                                              (SEQ ID NO: 10)
ctgccaggggagggcccagagaaaaccagaaagagggtgagagactga ggaagataaagcgtcccagggcctcctacaccagcgcctgagcaggaagc gggaggggccatgactacgaggccctgggaggtcactttagggagggctg tcctaaaaccagaagcttggagcagaaagtgaaaccctggtgctccagac aaagatcttagtcgggactagccggccaaggatgaagcctcacttcagaa acacagtggagcgaatgtatcgagacacattctcctacaactttttataat agacccatcctttctcgtcggaataccgtctggctgtgctacgaagtgaa aacaaagggtccctcaaggccccctttggacgcaaagatctttcgaggcc
``` aggtgtattccgaacttaagtaccacccagagatgagattcttccactgg ttcagcaagtggaggaagctgcatcgtgaccaggagtatgaggtcacctg gtacatatcctggagccctgcacaaagtgtacaagggatatggccacgt tcctggccgaggacccgaaggttaccctgaccatcttcgttgcccgcctc tactacttctgggacccagattaccaggaggcgcttcgcagcctgtgtca gaaaagagacggtccgcgtgccaccatgaagatcatgaattatgacgaat ttcagcactgttggagcaagttcgtgtacagccaaagagagctatttgag ccttggaataatctgcctaaatattatatattactgcacatcatgctggg ggagattctcagacactcgatggatccacccacattcactttcaactta acaatgaaccttgggtcagaggacggcatgagacttacctgtgttatgag gtggagcgcatgcacaatgacacctgggtcctgctgaaccagcgcagggg cttttctatgcaaccaggctccacataaacacggtttccttgaaggccgcc atgcagagctgtgcttcctggacgtgattcccttttggaagctggacctg gaccaggactacaggggttacctgcttcacctcctggagcccctgcttcag ctgtgcccaggaaatggctaaattcatttcaaaaaacaaacacgtgagcc tgtgcatcttcactgcccgcatctatgatgatcaaggaagatgtcaggag gggctgcgcaccctggccgaggctggggccaaaatttcaataatgacata cagtgaatttaagcactgctgggacacctttgtggaccaccaggatgtc ccttccagccctgggatggactagatgagcacagccaagacctgagtggg aggctgcgggccattctccagaatcaggaaaactgaaggatgggcctcag tctctaaggaaggcagagacctgggttgagcctcagaataaaagatcttc ttccaagaaatgcaaacaggctgttcaccaccatctccagctgatcacag acaccagcaaagcaatgcactcctgaccaagtagattcttttaaaaatta gagtgcattactttgaatcaaaaatttattttatatttcaagaataaagta ctaagattgtgctcaatacacagaaaagtttcaaacctactaatccagcg acaatttgaatcggttttgtaggtagaggaataaaatgaaatactaaatc tttctgtaaaaaaaaaa Representative sequences recognized by CEM15 include first strand DNA or portions thereof, including ten or more sequences comprising those produced by reverse transcription from HIV-1:

(

-continued

```
cagtactggatgtgggtgatgcatattttttcagttcccttagatgaagac
ttcaggaagtatactgcatttaccataccctagtataaacaatgagacacc
agggattagatatcagtacaatgtgcttccacagggatggaaaggatcac
cagcaatattccaaagtagcatgacaaaaatcttagagccttttagaaaa
caaaatccagacatagttatctatcaatacatggatgatttgtatgtagg
atctgacttagaaatagggcagcatagaacaaaaatagaggagctgagac
aacatctgttgaggtggggacttaccacaccagacaaaaaacatcagaaa
gaacctccattcctttggatggggttatgaactccatcctgataaatggac
agtacagcctatagtgctgccagaaaaagacagctggactgtcaatgaca
tacagaagttagtgggaaaattgaattgggcaagtcagatttacccaggg
attaaagtaaggcaattatgtaaactccttagaggaaccaaagcactaac
agaagtaataccactaacagaagaagcagagctagaactggcagaaaaca
gagagattctaaaagaaccagtacatggagtgtattatgacccatcaaaa
gacttaatagcagaaatacagaagcaggggcaaggccaatggacatatca
aatttatcaagagccatttaaaaatctgaaaacaggaaaatatgcaagaa
cgaggggtgcccacactaatgatgtaaaacaattaacagaggcagtgcaa
aaaataaccacagaaagcatagtaatatggggaaagactcctaaattaa
actacccatacaaaaggaaacatgggaaacatggtggacagagtattggc
aagccacctggattcctgagtgggagtttgtcaatacccctcctttagtg
aaattatggtaccagttagagaaagaacccatagtaggagcagaaacgtt
ctatgtagatggggcagctagcagggagactaaattaggaaaagcaggat
atgttactaatagaggaagacaaaaagttgtcaccctaactgacacaaca
aatcagaagactgagttacaagcaattcatctagctttgcaggattcggg
attagaagtaaatatagtaacagactcacaatatgcattaggaatcattc
aagcacaaccagataaaagtgaatcagagttagtcaatcaaataatagag
cagttaataaaaaaggaaaaggtctatctggcatgggtaccagcacacaa
aggaattggaggaaatgaacaagtagataaaattagtcagtgctggaatca
ggaaagtactatttttagatggaatagataaggcccaagatgaacatgag
aaatatcacagtaattggagagcaatggctagtgattttaacctgccacc
tgtagtagcaaaagaaatagtagccagctgtgataaatgtcagctaaaag
gagaagccatgcatggacaagtagactgtagtccaggaatatggcaacta
gattgtacacatttagaaggaaaagttatcctggtagcagttcatgtagc
cagtggatatatagaagcagaagttattccagcagaaacagggcaggaaa
cagcatactttcttttaaaattagcaggaagatggccagtaaaaacaata
catacagacaatggcagcaatttcaccagtactacggttaaggccgcctg
ttggtgggcgggaatcaagcaggaatttggaattccctacaatccccaaa
gtcaaggagtagtagaatctatgaataaaagaattaaagaaaattataggc
caggtaagagatcaggctgaacatcttaagacagcagtacaaatggcagt
attcatccacaattttaaaagaaaaggggggattggggggtacagtgcag
gggaaagaatagtagacataatagcaacagacatacaaactaaagaatta
caaaaacaaattacaaaaattcaaaattttcgggtttattacagggacag cagagatccactttggaaaggaccagcaaagctcctctggaaaggtgaag
gggcagtagtaatacaagataatagtgacataaaagtagtgccaagaaga
aaagcaaagatcattagggattatggaaaacagatggcaggtgatgattg
tgtggcaagtagacaggatgaggattagaacatggaaaagtttagtaaaa
caccatatgtatgtttcagggaaagctaggggatggttttatagacatca
ctatgaaagccctcatccaagaataagttcagaagtacacatcccactag
gggatgctagattggtaataacaacatattggggtctgcatacaggagaa
agagactggcatctgggtcagggagtctccatagaatggaggaaaaagag
atatagcacacaagtagaccctgaactagcagaccaactaattcatctgt
attactttgactgttttttcagactctgctataagaaaggccttattagga
catatagttagccctaggtgtgaatatcaagcaggacataacaaggtagg
atctctacaatacttggcactagcagcattaataacaccaaaaaagataa
agccacctttgcctagtgttacgaaactgacagaggatagatggaacaag
ccccagaagaccaagggccacagagggagccacacaatgaatggacacta
gagcttttagaggagcttaagaatgaagctgttagacattttcctaggat
ttggctccatggcttagggcaacatatctatgaaacttatggggatactt
gggcaggagtggaagccataataagaattctgcaacaactgctgtttatc
catttcagaattgggtgtcgacatagcagaataggcgttactcaacagag
gagagcaagaaatggagccagtagatcctagactagagccctggaagcat
ccaggaagtcagcctaaaactgcttgtaccacttgctattgtaaaaagtg
ttgctttcattgccaagtttgtttcacaacaaaagccttaggcatctcct
atggcaggaagaagcggagacagcgacgaagacctcctcaaggcagtcag
actcatcaagtttctctatcaaagcagtaagtagtacatgtaatgcaacc
tatacaaatagcaatagcagcattagtagtagcaataataatagcaatag
ttgtgtggtccatagtaatcatagaatataggaaaatattaagacaaaga
aaaatagacaggttaattgatagactaatagaaagagcagaagacagtgg
caatgagagtgaaggagaaatatcagcacttgtggagatgggggtggaaa
tggggcaccatgctccttgggatattgatgatctgtagtgctacagaaaa
attgtgggtcacagtctattatggggtacctgtgtggaaggaagcaacca
ccactctattttgtgcatcagatgctaaagcatatgatacagaggtacat
aatgtttgggccacacatgcctgtgtacccacagaccccaacccacaaga
agtagtattggtaaatgtgacagaaaattttaacatgtggaaaaatgaca
tggtagaacagatgcatgaggatataatcagtttatgggatcaaagccta
aagccatgtgtaaaattaaccccactctgtgttagtttaaagtgcactga
tttggggaatgctactaataccaatagtagtaataccaatagtagtagcg
gggaaatgatgatggagaaaggagagataaaaaactgctctttcaatatc
agcacaagcataagaggtaaggtgcagaaagaatatgcatttttttataa
acttgatataataccaatagataatgatactaccagctatacgttgacaa
gttgtaacacctcagtcattacacaggcctgtccaaaggtatcctttgag
ccaattcccatacattattgtgccccggctggttttgcgattctaaaatg
```

-continued

```
taataataagacgttcaatggaacaggaccatgtacaaatgtcagcacag
tacaatgtacacatggaattaggccagtagtatcaactcaactgctgttg
aatggcagtctagcagaagaagaggtagtaattagatctgccaatttcac
agacaatgctaaaaccataatagtacagctgaaccaatctgtagaaatta
attgtacaagacccaacaacaatacaagaaaaagtatccgtatccagagg
ggaccagggagagcatttgttacaataggaaaaataggaaatatgagaca
agcacattgtaacattagtagagcaaaatggaatgccacttttaaaacaga
tagctagcaaattaagagaacaatttggaaataataaaacaataatctttt
aagcaatcctcaggaggggacccagaaattgtaacgcacagttttaattg
tggagggaattttctactgtaattcaacacaactgtttaatagtactt
ggtttaatagtacttggagtactgaagggtcaaataacactgaaggaagt
gacacaatcacactcccatgcagaataaaacaatttataaacatgtggca
ggaagtaggaaaagcaatgtatgcccctcccatcagcggacaaattagat
gttcatcaaatattacagggctgctattaacaagagatggtggtaataac
aacaatgggtccgagatcttcagacctggaggaggagatatgagggacaa
ttggagaagtgaattatataaatataaagtagtaaaaattgaaccattag
gagtagcacccaccaaggcaaagaagagtggtgcagagagaaaaaga
gcagtgggaataggagctttgttccttgggttcttgggagcagcaggaag
cactatgggcgcacggtcaatgacgctgacggtacaggccagacaattat
tgtctggtatagtgcagcagcagaacaatttgctgagggctattgaggcg
caacagcatctgttgcaactcacagtctggggcatcaagcagctccaggc
aagaatcctggctgtggaaagatacctaaaggatcaacagctcctgggga
tttgggttgctctggaaaactcatttgcaccactgctgtgccttggaat
gctagttggagtaataaatctctggaacagatttggaataacatgacctg
gatggagtgggacagagaaattaacaattacacaagcttaatacattcct
taattgaagaatcgcaaaaccagcaagaaaagaatgaacaagaattattg
gaattagataaatgggcaagtttgtggaattggtttaacataacaaattg
gctgtggtatataaaaatattcataatgatagtaggaggcttggtaggtt
taagaatagttttttgctgtactttctatagtgaatagagttaggcaggga
tattcaccattatcgtttcagacccacctcccaacccgagggggacccga
caggcccgaaggaatagaagaagaggtggagagagagacagagacagat
ccattcgattagtgaacggatccttagcacttatctgggacgatctgcgg
agcctgtgcctcttcagctaccaccgcttgagagacttactcttgattgt
aacgaggattgtggaacttctgggacgcagggggtgggaagccctcaaat
attggtggaatctcctacagtattggagtcaggaactaaagaatagtgct
gttagcttgctcaatgccacagccatagcagtagctgaggggacagatag
ggttatagaagtagtacaaggagcttgtagagctattcgccacatacccta
gaagaataagacagggcttggaaaggattttgctataagatgggtggcaa
gtggtcaaaaagtagtgtggttggatggcctactgtaagggaaagaatga
gacgagctgagccagcagcagatggggtgggagcagcatctcgagacctg
gaaaaacatggagcaatcacaagtagcaatacagcagctaccaatgctgc
```

-continued

```
ttgtgcctggctagaagcacaagaggaggaggaggtgggttttccagtca
cacctcaggtacctttaagaccaatgacttacaaggcagctgtagatctt
agccacttttaaaagaaaaggggggactggaagggctaattcactccca
acgaagacaagatatccttgatctgtggatctaccacacacaaggctact
tccctgattggcagaactacacaccagggccagggtcagatatccactg
acctttggatggtgctacaagctagtaccagttgagccagataaggtaga
agaggccaataaaggagagaacaccagcttgttacaccctgtgagcctgc
atggaatggatgaccctgagagagaagtgttagagtggaggtttgacagc
cgcctagcatttcatcacgtggcccgagagctgcatccggagtacttcaa
gaactgctgacatcgagcttgctacaagggactttccgctggggactttc
cagggaggcgtggcctgggcgggactggggagtggcgagccctcagatgc
tgcatataagcagctgcttttttgcctgtactgggtctctctggttagacc
agatttgagcctgggagctctctggctaactagggaacccactgcttaag
cctcaataaagcttgccttgagtgcttca
```

Other targets for CEM-15 can include the RNA and first strand DNA from: simian immunodeficiency virus (SIV), equine infectious anemia virus (EIAV), and murine leukemia virus, as well as other human lentiviruses, and retroviruses such as T-cell leukemia virus, spleen necrosis virus, and the pararetorvirus hepatitis B virus.

Mooring Sequences

Mooring sequences are the nucleic acid sequences recognized by cytidine deaminases. These sequences act as the recognition site for the enzyme, which can then deaminate a cytidine that is within a given length of the mooring sequence.

In APOBEC-1, RNA secondary structure does not appear to be required for apoB RNA editing. Instead, apoB mRNA editing requires an 11 nucleotide motif known as the mooring sequence. Placement of the mooring sequence 4-8 nucleotides 3' of a cytidine within reporter RNAs is frequently sufficient for that RNA to support editing (Smith (1993) *Seminars in Cell Biol.* 4, 267-78; Sowden (1998) *Nucl. Acids Res.* 26, 1644-1652; Backus and Smith (1992) *Nucl. Acids Res.* 22, 6007-14; Backus and Smith (1991) *Nucl. Acids Res.* 19, 6781-86; Backus and Smith (1994) *Biochim. Biophys. Acta* 1217, 65-73; Backus and Smith (1994) *Biochim. Biophys. Acta* 1219, 1-14; Sowden et al., (1996) RNA 2, 274-88). The mooring sequence is left intact in edited mRNA and therefore its occurrence downstream of a cytidine is predictive of an editing site.

Alone APOBEC-1 exhibits only nominal affinity for AU-rich sequences within the region of the apoB mRNA mooring sequence (Anant and Davidson (2000) Mol. Cell. Biol. 20, 1982-1992, incorporated by reference in its entirety). The consensus sequence for APOBEC-1 binding is: 5'UUUN[A/U]U-3' (SEQ ID NO: 11) The mooring sequence described by Smith (1993) Seminars in Cell Biology 4, 267-278), herein incorporated by reference) is:

5'-C*AAuu[uGauCAGUAUA]uu-3'    (SEQ ID NO: 12)

(where C* is the cytidine to be edited) and is highly conserved among 32 mammalian sequences (Hersberger et al & Innerarity, (1999) J. Biol. Chem. 274, 34590-34597, herein incorporated by reference in its entirety for teachings related to mooring sequences). Regions in lower case are specific "high affinity" sequences for APOBEC-1 binding. Regions in brackets define the "mooring sequence." A cytidine deaminase inhibitor can utilize both the upstream sequence at the edited C (denoted by * and would be substituted with a zebularine or other cytidine deaminase inhibitor nucleotide) as well as downstream regions including the mooring sequence. The minimal sequence size capable of supporting editing (and hence and effective cytidine deaminase inhibitor of APOBEC-1 is ≧about a 26-mer) having a nucleic acid sequence:

```
5'-GAUA(Z*)AAUU[UGAUCAGUAUA]U-3'.    (SEQ ID NO: 13).
```

Auxiliary Proteins

Disclosed are cytidine deaminase inhibitors comprising a nucleoside incorporated in a polymeric substrate, wherein the polymeric substrate targets an auxiliary protein of a cytidine deaminase. An auxiliary protein of a cytidine deaminase is a protein that assists the cytidine deaminase in nucleic acid recognition, and specifically in recognized editing sites.

One example of an auxiliary protein of a cytidine deaminase is APOBEC-1 Complementing Factor (ACF). The nucleotide sequence recognized by ACF is the mooring sequence RNA disclosed above (SEQ ID NO: 13).

Another example of an auxiliary protein of a cytidine deaminase is APOBEC-1 Stimulating Protein (ASP). ASP recognizes the mooring sequence and is a spliced variant of ACF (Dance et al., 2002) *J. Biol. Chem.* 277, 12703-09). Additional ACF spliced variants are ACF45 and ACF43 that also bind to the mooring sequence (Sowden et al., (2004) *J. Biol. Chem.* 279, 197-206)

Other mRNA sequences targeted by APOBEC-1 which can be inhibited by cytidine deaminase inhibitor include, but are not limited, to NF1 (neurofibromin 1), whose targeted sequence is

```
                                    (SEQ ID NO: 14)
5'-CCUUUAUUA(Z*)GAAUUGUGAUCACAUCCUCUG-3',
``` wherein "Z" is the nucleoside residue.

Unregulated transgenic expression of APOBEC-1 confers susceptibility to liver cancer (Sowden, M., (1996) *J Biol Chem,* 271:3011-7; Yamanaka, S., et al., (1995) *PNAS USA,* 92, 8483-7, herein incorporated by reference in their entireties), possibly as a result of nonspecific mRNA editing affecting the NAT1 translational repressor. The following human NAT-1 (novel APOBEC-1 target) sequences are listed with each "mooring sequence" underlined.

```
                                    (SEQ ID NO: 15)
5'-aagcaagttztttgatcagtttactcaaaca-3'

(SEQ ID NO: 16)
5'-aaatgctgczagaaattgatcagaataagga-3'

(SEQ ID NO: 17)
5'-ttacttgcazcaaactgatcagttttgagag-3'
```

Yamanaka et al. looked at several proteins and reported editing of protein tyrosine kinase (TEC). Only the latter was edited

```
Mouse TEC sequence
                                    (SEQ ID NO: 18)
5'-aggtacgttztggatgatcagtacacaagttc-3'
```

-continued
Corresponding HUMAN TEC Sequence
```
                                    (SEQ ID NO: 19)
5'-aggtatgttztggatgatcagtacacaagttc-3'
```

APOBEC-1 relies on auxiliary proteins for RNA recognition (Grosjean and Benne (1998); Teng (1993) *Science* 260: 1816-19; Sowden (1998) *Nucl. Acids Res.* 26:1644-52; Inui (1994) *J. Lipid Res.* 35:1477-89; Dance (2001) *Nucl. Acids Res.* 29:1772-80). APOBEC-1 only has weak RNA binding activity of low specificity (Anant (1995) *J. Biol Chem* 270, 14768-75; MacGinnitie (1995) *J. Biol Chem,* 270, 14768-75). To edit apoB mRNA, APOBEC-1 requires, in addition to the mooring sequence described above, RNA binding proteins that bind apoB mRNA and to which APOBEC-1 can bind and orient itself to C6666. The components of the minimal editosome from defined in vitro system analyses are APOBEC-1 as a homodimeric cytidine deaminase (Lau, P. P., (1994) *PNAS U.S.A.* 91, 8522-8526) bound to the auxiliary protein ACF/ASP that serves as the editing-site recognition factor through its mooring-sequence-selective RNA-binding activity (Mehta, A., (2000) *Mol. Cell. Biol.* 20, 1846-1854; Lellek, H., (2000) *J. Biol. Chem.* 275, 19848-19856). Several other auxiliary protein candidates have also been described that had binding affinities for APOBEC-1 and/or apoB mRNA and that demonstrated the ability to modulate editing efficiency (Giannoni, F., et al., (1994) *J. Biol. Chem.* 269, 5932-5936; Yamanaka, S., et al., (1994) *J. Biol. Chem.* 269, 21725-21734; Yang, Y., et al., (1997) *J. Biol. Chem.* 272, 27700-27706; Lellek, H., et al., (2000) *J. Biol. Chem.* 275, 19848-19856; Teng, B., et al., (1993) *Science* 260, 1816-1819; Inui, Y., et al., (1994) *J. Lipid Res.* 35, 1477-1489; Anant, S. G., et al., (1997) *Nucleic Acids Symp. Ser.* 36, 115-118; Lau, P. P., et al., (1997) *J. Biol. Chem.* 272, 1452-1455).

ACF was isolated and cloned using biochemical fractionation and yeast two hybrid genetic selection (Mehta et al., (2000) *Mol. Cell. Biol.* 20, 1846-54; Lellek (2000) JBC 275: 19848-56). Overexpression of 6His-tagged APOBEC-1 in mammalian cells enabled the intracellularly assembled editosome to be affinity purified (Yang Y. et al., (1997) *J. Biol. Chem.* 272, 27700-06). ACF associated with APOBEC-1 through 1M NaCl resistant interactions and that three other RNA binding proteins (100 kDa, 55 kDa and 44 kDa) with affinity for the mooring sequence co-purified with the editosome (Yang, Y. et al., (1997) *J. Biol. Chem.* 272, 27700-06). P100 and p55 were both mooring-sequence-selective RNA binding proteins but p44 was a general RNA binding protein. Additional studies utilizing yeast two hybrid analyses using APOBEC-1 affinity and antibodies developed against the editosome and ACF have demonstrated proteins such as hnRNP ABBP1 (Lau, P. et al., (1997) *J. Biol Chem* 272, 1452-55), the alternative splicing factor KSRP (Lellek et al., (2000) *J. Biol Chem* 275, 19848-56) and αI3 serum proteinase inhibitor as positive modulators of editing activity (Schock, D. et al., (1996) *PNAS USA* 93, 1097-1102) and hnRNP protein C (Greeve, J. et al., (1998) *Biol. Chem.* 379, 1063-73) and GRY-RBP (Blanc, V. et al., (2001) *J. Biol Chem,* 276, 10272-83; Lau, P. et al., (2001) *Biochem. Biophys. Res. Commun.* 282, 977-83) as negative modulators of apoB mRNA editing.

Disclosed are compositions comprising a cytidine deaminase inhibitor, such as those described above, and a pharmaceutical carrier.

The compositions can be administered in vivo in a pharmaceutically acceptable carrier. By "pharmaceutically acceptable" is meant a material that is not biologically or otherwise undesirable, i.e., the material may be administered to a subject, along with a nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Delivery

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions, can comprise, for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. (1989) *Am. J. Resp. Cell. Mol. Biol.* 1, 95-100); Felgner et al. (1987) *PNAS USA* 84, 7413-7417); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

Disclosed are methods of treating a subject with cancer, or having a predisposition to cancer. Such cancers include, but are not limited to, those associated with AID, like B cell malignancies such as diffuse large B cell lymphomas and chronic lymphatic leukemia. The disorder can also be a T cell lymphoma or a pulmonary adenoma. Also included are those cancers associated with APOBEC-1, like colorectal cancer and neurofibromatosis. Also included are those cancers associated with CEM15, such as breast cancer. Cancers involving overexpression of other ARPs of listed in Wedekind et al. (2003) Trends in Genetics, herein incorporated by reference in it's entirety.

As used throughout, administration of a cytidine deaminase inhibitor can occur in conjunction with other therapeutic agents. Thus, the cytidine deaminase inhibitors of the present invention can be administered alone or in combination with one or more therapeutic agents. For example, a subject can be treated with a cytidine deaminase inhibitor alone, or in combination with chemotherapeutic agents, antibodies, antivirals, steroidal and non-steroidal anti-inflammatories, conventional immunotherapeutic agents, cytokines, chemokines, and/or growth factors. Combinations may be administered either concomitantly (e.g., as an admixture), separately but simultaneously (e.g., via separate intravenous lines into the same subject), or sequentially (e.g., one of the compounds or agents is given first followed by the second). Thus, the term "combination" or "combined" is used to refer to either concomitant, simultaneous, or sequential administration of two or more agents.

A cytidine deaminase inhibitor is an agent that inhibits editing of nucleic acids by cytidine deaminases. Additional genetic, pharmacologic, or metabolic agents or conditions also modulate the RNA or DNA editing or mutating function of the deaminase. Some of the conditions that modulate editing activity include: (i) changes in the diet, (ii) hormonal changes (e.g., levels of insulin or thyroid hormone), (iii) osmolarity (e.g., hyper or hypo osmolarity), (iv) ethanol, (v) inhibitors of RNA or protein synthesis and (vi) conditions that promote liver proliferation. Thus, the methods of the invention can comprise administering a cytidine deaminase inhibitor to the subject and using other conditions that reduce the efficiency of mRNA editing function or the efficacy of the cytidine deaminase.

Disclosed are methods of treating a condition, wherein the condition is a cancer. The cancer can be selected from the group consisting of lymphomas (Hodgkins and non-Hodgkins), B cell lymphoma, T cell lymphoma, myeloid leukemia, leukemias, mycosis fungoides, carcinomas, carcinomas of solid tissues, squamous cell carcinomas, adenocarcinomas, sarcomas, gliomas, blastomas, neuroblastomas, plasmacytomas, histiocytomas, melanomas, adenomas, hypoxic tumours, myelomas, AIDS-related lymphomas or sarcomas, metastic cancers, bladder cancer, brain cancer, nervous system cancer, squamous cell carcinoma of head and neck, neuroblastoma/glioblastoma, ovarian cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, hematopoietic cancers, testicular cancer, colo-rectal cancers, prostatic cancer, or pancreatic cancer.

Cytidine deaminase inhibitors are of benefit to individuals who are over-expressing cytidine deaminases, as well as those individuals who would benefit from a reduction in their activity. Because cytidine deaminase inhibitors reduce the activity of cytidine deaminases, the mutation rate of certain nucleic acids recognized by the cytidine deaminase is reduced, and any subject that can benefit from a reduction in the activity of cytidine deaminases can be administered cytidine deaminase inhibitor. This includes those receiving exogenous nucleic acids via a viral vector, in which a reduction in the recognition of these viral vectors would be beneficial. Therefore, the cytidine deaminase inhibitors can be administered in combination with viral vectors. For example, inactivation of AID can permit introduction and function of the viral vector delivered therapeutic model, such as RNA, DNA, siRNA, or protein, so these two technologies can be used in tandem.

One skilled in the art will appreciate that the viral vector can comprise any viral vector useful in delivery of exogenous nucleic acids. For example, the viral vector can be a recombinant adenovirus vector, an adeno-associated viral vector, a lentiviral vector, a pseudotyped retroviral vector, a vaccinia vector, an alphavirus vector, or any other viral vector known in the art or described throughout.

In particular, the viral vector can be a retrovirus. A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, which is incorporated by reference herein in its entirety for the retroviral vectors taught and methods of making or using the same. Examples of methods for using retroviral vectors for exogenous nucleic acid delivery are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference in their entirety for the methods taught herein. The retrovirus can be in the Oncovirinae subfamily of retroviruses, such as HTLV-I or HTLV-II (human T-cell leukemia virus type I and type II, respectively). Additionally, the retrovirus can be in the Lentivirinae subfamily of retroviruses, such as HIV-1, HIV-II, SIV, FIV, EIAV and CAEV (human immunodeficiency virus type I, human immunodeficiency virus type II, simian immunodeficiency virus, feline immunodeficiency virus, equine infectious anemia virus, and caprine arthritis-encephalitis virus, respectfully).

A retrovirus is essentially a package that has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome contains the gag, pol, and env genes which are involved in the making of the protein coat. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

Because cytidine deaminases are known to act upon viruses, inactivating these cytidine deaminases in the presence of viral vectors allows for tissue specific gene transfer and insertion for therapeutic purposes (i.e. retroviral DNA synthesis and genome incorporation). The infectivity of HIV-1 is markedly reduced in T lymphocytes that naturally express CEM15 (Sheehy et al., (2002) Nature, 418, 646-50). Recent research has demonstrated that CEM15 acts as a host cell defense mechanism by introducing numerous dC to dU and dG to dA mutations in the HIV-1 genome during it's replication, rendering the virus nonfunctional (Mangeat, B. et al., (2002) Nature 424, 99-103; Mariani, R. et al., (2003) Cell 114, 21-31; Zhang, H. et al., (2003) Nature 424, 94-8). A critical step for this activity is for CEM15 to incorporate into viral particles during their assembly (Mariani, R. et al., (2003) Cell 114, 21-31; Stopak, K. et al., (2003) Mol Cell 12, 591-601) and then, subsequent to infection, mutate single stranded DNA during viral replication Mangeat, B. et al., (2002) Nature 424, 99-103; Zhang, H. et al., (2003) Nature 424, 94-8; Stopak, K. et al., (2003) Mol Cell 12, 591-601). This defense mechanism can be blocked by the HIV protein known has Vif (Sheehy et al., (2002) Nature, 418, 646-50) which reduces the expression of CEM15 (Stopak, K. et al., (2003) Mol Cell 12, 591-601) and binds to CEM15 (Mariani, R. et al., (2003) Cell 114, 21-31; Yang, B. et al., (2003) J. Biol. Chem. 278, 6596-602), targeting it to the protein degradation pathway of the cell (Stopak, K. et al., (2003) Mol Cell 12, 591-601; Liu, B. et al., (2004) J. Virol. 78, 2072-81; Sheehy, A. M., et al., (2003) Nat. Med. 9, 1404-7). Viral particles produced from Vif positive HIV contain Vif (Ohagen, A. and Gabuzda, D. (2000) J. Virol. 74, 11055-66; Zhang, H. et al., (2000) J. Virol. 74, 8252-61; Simon, J. H. et al., (1996) J. Virol. 70, 5297-305; Khan, M. A. et al., (2001) J. Virol. 75, 7252-65) but contain low or no CEM15 (Mariani, R. et al., (2003) Cell 114, 21-31; Stopak, K. et al., (2003) Mol Cell 12, 591-601; Liu, B. et al., (2004) J. Virol. 78, 2072-81; Sheehy, A. M., et al., (2003) Nat. Med. 9, 1404-7) and consequently are infectious. These new understandings suggest that there are at least two times when CEM15 activity is critical in host defense from HIV infection. These are: early during infection when the viral RNA genome is replicated and late in infection when viral particles are being assembled. Both of these require CEM15 localization within the cytoplasm of the host cell and this has been confirmed by immunolocalization and biochemical fractionation.

The compositions comprising a cytidine deaminase inhibitor in a pharmaceutically acceptable carrier may be administered orally, parenterally (e.g., intravenously), by intramuscular injection, by intraperitoneal injection, transdermally, extracorporeally, topically or the like, although topical intranasal administration or administration by inhalant is typically preferred. As used herein, "topical intranasal administration" means delivery of the compositions into the nose and nasal passages through one or both of the nares and can comprise delivery by a spraying mechanism or droplet mechanism, or through aerosolization of the nucleic acid or vector. The latter may be effective when a large number of animals is to be treated simultaneously. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Cytidine deaminase inhibitor for APOBEC-1, used to reduce apoB mRNA editing in the small intestine, can be administered orally, for example. RNA is stable to stomach acids, and the ribonucleases can have modified backbones in one embodiment. As disclosed herein, peptide sequences can be used with the RNA molecule during its synthesis (for example, using the TAT motif for enhanced uptake). It is also envisioned that peptide-oligos contain information, not only for compound entry, but also for targeting by employing peptidyl nuclear or cytoplasmic nuclear localization signals, such as PNAs, can be used.

In one aspect, the cytidine deaminase inhibitor molecule can be a PNA (peptide-RNA), for example. This molecule can serve to both stabilize the oligonucleotide as well as encoding a motif such as the cell transduction motif of 'TAT', for example, which permits the penetration of the cytidine deaminase inhibitor into cells. For example, the methodology to establish a peptide in covalent linkage to an oligonucleotide has been described by Glen Research (http://www.glenresearch.com) (Example 10). In another aspect, the cytidine deaminase inhibitor can be a non-peptidyl-oligo composed of an inert non-peptidyl based mimic. For example, any compound possessing one or non-protease digestable amino acid linkages (i.e., inert peptide bond) can be used in this aspect. The synthesis of the non-peptidyl-oligos can be performed using similar techniques described above for producing peptide-oligos. Examples of molecules having one or more inert peptide bonds are well known in the art and can be found, for example, in the HIV-1 protease inhibitor field. In one aspect, the non-peptidyl based mimic UIC-94017 disclosed in Koh et al., *Antimicrobial Agents and Chemotherapy*, vol. 47, no. 10, p. 3123-3129, October 2003, can be used herein.

In one example, nanoparticles are used such as those described by Lambert G, et al. (Drug Deliv Rev. 2001; 47, 99-112). Lambert et al. reviewed various assemblies to deliver anti sense oligonucleotides. For example, in vivo, polyalkylcyanoacrylate (PACA) nanoparticles were able to efficiently distribute the antisense molecules to the liver. Alginate nanosponges can concentrate the antisense molecules in the lungs. Antisense loaded to PACA nanoparticles were able to improve the treatment of RAS cells expressing the point mutated Ha-ras gene in mice.

The composition can include active components that can be delivered to a subject for which delivery to the intestine is desired. Examples of such additional components are numerous and are well known in the art. For example, there have been described various forms of composites which make possible active ingredients to be delivered to the intestine including for example those in the form of capsule (Japanese Patent Laid-Open Publication Nos. 41422/1992, 225922/1992, 179618/1994, and 327634/1995), those coated with monolayer (Japanese Patent Laid-Open Publication Nos. 368321/1992, and 2701/1995), and those coated with chitosan and a special polymer (Japanese Patent Laid-Open Publication Nos. 34927/1991, 69333/1992, and 217924/1992), herein incorporated in their entirety for methods of delivery to the intestine.

Intestinal absorption enhancers can be used as well. These fall within the following general classes: (1) calcium chelators, such as citrate and EDTA; and (2) surfactants, such as sodium dodecyl sulfate, bile salts, palmitoylcarnitine, and sodium salts of fatty acids, for example.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein in its entirety for the methods taught.

The compositions may be in solution or in suspension (for example, incorporated into microparticles, liposomes, or cells). These compositions may be targeted to a particular cell type via antibodies, receptors, or receptor ligands. The following references are examples of the use of this technology to target specific proteins to given tissue (Senter, et al., Bioconjugate Chem., 2:447-451, (1991); Bagshawe, K. D., (1989) *Br. J. Cancer*, 60, 275-281; Bagshawe, et al., (1988) *Br. J. Cancer*, 58, 700-703; Senter, et al., (1993) *Bioconjugate Chem.*, 4, 3-9; Battelli, et al., (1992) *Cancer Immunol. Immunother.*, 35, 421-425; Pietersz and McKenzie, (1992) *Immunolog. Reviews*, 129, 57-80; and Roffler, et al., (1991) *Biochem. Pharmacol*, 42, 2062-2065). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, (1991) *DNA and Cell Biology* 10, 6, 399-409).

Pharmaceutically Acceptable Carriers

Delivery of the cytidine deaminase inhibitors can be used therapeutically in combination with a pharmaceutically acceptable carrier. Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including opthamalically, vaginally, rectally, intranasally), orally, by inhalation, or parenterally, for example by intravenous drip, subcutaneous, intraperitoneal or intramuscular injection. The disclosed compounds can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Therapeutic Uses

The dosage ranges for the administration of the compositions are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any contraindications. Dosage can vary, and can be administered in one or more dose administrations daily, for one or several days.

Cytidine deaminase inhibitors that do not have a specific pharmaceutical function, but which may be used for tracking changes within cellular chromosomes or for the delivery of diagnostic tools for example can be delivered in ways similar to those described for the pharmaceutical products.

As described previously, cytidine deaminase inhibitors can be administered together with other forms of therapy. For example, the molecules can be administered with antibodies, antibiotics, or other cancer treatment protocols as described above, or viral vectors. When the cytidine deaminase inhibitor is in a vector, as described above, the vector containing the nucleic acid for therapeutic purposes can also contain the cytidine deaminase inhibitor.

Also disclosed are cells comprising a cytidine deaminase inhibitor or comprising a nucleic acid that encodes the cytidine deaminase inhibitor, such as those described above. Disclosed are cell lines comprising a cytidine deaminase inhibitor. The cytidine deaminase inhibitor can be contained in a vector, or can be part of the genome of the cell. The cytidine deaminase inhibitor can comprise a nucleoside incorporated in a polymeric substrate, wherein the polymeric substrate targets a cytidine deaminase or a cytidine deaminase auxiliary protein. The cytidine deaminase inhibitor can be any of those cytidine deaminase inhibitors described above.

The disclosed cell lines can be used in a variety of ways. For example, they can be used as tools to study cytidine deaminases. The cell line can be monitored in vitro for the inhibitory activity of cytidine deaminase inhibitors. The cell line can also be used for screening drugs that inhibit the efficacy of the cytidine deaminase inhibitor. Alternatively, cells of the cell line can be administered to a test animal and monitored for the effect thereof. The cell line can be used for drug discovery and for drug validation. Substances that are known or suspected of interacting with cytidine deaminase inhibitors can be administered to the cell line, and the effects thereof monitored. Combinations of the above can also be used to monitor the cause and effect relationship of various drug candidates. The disclosed cell lines can also be used as reagents to produce other beneficial cell lines, by for example, allowing the cell lines to multiply. These cell lines are useful as model systems for drug discovery and validation.

Methods of Using the Compositions

Disclosed are methods of inhibiting cytidine deaminases comprising contacting a cell containing the cytidine deaminase with a cytidine deaminase inhibitor under conditions that allow the inhibitor to inhibit the deaminase function of the cytidine deaminase. The step of contacting the cytidine deaminase with a cytidine deaminase inhibitor can occur either in vivo or in vitro.

By "inhibiting cytidine deaminases" is meant inhibiting the functionality of the enzyme, or inhibiting its ability to deaminate nucleic acids. The cytidine deaminase can be inhibited at 10%, 20%, 30%, 40%, 50%, 60%, 70%, 80% or 90%, or 100% or greater or any amount in between, compared to a control cytidine deaminase or the normal functionality of the cytidine deaminase either in vivo or in vitro.

Also disclosed is a method of treating a subject with a disorder associated with a cytidine deaminase comprising administering to the subject a cytidine deaminase inhibitor as taught herein. The disorder associated with cytidine deaminase can be a disorder associated with AID. Such disorders include, but are not limited to, B cell malignancies such as diffuse large B cell lymphomas and chronic lymphatic leukemia. The disorder can also be a T cell lymphoma or a pulmonary adenoma.

The disorder associated with cytidine deaminase can also be a disorder associated with APOBEC-1. Such disorders include, but are not limited to cancers such as colorectal cancer, neurofibromatosis, atherosclerosis, steatosis (fatty liver disease) and metabolic syndrome.

The disorder can also be associated with CEM15. Such disorders include, but are not limited to, cancers such as breast cancer.

As discussed above, also disclosed are methods of promoting viral vector incorporation in a subject comprising the step of administering to the subject a therapeutic amount of a cytidine deaminase inhibitor. The cytidine deaminase inhibitor can be any cytidine deaminase inhibitors described herein.

Disclosed are methods of promoting incorporation of a viral vector in a subject comprising the steps of administering to the subject a therapeutic amount of a cytidine deaminase inhibitor and administering the viral vector to the subject. The cytidine deaminase inhibitor can be any of those cytidine deaminase inhibitors described above.

Cytidine deaminase inhibitors can induce nucleotide deamination in the sequence of the retroviral vector itself either during its reverse transcription, replication and/or during the expression of RNA from the transgene after the virus integrated into the cell's chromosomes. The gene that the retrovirus is carrying is mutated as well, thereby reducing or eliminating functional protein expression (an effect that appears as low efficiency of transduction by the virus). Also as described above, the sites that are affected are those that are exact or approximate target sites that enable binding of CEM15 directly or through an auxiliary protein of CEM15. The partial or total mutation of C's (or A's as would be the case of ADAR1) blunts the ability of the retroviruses to express functional proteins from its own genes and the gene(s) it carries and therefore the retrovirus is not able to integrate into the cells' chromsomes.

Also disclosed is a method of screening for a cytidine deaminase inhibitor comprising the steps of contacting a cytidine deaminase with an agent to be screened, wherein the agent is incorporated in a polymeric substrate, wherein the polymeric substrate targets the cytidine deaminase; and determining the level of cytidine deaminase activity. A reduction in cytidine deaminase activity, as compared to cytidine deaminase activity in the absence of the agent to be screened, indicating a cytidine deaminase inhibitor. A reduction in cytidine deaminase activity is defined as less than 10%, 20%, 30%, 40%, 50%, 60%, 70%, 80%, 90%, 100% or greater or any amount in between reduction in activity compared to a control or to the normal level of activity ascribed to the cytidine deaminase.

In the screening methods, the cytidine deaminase can be in a cell, or can be in a transgenic animal. The method of screening can occur either in vivo, ex vivo, or in vitro. The polymeric substrate can comprise oligonucleotide residues. The polymeric substrate can be a nucleic acid that specifically targets the cytidine deaminase. Cytidine deaminase activity can be determined using a variety of techniques known in the art and taught by the following examples.

The present invention is more particularly described in the following examples which are intended as illustrative only since numerous modifications and variations therein will be apparent to those skilled in the art.

EXAMPLES

Example 1

Methods for Synthesizing Context Dependent Inhibitors Containing Zebularine

Sources of Deoxy Zebularine Phosphoramidite: synthesis of deoxyzebularine phosphoramidite (DNA) is known in the art (Cheng, J. C., et al., J Natl Cancer Inst, 95(5):399-409, 2003). Also, 5-methyl-2'-deoxyzebularine is commercially available from Glen Research. The base is rather unstable at high pH during which the exocylic amine undergoes deblocking at the end of the synthesis. Hence, the synthesis needs "ultramild CE phosphoramidites," which can be purchased from Glen Research (http://www.glenres.com).

There are the following options for synthesis: DNA Phosphoramidites, CE phenoxyacetyl (Pac) protected dA, CE acetyl (Ac) protected dC, and CE 4-isopropyl-phenoxyacetyl (iPr-Pac) protected dG (thymine/uridine do not need to be deblocked since there is no exocylic amine).

The forementioned method was employed in the synthesis of a context dependent inhibitor of DNA harboring 5-methyl-2'-deoxyzebularine. As proof of principle, a sequence was synthesized was a 15-mer comprising: 5'-d(AGC-TAG-(dmZ)-TAA-GTT-AT)-3' (SEQ ID NO: 22), where one of the edited positions has been replaced by 5-methyl-2'-deoxyzebularine denoted (dmZ). This product represents a substrate for the enzyme activation induced deaminase (AID) as reported by Goodman and colleagues (Bransteitter, R. et al (2003) *Proc. Natl. Acad. Sci. USA* 100, 4102-4107). The phosphoramidites used were those of the ultramild class, which were purchased from Glen Research. The phosphoramidites were coupled on a 1 μmole scale using a DNA Synthesizer with coupling times and procedures recommended by Glen Research for mild phosphoramidites. The DNA product was deblocked and the trityl group removed under mild conditions described by Glen Research. The partially lyophilized product was resuspended in 0.1 M Triethylammonium acetate (TEAA) buffer pH 7.0 (Buffer A) and subjected to HPLC purification using a 1.9×30 cm μ-Bondapack C18 column (Waters) operated at 7 ml min$^{-1}$. The product eluted as a single peak (FIG. 12) with a retention time of 44.3 min; failure sequences and impurities were clearly separated in this step. The ion pairing elution buffer comprised Buffer A with 50% acetonitrile (Buffer B). The percent of Buffer B upon elution was 26%. The gradient started at 15% Buffer A and ended at 30% Buffer A in 70 min. Peak fractions were pooled and the pure product was lyophilized and desalted on a SepPak C18 cartridge (Waters). The DNA was detected at 260 nm and the pooled material was lyophilized to dryness. The yield was 25% (nearly 2 mg). The sample was resuspended in water and analyzed by MALDI/TOF mass spectrometry (FIG. 13). The major peak was observed at an m/z of 4532. This result demonstrates the existence of an oligomer of the correct MW that represents the largest component of the sample.

As another option to make RNA inhibitors containing 2'-OMe groups, the following options are available, although the deoxyzebularine must be used at the site of C-to-U conversion: 2'-OMe RNA Phosphoramidites, phenoxyacetyl (Pac) protected 2'-OMe-A, acetyl (Ac) protected 2'-OMe-C, and 4-isopropyl-phenoxyacetyl (iPr-Pac) protected 2'-OMe-G (regular 2'-OMe-uridine can be used).

The Cap A reagent to phenoxyacetic anhydride needs to be changed to be compatible with ultramild bases, and used with an "ultramild" solid phase support (page 22-23 of the Glen Catalog on the internet). 2'-OMe-U can be purchased as a starting material but 2'-OMe CPG has to be synthesized. Using these mild reagents allows the ammonia deblocking step to be reduced to 4 hours at room temp. On the Glen Research website, 0.05M potassium carbonate in methanol is recommended. Alternatively, ethanolic ammonium hydroxide can be used.

Apart from the above, no changes are needed to the synthesis. The zebularine phosphoramidite can be dissolved at the normal concentrations (0.1 M), filtered, and coupled for the same time as a normal deoxy phosphoramidite. However, careful purification is needed as the mild ammonia reduces, but does not eliminate, destruction of the zebularine base. "DMT-on" purification can be performed, along with initial purification on reverse-phase HPLC (C18) with buffers as follows: A: 0.1 M triethylammonium acetate pH 6.5+5% CH$_3$CN; B: 0.1 M triethylammonium acetate pH 6.5+65% CH$_3$CN; and 25 to 65% B, over 30 minutes. The desired DMT-on product elutes at about 12-15 minutes (failure sequences, which lack the hydrophobic group elute in the void volume).

The product is collected in bulk based on absorption at 260 nm, lyophilized to near dryness at −95° C. to remove TEAA buffer and the DMT group hydrolyzed by incubating in 80% acetic acid/20% water for 30 minutes. The solution is stopped by freezing in liquid N$_2$ and acetic acid can be removed by lyophilization; adding 1 ml of water and evaporating (repeat 3 times) removes all the acid).

A normal oligonucleotide is pure at this stage, however this is not true with zeb-derivatives. A second reverse phase HPLC purification is required with a shallower gradient; 0-25% buffer B, over 30 minutes. A cluster of closely running peaks elute at around 10-15 minutes. The desired zeb product is usually the biggest, slowest running peak. Identity can be confirmed by MALDI-TOF MS or UV absorbance/fluorescence spectroscopy. zebularine absorbs at ~305 nm and zebularine oligos contain a shoulder (sometimes not very prominent) at this wavelength. Zebularine is also fluorescent, excitation at 305 gives fluorescence at about 390 nm. Yields are usually 20-30% compared to an oligonucleotide of the same length with only normal bases.

The phosphoramidite is stored desiccated at minus 20° C. (stable forever). Likewise the final zebularine-oligos are stable when stored frozen at −20° C.

Example 2

Alternate Methods for Synthesizing Cytidine Deaminase Inhibitors

One compound useful as a cytidine deaminase inhibitor can be 4-fluoro zebularine. One advantage of such an inhibitor is that it is more reactive than the parent compound. Conceptually, the nucleoside should hydrate at C4 like zebularine and 5-fluorozebularine. However, the hydrated tetrahedral carbon has F instead of H, and since F is more an isostere for the hydroxyl, the compound may not bind effectively at the active site. Other substitutions at 2' are designed to influence the ribose sugar pucker to more closely mimic the conformers of RNA, as well as their hydrogen bonding properties. In this respect, 2'-Fluoro can be used. Due to its inert nature, this position does not require protection during chemical synthesis.

Example 3

Reduction in Small Intestinal apoB mRNA Editing to Reduce B48 Containing Chylomicron Remnants in Patients with Metabolic Syndrome

The nucleotide analog deoxyzebularine, in the context of single-stranded (ss) RNA or PNA oligonucleotides comparable to SEQ ID NO: 12, can be used to reduce apoB mRNA editing in the small intestine: Cholesterol is carried in the blood from one tissue to another as lipoprotein particles by specific carrier proteins called apolipoproteins. Apolipoprotein B (apoB) is an integral and non-exchangeable structural component of lipoprotein particles referred to as chylomicrons, very-low-density lipoprotein (VLDL) and low-density lipoprotein (LDL). ApoB circulates in human plasma as two isoforms, ApoB100 and apoB48. ApoB100 can be converted into ApoB48 by the enzyme APOBEC-1 (ApoB mRNA editing catalytic subunit-1). With the help of auxiliary factors, APOBEC-1 can stop the synthesis (production) of ApoB100 form and start the synthesis of ApoB48 form in cells. ApoB100 and ApoB48 play different roles in lipid metabolism. Various studies indicated that ApoB100-associated lipoproteins (VLDL and LDL) are much more atherogenic than ApoB48-associated lipoproteins.

Stimulating hepatic ApoB mRNA editing is a way to reduce serum LDL through the reduction in synthesis and secretion of ApoB100 containing VLDL. In most mammals (including humans), ApoB mRNA editing is carried out only in the small intestine. Studies found that the presence of substantial editing in liver is associated with a less atherogenic lipoprotein profile compared with animals that do not have liver editing activity. APOBEC-1 is expressed in all tissues that carry out ApoB mRNA editing. Human liver does not express APOBEC-1 but it does express sufficient auxiliary proteins to complement exogenous APOBEC-1 in ApoB mRNA editing in transfected cells. Therefore, induction of editing in human liver reduces apoB100 synthesis and thereby reduce the levels of circulating LDL cholesterol.

Example 4

AID and Context Dependent Inhibitors

The nucleotide analog deoxyzebularine[(1-β-D-2'-deoxyribofuranosyl)pyrimidin-2-one, dZ], in the context of single-stranded (ss) DNA oligonucleotides (or those comparable to FIG. 5) bearing SHM hotspots, is tested as a specific inhibitor of AID, while being inactive on deoxycytidine deaminases (dCDA) essential for pyrimidine metabolism. The in vivo substrate specificity of AID has been already established as the deamination of deoxycytidine (dC) at N4 in the context of single-stranded, but not doublestranded (ds) DNA (Bransteitter, R., et al., (2003) *PNAS USA*, 100, 4102-7; Pham, P., et al. (2003) *Nature*, 424, 103-7; (Ramiro, A. R., et al., (2003) *Nat Immunol*, 4, 452-6; Chaudhuri, J., et al., (2003) *Nature*, 422, 726-30; Dickerson, S. K., et al., (2003) *J Exp Med*, 197, 1291-6). Furthermore, ssDNA deamination demonstrates activity on the SHM consensus sequence WRCY (SEQ ID NO: 19), where W=A or T, R=purine and Y=pyrimidine. By substituting dC with dZ in the context hot spot ssDNA oligos, selectively "poisoning" AID by inhibiting oligo release from its active site is possible. Previously, the use of free dZ and Z were shown to be intracellular inhibitors of mammalian deoxycytidine deaminases and cytidine deaminases involved in pyrimidine metabolism and revealed anti-tumor properties Barchi, J. J., Jr., et al., (2003) *J Enzyme Inhib*, 9, :147-62). Enzymatic inhibition by dZ is derived not only from its ability to mimic the structure and hydrogen bonding properties of dC, but also through its reactivity with the $Zn^{2+}$-dependent enzyme to form 3,4-dihydrodeoxyouridine, a mechanism based transition state mimic that binds the cytidine deaminase active site with a Ki of ~10-12 M. Furthermore, in the context of dsDNA, dZ forms a covalent adduct with DNA methyl transferases Wedekind, J. E., et al., (2003) *Trends in Genet*, 19, 207-16. However, because ssDNAs are targeted by neither deoxycytidine deaminases, cytidine deaminases nor DNA methyl transferases, an oligo of the form 5'-d(XnWRZYXn)-3' (SEQ ID NO: 20) selectively inhibits AID (where X=any nucleotide and n=multiple variable sequences, the nature of which depends on the context required by each deaminase or its auxiliary protein. 'n' is an integer to reflect the length of any flanking nucleotides of identity X.

DNA oligonucleotides are chemically synthesized by use of an Applied Biosystems 392 DNA/RNA synthesizer. Due to the ability of zebularine, methods employ Ultramild CE deoxyphosphoramidites (Glen Research, VA) following the recommendations of the manufacturer. The 2'-deoxyzebularine phosphoramidite can be synthesized by the methods of Zhou and coworkers (Zhou, L., et al., (2002) *J Mol Biol*, 321, 591-9, and refs therein). DNA products are purified by reverse phase HPLC as the DMT-on and DMT-off adducts, as described by Wedekind and McKay (Wedekind, J. E. and D. B. McKay (2000) *Methods Enzymol*, 317, 149-68).

Sequences of dZ-containing oligos are derived from previous work that demonstrated AID is active on ssDNA bearing the SHM hotspot sequence WRCY. Therefore, test and control DNA oligos are of the form: 5'-(RGTW)n[WR(C/Z)Y](RGTW)n 3' (SEQ ID NO: 21), where n=1, 2, 3 or 4; sequences are chosen to minimize secondary structure based on thermodynamic stability calculated with the DNA option of program RNA structure (Mathews, D. H. et al., (2002) *J Mol Biol*, 317, 191-203). AID expressing reporter cell lines is cultured for 1 hr in serum-free medium in the absence or presence of dC- or dZ-containing oligonucleotides at concentrations 10 nM-25 μM, and then transferred back into complete medium. SHM activity is measured by GFP reporter reversion rates; residual toxicity is assessed by measuring cell viability by propidium iodide exclusion. Verification of in vitro activity is followed by in vivo studies on transgenic mice (Jansen, B. and U. Zangemeister-Wittke (2002) *Lancet Oncol*, 3, 672-83; Juliano, R. L. et al., (2000) *Curr Opin Mol Ther*, 2, 297-303) data are available for optimal delivery conditions of antisense nucleotides in mice, resulting in efficient delivery to splenic B lymphocytes (Zhao, Q., et al., (1998) *Antisense Nucleic Acid Drug Dev,* 8, 451-8).

Example 5

CEM15/APOBEC-3G and Context Dependent Inhibitors

Cytidine deaminase inhibitors designed to target CEM15 are tested in cell culture for the purpose of improving retroviral infectivity, which has application to the expression of exogenous nucleic acids and application to laboratory infections. Viral infectivity is measured by use of vif (+) and vif (−) pseudotype viruses and host 293T cells either lacking or expressing the Context Dependent Inhibitor target CEM15. The inhibitory effect of CEM15 on the infectivity of vif+ and vif-HIV-1 particles by transient co-transfection of appropriate HIV-1 proviral DNA and CEM15 expression plasmids has been established (Sheehy, A. M., et al., (2000) *Nature,* 418, 646-50). An assay has been developed using a VSV G-protein pseudotyped lentiviral particles that corroborates prior results on CEM15 infectivity and is amenable to the rapid demarcation of the regions of HIV-1 DNA (or RNA) that are the targets of CEM15 deaminase activity. This methodology can be used in the identification of exact cytidine deaminase inhibitor substrates.

An Env-deleted HIV-1 proviral DNA vector (derived from pNL43; AIDS Reagent Repository) was modified by replacement of Nef with a GFP reporter gene and two in-frame stop codons were inserted that abolished Vif production (pHR-GFPΔvif) (confirmed by western blotting with anti-Vif antibodies (AIDs Reagent Repository). Stable, HA-tagged CEM15 expressing 293T cell lines were selected with puromycin and verified by western blotting with a HA specific monoclonal antibody (HA.11; BabCo). The expression of similar levels of full-length HA-tagged CEM15 (or mutant derivative thereof) are assayed in stable cell lines. Although structural modeling can predict focused mutations that impair deaminase activity without destabilizing the entire protein, expression of the mutants must be verified; the addition of the HA epitope tag has no effect on the ability of CEM15 to suppress infectivity (Sheehy, A. M., et al., (2000) *Nature,* 418, 646-50, 2000). Isogenic HIV-1 pro-viral DNAs are packaged into pseudotyped lentiviral particles by co-transfection with a plasmid encoding the VSV G-protein into 293T cells that lack endogenous CEM15 (−) or expressed wild type CEM15 (+) as controls. The resulting pseudotyped particles containing HIV-1 RNA of near full-length (with only a ~2 kb deletion) were quantified by reverse transcriptase (RT) assay; presence of p24Gag protein content can also be assayed by ELISA to normalize viral particles. A defined number ($1\times10^5$ cpm of RT activity) of these particles were added to target, virus susceptible MT2 cells ($5\times10^5$). To assess their infectivity, the percentage of cells that expressed the GFP indicator gene encoded by the packaged recombinant HIV-1 genome was quantified 24 hours later by flow cytometry (University of Rochester Core Facility). The results (FIG. 6) indicate that the expression of CEM15 in 293T cells resulted in at least a 100-fold decrease in vif (−) viral infectivity compared to particles generated in parental 293T cells. The low level of GFP expression from vif(−), CEM15+ particles is indistinguishable from background fluorescence in control cells [0.2%]. This assay is amenable to the use of existing HIV-1 proviral isotyped vectors that are deleted for different regions and different amounts of the HIV-1 genome. Deleted genes can be provided in trans by co-transfection of suitable expression plasmids. A recent comprehensive examination of viral proteins and host $tRNA^{Lys3}$ derived from vif (−) virions revealed no significant biochemical or priming defects (Gaddis, N. C., et al., (2003) *J Virol,* 77, 5810-20).

The effect of cytidine deaminase inhibitor compounds on CEM15 can be tested by treating one or more of the cell types that express CEM15 with various concentrations of cytidine deaminase inhibitor (of the form in FIG. 5) followed by subsequent infection with HIV-1 pseudotyped virus containing reporter GFP. Within 48 hours post infection, cell culture supernatants containing viral particles are added to HeLa cells to test their infectivity, as evidenced by the appearance of green fluorescent cells in FACS analysis. Reduction or elimination of green fluorescent cells relative to that observed in infections from CEM15 (+) cells HIV-1 vif (−) that were not treated with cytidine deaminase inhibitor compounds are scored as a positive identification of cytidine deaminase inhibitor inhibition of CEM15 deaminase activity. Inhibition of GPF reversion by CEM15 is analogous to CEM15 (+) vif (+) cell/virus phenotype.

Example 6

AID Activity and SHM Specificity in Human Lymphoma Cell Lines

High levels of SHM on reporter constructs are strongly dependent on the presence of Ig cis-acting regulatory elements, such as the Eμ and Eκ enhancers (Betz A G, et al & Neuberger M S. 1994. *Cell* 77: 239-248; Bachl J, & Wabl M. 1996 Immunogenetics 45: 59-64; Bachl J et al. 1998. *Proc Natl Acad Sci USA* 95: 2396-2399 In particular, a GFP-mutant reversion substrate was shown to mutate over an order of magnitude more efficiently in the presence of a linked Eμ enhancer sequence (Bachl, et al., 1999 *Eur J Immunol* 166, 5051-64). This context-dependent specificity of SHM targeting is exploited to test whether lymphoma lines with different phenotypes also display differences in their Ig SHM targeting ability.

A number of lymphoma cell lines have been obtained including SUDHL-4 and 6, OCI Ly-3, -7, -10 and -19. Preliminary RT-PCR expression data on a subset of the lines show that they express different levels of AID mRNA (FIG. 1; wt, 646 bp band); PCR products of different size are also found in at least 4 of 6 lines tested. Interestingly, the Farage line, which is known not to undergo Ig SHM in vitro, displays predominantly the smaller PCR products with little if any wild-type. Two of the alternative products (~940 bp and 530 bp) correspond to the expected sizes for two of the trAID isoforms already described, while the smallest 2 bands are novel. These PCR products are cloned and further characterized.

The role of AID and its isoforms is investigated in this set of lymphoma lines, using assays capable of distinguishing between Ig-targeted and non-Ig-targeted SHM. A modified SHM GFP reversion assay (Bachl J (1999) *Eur. J. Immunol.* 29, 1383-1389; Gabay C. (1999) *Eur J Haematol* 63, 180-191; Bachl J, et al., (2001) *J Immunol* 166, 5051-5057) has been developed. In this highly sensitive and quantitative assay, a mutation creating a stop codon embedded in a SHM hotspot sequence has been introduced in the GFP gene; as SHM targets this sequence, reversion occurs and the reverted cells are detected by their fluorescence.

The assay is modified so that the mutated GFP coding sequence from plasmid pI was transferred under the control of the mouse strong, ubiquitous promoter from the phosphoglycerate kinase-1 (pgk) gene, to generate the pgk-GFP* construct. A 0.7 kb fragment containing the entire Eμ core enhancer was inserted 3' of the pgk polyadenylation site in the variant construct pgk-GFP*-Eμ. These constructs are stably transfected by electroporation in the lymphoma lines as well as the following control lines: —NIH3T3 wild type, as a negative control; —NIH3T3—AID transfectant, as positive control for pgk-GFP* reversion; the hypermutating murine pre-B cell line 18.81 (as positive control for Ig-specific SHM, pgk-GFP*-Eμ reversion).

Cotransfection of a pgk-neo$^r$ antibiotic resistance gene followed by G418 selection is used to identify stably transfected clones. Presence of the GFP gene is assessed by PCR with GFP-specific primers. Individual clones are isolated and expanded (3-4/transfection, tested for comparable transcriptional activity), but large mixed pools of >50 transfectants are also maintained, which are analyzed in parallel to further control for potential integration-dependent effects and other sources of heterogeneity in the clonal transfectants. Reversion rates of reversion are quantified by flow cytometry at different time points, and the SHM activity on Eμ-bearing and non-Eμ-bearing plasmids compared as described by Bachl and colleagues. Sequencing of PCR-amplified GFP fragments from flow-sorted revertant GFP+ cells are used to further characterize the frequency and features of the mutations occurring in the individual lines.

Primary GC-like DLBCL samples have been shown to often display ongoing Ig SHM, while ABC-like DLBCL do not (Lossos I S, et al., (2000) *Proc. Natl. Acad. Sci. USA* 97, 10209-10213). However, this is not necessarily the case for the culture-adapted lymphoma lines described above, which could have diverged from their original phenotypes. Indeed, if non-specific SHM does promote a mutator-like phenotype, it can be expected to emerge during long-term culture even in lines with germinal center origin. Differences among cell lines in the targeting of SHM can be detected, with some lines showing Ig-specific SHM (reversion rate of pgk-GFP*-Eμ>>pgk-GFP*), and others non-Ig-specific SHM (reversion rate of pgk-GFP*-Eμ~pgk-GFP*).

Consistent with data indicating that the Farage line has no ongoing Ig SHM, this line expresses little wtAID mRNA, but instead several shorter isoforms. The Toledo line is known to display significant Ig variable gene heterogeneity, indicative of ongoing, Ig-targeted SHM. By analyzing lines with a range of SHM phenotypes, the role of AID in determining SHM specificity can be established. In particular, the extent by which a mutator phenotype is present in lymphoma lines can be established, and its relationship with the pattern of wtAID and trAID expression elucidated. Moreover, these same cell lines provide valuable model systems for other experiments described below. Lines displaying normal wtAID expression but lack of SHM specificity, suggest defects in AID accessory factors. Such lines represent useful models for the identification of such factors.

Example 7

Effect of AID Isoforms on SHM Targeting

In some primary CLL samples, lack of Ig gene SHM is accompanied by the expression of unusual alternatively spliced forms of AID mRNA; similar mRNAs are also found in some, but not all, lymphomas. If translated, these mRNAs give rise to truncated AID isoforms with extensive alterations or loss of the pseudocatalytic domain. It appears that some of these isoforms affect SHM targeting specificity. This could occur by two alternative mechanisms, either the isoforms act directly as non-specific mutators, or they do so by interfering with wtAID function, by generating heterodimers that are perhaps incapable of properly associating with targeting factors.

cDNAs from human wtAID and for presumptive trAID isoforms have already been cloned as described above; if the variant AID transcripts already identified is found to differ from the expected, CLL sample mRNAs are utilized to isolate the correct cDNAs. All RT-PCR products are first modified to bear protein tags for direct detection by shuttling them into appropriate plasmid vectors (6×His/Xpress- and HA-tag vectors are readily available). Different tags are appended to wtAID vs. trAIDs, to allow for specific immunoprecipitation experiments. The tagged cDNAs are then cloned into retroviral vectors. An effective system for retroviral delivery of wtAID using the MSCV-derived pMIG-IRES-GFP bicistronic vector has been established.

Because the AID functional assays utilize a GFP gain of function reporter, the retroviral vector is modified by replacing GFP with the dsRed2 fluorescent protein coding sequence (Clontech), thereby enabling AID expression detection by immunofluorescent microscopy and flow cytometry in the red channel (pMIG-IRES-Red). Thus, pMIG-IRES-GFP (wtAID) and -Red (both wtAID and trAIDs) vectors are generated. Correct expression of the expected products is tested by transduction of NIH3T3 cells followed by Western blot analysis.

Functional assays on the individual proteins are conducted in pgk-GFP* and pgk-GFP*-EμNIH3T3 reporter cells, transduced with the ds-Red expressing retroviral vectors. Transduced cells are analyzed by flow cytometry, with red fluorescence marking trAID-expressing cells, and green fluorescence showing revertants. Rates of reversion (GFP-positive/Red2-positive) are compared between reporters (pgk-GFP* and pgk-GFP*-Eμ) and between cells expressing wtAID or individual trAIDs. This reveals whether trAIDs retain any intrinsic activity.

The ability of trAIDs to affect wtAID activity and SHM targeting is established by inducing their expression in cell lines already expressing wtAID. Lymphoid cell lines are used expressing endogenous AID and confirmed to undergo Ig-targeted SHM such as the murine 18.81 cell line and one of the lymphoma lines described above. These lines are transduced with the various trAID-Red-encoding retroviral vectors, and SHM specificity measured on the basis of pgk-GFP* and pgk-GFP*-Eμ reversion rates as described above.

If a dominant effect of trAIDs on wtAID activity is observed, such as loss of SHM specificity in double-expressors, an interaction of wtAID and trAIDs is evaluated. NIH3T3 cells are simultaneously transduced with both pMIG-HA/wtAID-IRES-GFP and pMIG-His-Xpress/trAID-IRES-Red vectors; such procedure has been shown to successfully generate double-expressor cells. Double-fluorescent (green/red) cells are enriched by flow cytometry and expanded. To demonstrate heterodimerization, total cell protein lysates are prepared and reciprocal immunoprecipitation reactions are performed with anti-HA of anti-Xpress antibodies, according to the manufacturer's protocols. Immunoprecipitated products are separated by SDS-PAGE gels, and blotted onto nitrocellulose filters. The filters are detected with either anti-HA or anti-Xpress antibodies, followed by an HRP-conjugated secondary antibody and visualization by the West Pico Super Signal Chemiluminescent substrate (Pierce).

Unlike the murine lines described above, human lymphoma cell lines require a slightly more complex retroviral transduction protocol. Briefly, the pMIG retroviral vector DNAs are first transfected by lipofection into the Phoenixampho packaging cell line, and the retroviral supernatants derived from this first packaging cycle are then used to transduce the RD114 packaging cell line, which generates retroviruses with a Feline Leukemia Virus envelope able to efficiently transduce human cells. This "ping-pong," sequential packaging method is required for maximum yields because the RD114 cell line does not transfect efficiently enough to be used directly. Retroviral supernatants from the second packaging cycle are then used for human cell line transduction; the infection rate in human lymphoma lines routinely averages from 20 to over 80% (FIG. 3).

Example 8

AID's Oncogenic Role in B Cell Neoplasias

The finding of T cell lymphomas and pulmonary adenomas in AID transgenics confirms the oncogenicity of AID. These transgenics did not acquire B cell malignancies, raising the question of whether AID expression in fact plays a pathogenetic role in B cell neoplasias. B cells can be tested to determine if they have the potential to be transformed through A/D-mediated oncogenesis, whether this is associated with initiation of tumorigenesis, and/or if AID expression only contributes to neoplastic progression.

In human activated B cell-like DLBCL, the presence of mutations in Ig genes suggests a post-germinal center origin. Sustained AID transcription in the absence of ongoing Ig SHM, coupled with the frequent finding of SHM-like oncogene mutations in these cells, clearly suggest a deregulation of AID targeting. To investigate AID's effects on B lymphocytes, as models of human lymphomagenesis, transgenic mice are generated that replicate the AID expression pattern observed in human ABC-like DLBCL.

The immunoglobulin IgH 3' enhancer element (3'EH) is involved in the regulation of immunoglobulin gene expression and class switch recombination during B cell activation and terminal B cell differentiation. When linked to an Ig variable region promoter, the 3'EH hs (1,2) element has been shown to reliably direct transgene expression specifically in activated B cells and plasma cells. A transgenic expression vector containing the murine VH186.2 promoter and the 3'EH hs(1,2) enhancer is available. His-tagged wtAID cDNA is cloned into this vector (3'E-AID construct), and transgenic mice are generated by pronuclear microinjection of C57Bl/6 zygotes.

Transgenic mice are identified by PCR for the fusion gene containing AID cDNA and the human γ-globin 3'UTR/poly-A site present in the vector. Appropriate expression of the transgene in activated B cells will be established by RT-PCR on flow-sorted B cell subpopulations (resting, B220+, IgD$^{hi}$IgM$^{lo}$ B cells; germinal center B220+/GL7+ cells; plasma cells, large B220$^{lo}$, CD43+, sIg-cells) and by immunohistochemistry on splenic section using the anti-Xpress mAb and counterstains for GC cells (PNA+) and plasma cells (cytoplasmic Ig$^{hi}$). Transgene inducibility are also verified in vitro by culture of primary splenic B cells with activators (LPS, 20 μg/ml; anti-CD40 clone HM40-3, 2 μg/ml) known to induce 3'EH activity, followed by RT-PCR and Western blotting at different time points (day 0, 1, 2, 4 of activation). Transgenic AID activity are functionally assessed by breeding the 3'E-AID transgenics with AID-deficient mice; if AID activity is present, at least partial complementation of the defect in SHM and CSR is observed in these mice. 3'E-AID/ A/D-/- mice are evaluated for their ability to undergo SHM by VH region sequencing using primers for Ig VHJ558 segments following sheep red blood cell immunization, and class switching by ELISA on pre- and post-immunization serum.

The ability of transgenic AID expression to induce B cell neoplasias is evaluated by monitoring the health status of transgenics as they age. Mice displaying signs of ongoing disease (cachexia, lack of activity, fur loss, hunched posture, etc) are sacrificed and their lymphoid tissues (bone marrow, spleen, peripheral and mesenteric lymph nodes and Peyer's patches) analyzed histologically and by flow cytometry with an array of antibodies specific to B cell- (CD19, CD21, CD23, IgM, IgD, Igκ/λ, GL-7), T cell- (CD3ε, CD4, CD8) and myeloid markers (Mac-1, Gr-1). Signs of B lymphoid expansion can be monitored; if this is observed, emergent clonality is established by Southern blot analysis of Ig gene rearrangements in the tissue's genomic DNA.

To distinguish potential effects of AID as a progression factor, transgenic mice are bred onto genetic backgrounds already predisposed to B cell lymphoma development. Initially, Eμ-bcl2 transgenic mice are used. This transgene results in rare, late (>12 months) lymphomas on a normal background, but dramatically accelerates lymphomagenesis when combined with another transgenic oncogene, such as Eμ-c-myc, suggesting that accumulation of multiple secondary mutagenic hits is required for disease progression in these mice. By generating double transgenics, any potential effect of AID expression in accelerating lymphoma development is established. In addition, should the effect of AID in the bcl2 background be weak, breeding with Eμ-c-myc transgenic mice, which display a more aggressive baseline phenotype, can also be used.

3'EH-hs(1,2)-dependent constructs are known to reliably express in activated B cells. The availability of AID-deficient mice allows the unequivocal determination of transgene expression and activity. Evidence of B cell malignancies following sustained AID expression, either as a primary event (in a normal background), or as a progression factor (in lymphoma-susceptible backgrounds) confirms that B lineage cells can be targets of AID-mediated transformation, and provide a valuable model for the study of the mechanisms of human AID-mediated lymphomagenesis. Lack of a cancer phenotype also can represent an informative result, as it suggests either an intrinsic protection of B lymphocytes against SHM mistargeting, or more likely, based on the strong evidence for SHM-like oncogene mutations in human lymphomagenesis, a role for still unidentified SHM effectors downstream of AID.

Example 9

Molecular Identification of Non-Ig Gene AID Targets in Lymphomas

A small number of oncogenes (c-myc, Pim1, Pax5, RhoH/TTF) have been found to bear hallmarks of SHM in human lymphoma samples. Additional important targets can exist whose mutation contributes to neoplastic development. In this experiment, a mutation screening method based on a genetic selection strategy that exploits bacterial DNA mismatch repair is used. This method has been used to identify single nucleotide polymorphism in human genomic DNA and has been modified herein.

These experiments take advantage of the mismatch repair detection (MRD) system, a novel, high-throughput bacterial positive genetic selection strategy for human disease related single nucleotide polymorphisms. In this example, the selection system is used as it was originally intended for screen mismatches in genomic DNA sequences.

Genomic DNA isolated from a non-B cell source (e.g. fibroblasts) and from lymphomas from AID-transgenic mice is digested with DpnII (average size ~0.3 kb) and cloned separately into two different plasmids. Unmethylated plasmids (grown in a dam methylase-deficient E. coli strain) containing the 'control' inserts (from normal tissue DNA) also encode an intact Cre recombinase, whereas the methylated plasmids contain putative mutated fragments from lymphoma cells and encode an inactive 5 nucleotide deletion mutant of Cre. Heteroduplexes formed in vitro between the two plasmid libraries by melting and reannealing are transformed into a bacterial strain that harbors an F' episome carrying a 'floxed' tetracycline resistance gene. Repair of the mismatch uses the methylated strand as template, resulting in loss of the functional Cre recombinase gene and retention of the 'floxed' tetracycline resistance gene. Non-mismatched heteroduplexes, instead, induce no repair, express functional Cre, and result in $Tet^R$. LoxP-mediated deletion. The $Tet^R$ clones obtained through the MRD process therefore contain exclusively fragments displaying sequence heterogeneity between the original samples, and will be subject to further selection and identification steps.

Example 10

Deaminase Inhibitors as Agents for AID-Targeted Pharmacological Intervention

AID, like other cytidine deaminases, is known to be inhibited by $Zn^{2+}$ chelation. It has previously been shown that two types of $Zn^{2+}$ chelators and metalloenzyme inhibitors, tetracyclines and hydroxamates, display a remarkable ability to inhibit CSR in vitro at therapeutic concentrations. Tetracyclines also inhibit antibody responses in vivo. Although A/D mRNA expression was not affected by tetracycline treatment in vitro), the possibility exists that the observed inhibitory activity reflected an indirect effect on CSR, rather than a direct inhibition of AID function. Because both tetracyclines and hydroxamates (and especially the former) are available drugs which could, if necessary, be rapidly applied in a clinical setting, they can be tested to determine if they are capable of directly inhibiting AID function in the model systems described above.

The same reporter cells lines and assays are used as described in Example 9. A/D activity on the GFP reversion assay is assayed in cells cultured in the presence of increasing concentrations of doxycycline (1-10 µg/ml) and the KB8301 hydroxamate (5-50 µM) (Becton Dickinson). Importantly, the assays are performed on cells expressing both endogenous (18.81, lymphoma lines) as well as exogenous AID (NIH3T3 transfectants); this controls for the possibility that either drug can act on some other component of the B cell SHM/CSR activation pathway (which is absent in NIH3T3). Assuming inhibition will be observed in all systems, additional agents are tested, including other tetracyclines and FDA-approved non-antibiotic tetracycline analogs (CMT series, from Collagenex Pharmaceuticals), as well as hydroxamates approved for cancer therapy, such as marimastat/BB2516/TA2516 (British Biotech/Schering Plough). The optimal agents, based on inhibitory activity and known pharmacological properties, can then be tested in the AID transgenic mice derived in Example 7, if appropriate, to establish their ability to arrest of delay tumor onset and/or progression.

Example 11

Making Peptide-Oligo Conjugates

One method of making a peptide-oligo conjugate is to use Fmoc chemistry and synthesize the peptide from an oligo synthesized on amino-CPG. Deprotection of peptides synthesized using Fmoc chemistry requires 50% TFA and t-boc synthesized peptides require HF. Another method is to use a heterobifunctional crosslinking reagent to link a synthetic peptide, containing an N-terminal lysine, to a 5'-Thiol modified oligo or conversely a 5'-amino modified oligo to a cysteine containing peptide. An example of a crosslinking reagent is N-Maleimido-6-aminocaproyl-(2'-nitro, 4'-sulfonic acid)-phenyl ester. Na+ (mal-sac-HNSA) from Bachem Bioscience (cat. # Q-1615). Reaction of this crosslinker with an amino group releases the dianion phenolate, 1-hydroxy-2-nitro-4-benzene sulfonic acid a yellow chromophore. The chromophore allows both quantitation of the coupling reaction as well as act as an aid in monitoring the separation of activated peptide from free crosslinking reagent using gel filtration.

Method A: Couple Peptide Amine to Oligo Thiol (Peptide MW should be >5,000 to be Excluded from Desalting Column).

The following is an example of one method that can be used to couple a peptide amine to an oligo thiol. Step 1: Synthesize a peptide with an N-terminal, or internal, lysine (The epsilon amino group is more reactive than an alpha amino group). This can be done for the TAT peptide. Step 2: Synthesize an oligonucleotide with a 5' Thiol group. These are available from Glen Research. Step 3: React peptide with excess mal-sac-HNSA (pH 7.5 Sodium phosphate). Step 4: Separation of peptide-mal-sac conjugate from free crosslinker and buffer exchange (pH 6.0 Sodium phosphate) using a gel filtration column (NAP or eq.). (Peptide must be large enough to separate from the free linker which can be visualized as a yellow band. Do not collect yellow band with peptide. Step 5: Activate thiol modified oligo, desalt and buffer exchange (pH 6 Sodium phosphate) on NAP 5 column. Step 6: React activated peptide with Thiol modified oligo. Step 7: Purify Peptide-Oligo conjugate by ion exchange chromatography on Nucleogen DEAE-500-10 or eq. Elution order: free peptide, peptide-oligo, free oligo.

Method B: Couple Oligo Amine to Peptide Cysteine (Oligos>15mers are Excluded from Desalting Column).

The following is an example of one method that can be used to couple an oligo amine to a peptide cysteine. Use above procedure switching oligo for peptide. Step 1: Synthesize a peptide with an N-terminal, or internal, cysteine. In this method, Tat is a basic protein with numerous reactive lysine side-chains. Step 2: Synthesize an oligonucleotide with a 5' amino modifier. Step 3: Purify oligo Trityl-on by RP HPLC or cartridge. Step 4: React oligo with excess mal-sac-HNSA (pH 7.5 Sodium phosphate). Step 5: Separation of oligo-mal-sac conjugate from free crosslinker and buffer exchange (pH 6 Sodium phosphate) using a gel filtration column (NAP or eq.). Note oligo must be large enough to separate from the free linker which can be visualized as a yellow band. Do not collect yellow band with oligo. Step 6: Dissolve peptide in pH 6.0 Sodium phosphate buffer and react with activated oligo. Step 7: Purify Peptide-Oligo conjugate by ion exchange chromatography on Nucleogen DEAE-500-10 or eq. Elution order: free peptide, peptide-oligo, free oligo.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

1. Kim, C. H., et al., *Synthesis of pyrimidin-2-one nucleosides as acid-stable inhibitors of cytidine deaminase.* J Med Chem, 1986. 29(8): p. 1374-80.
2. Laliberte, J., V. E. Marquez, and R. L. Momparler, *Potent inhibitors for the deamination of cytosine arabinoside and 5-aza-2'-deoxycytidine by human cytidine deaminase.* Cancer Chemother Pharmacol, 1992. 30(1): p. 7-11.
3. Driscoll, J. S., et al., *Antitumor properties of 2(1H)-pyrimidinone riboside (zebularine) and its fluorinated analogues.* J Med Chem, 1991. 34(11): p. 3280-4.
4. Xiang, S., et al., *The structure of the cytidine deaminase-product complex provides evidence for efficient proton transfer and ground-state destabilization.* Biochemistry, 1997. 36(16): p. 4768-74.
5. Xiang, S., et al., *Cytidine deaminase complexed to 3-deazacytidine: a "valence buffer" in zinc enzyme catalysis.* Biochemistry, 1996. 35(5): p. 1335-41.
6. Xiang, S., et al. *Transition-state selectivity for a single hydroxyl group during catalysis by cytidine deaminase.* Biochemistry, 1995. 34(14): p. 4516-23.
7. Frick, L., et al., *Binding of pyrimidin-2-one ribonucleoside by cytidine deaminase as the transition-state analogue 3,4-dihydrouridine and the contribution of the 4-hydroxyl group to its binding affinity.* Biochemistry, 1989. 28(24): p. 9423-30.
8. Foubister, V., *Drug reactivates genes to inhibit cancer.* Drug Discov Today, 2003. 8(10): p. 430-1.
9. Barchi, J. J., Jr., S. Musser, and V. E. Marquez, *The decomposition of 1-(beta-D-ribofuranosyl)-1,2-dihydropyrimidin-2-one (zebularine) in alkali: mechanism and products.* J. Organic Chem., 1992. 57: p. 536-541.
10. Kelley, J. A., et al., *Furanose-pyranose isomerization of reduced pyrimidine and cyclic urea ribosides.* J Med Chem, 1986. 29(11): p. 2351-8.
11. Cheng, J. C., et al., *Inhibition of DNA methylation and reactivation of silenced genes by zebularine.* J Natl Cancer Inst, 2003. 95(5): p. 399-409.
12. Zhou, L., et al., *Zebularine: a novel DNA methylation inhibitor that forms a covalent complex with DNA methyltransferases.* J Mol Biol, 2002. 321(4): p. 591-9.
13. Wedekind, J. E., et al., *Messenger RNA editing in mammals: new members of the APOBEC family seeking roles in the family business.* Trends Genet, 2003. 19(4): p. 207-16.
14. Mehta, A., et al., *Molecular cloning of apobec-1 complementation factor, a novel RNA-binding protein involved in the editing of apolipoprotein B mRNA.* Mol Cell Biol, 2000. 20(5): p. 1846-54.
15. Smith, H. C., *Apolipoprotein B mRNA editing: the sequence to the event.* Semin Cell Biol, 1993. 4(4): p. 267-78.
16. Mehta, A. and D. M. Driscoll, *Identification of domains in apobec-1 complementation factor required for RNA binding and apolipoprotein-B mRNA editing.* Rna, 2002. 8(1): p. 69-82.
17. Blanc, V., et al., *Mutagenesis of apobec-1 complementation factor reveals distinct domains that modulate RNA binding, protein-protein interaction with apobec-1', and complementation of C to U RNA-editing activity.* J Biol Chem, 2001. 276(49): p. 46386-93.
18. Dance, G. S., et al., *Identification of the yeast cytidine deaminase CDD1 as an orphan C->U RNA editase.* Nucleic Acids Res, 2001. 29(8): p. 1772-80.
19. Anant, S., et al., *ARCD-1, an apobec-1-related cytidine deaminase, exerts a dominant negative effect on C to U RNA editing.* Am J Physiol Cell Physiol, 2001. 281-(6): p. C1904-16
20. Jarmuz, A., et al., *An anthropoid-specific locus of orphan C to U RNA-editing enzymes on chromosome 22.* Genomics, 2002. 79(3): p. 285-96.
21. Muramatsu, M., et al., *Specific expression of activation-induced cytidine deaminase (AID), a novel member of the RNA-editing deaminase family in germinal center B cells.* J Biol Chem, 1999. 274(26): p. 18470-6.
22. Muramatsu, M., et al., *Class switch recombination and hypermutation require activation-induced cytidine deaminase (AID), a potential RNA editing enzyme.* Cell, 2000. 102(5): p. 553-63.
23. Revy, P., et al., *Activation-induced cytidine deaminase (AID) deficiency causes the autosomal recessive form of the Hyper-IgM syndrome (HIGM2).* Cell, 2000. 102(5): p. 565-75.
24. Petersen-Mahrt, S. K., R. S. Harris, and M. S. Neuberger, *AID mutates E. coli suggesting a DNA deamination mechanism for antibody diversification.* Nature, 2002. 418(6893): p. 99-103.
25. Harris, R. S., S. K. Petersen-Mahrt, and M. S. Neuberger, *RNA editing enzyme APOBEC1 and some of its homologs can act as DNA mutators.* Mol Cell, 2002. 10(5): p. 1247-53.
26. Greeve, J., et al., *Expression of activation-induced cytidine deaminase in human B-cell non-Hodgkin lymphomas.* Blood, 2003. 101(9): p. 3574-80.
27. McCarthy, H., et al., *High expression of activation-induced cytidine deaminase (AID) and splice variants is a distinctive feature of poor-prognosis chronic lymphocytic leukemia.* Blood, 2003. 101(12): p. 4903-8.
28. Oppezzo, P., et al., *Chronic lymphocytic leukemia B cells expressing AID display dissociation between class switch recombination and somatic hypermutation.* Blood, 2003. 101(10): p. 4029-32.
29. Damle, R. N., et al., *Ig V gene mutation status and CD38 expression as novel prognostic indicators in chronic lymphocytic leukemia.* Blood, 1999. 94(6): p. 1840-7.
30. Hamblin, T. J., et al., *Unmutated Ig V(H) genes are associated with a more aggressive form of chronic lymphocytic leukemia.* Blood, 1999. 94(6): p. 1848-54.
31. Lossos, I. S., et al., *Ongoing immunoglobulin somatic mutation in germinal center B cell-like but not in activated B cell-like diffuse large cell lymphomas.* Proc Natl Acad Sci USA, 2000. 97(18): p. 10209-13.
32. Rosenwald, A., et al., *The use of molecular profiling to predict survival after chemotherapy for diffuse large-B-cell lymphoma.* N Engl J Med, 2002. 346(25): p. 1937-47.
33. Alizadeh, A. A., et al., *Distinct types of diffuse large B-cell lymphoma identified by gene expression profiling.* Nature, 2000. 403(6769): p. 503-11.
34. Okazaki, I. M., et al., *Constitutive expression of AID leads to tumorigenesis.* J Exp Med, 2003. 197(9): p. 1173-81.
35. Mangeat, B., et al., *Broad antiretroviral defense by human APOBEC3G through lethal editing of nascent reverse transcripts.* Nature, 2003.
36. Fisher, A. G., et al., *The sor gene of HIV-1 is required for efficient virus transmission in vitro.* Science, 1987. 237 (4817): p. 888-93.

37. Strebel, K., et al., *The HIV 'A' (sor) gene product is essential for virus infectivity*. Nature, 1987. 328(6132): p. 728-30.

38. Simon, J. H., et al., *Evidence for a newly discovered cellular anti-HIV-1 phenotype*. Nat Med, 1998. 4(12): p. 1397-400.

39. Madani, N. and D. Kabat, *An endogenous inhibitor of human immunodeficiency virus in human lymphocytes is overcome by the viral Vif protein*. J Virol, 1998. 72(12): p. 10251-5.

40. Courcoul, M., et al., *Peripheral blood mononuclear cells produce normal amounts of defective Vif-human immunodeficiency virus type 1 particles which are restricted for the preretrotranscription steps*. J Virol, 1995. 69(4): p. 2068-74.

41. Simon, J. H. and M. H. Malim, *The human immunodeficiency virus type I Vif protein modulates the postpenetration stability of viral nucleoprotein complexes*. J Virol, 1996. 70(8): p. 5297-305.

42. von Schwedler, U., et al., *Vif is crucial for human immunodeficiency virus type I proviral DNA synthesis in infected cells*. J Virol, 1993. 67(8): p. 4945-55.

43. Sova, P. and D. J. Volsky, *Efficiency of viral DNA synthesis during infection of permissive and nonpermissive cells with vif-negative human immunodeficiency virus type 1*. J Virol, 1993. 67(10): p. 6322-6.

44. Sheehy, A. M., et al., *Isolation of a human gene that inhibits HIV-1 infection and is suppressed by the viral Vif protein*. Nature, 2002. 418(6898): p. 646-50.

45. Camaur, D. and D. Trono, *Characterization of human immunodeficiency virus type 1 Vif particle incorporation*. J Virol, 1996. 70(9): p. 6106-11.

46. Liu, H., et al., *The Vif protein of human and simian immunodeficiency viruses is packaged into virions and associates with viral core structures*. J Virol, 1995. 69(12): p. 7630-8.

47. Logan, A. C., C. Lutzko, and D. B. Kohn, *Advances in lentiviral vector design for gene-modification of hematopoietic stem cells*. Curr Opin Biotechnol, 2002. 13(5): p. 429-36.

48. Chang, L. J. and E. E. Gay, *The molecular genetics of lentiviral vectors—current and future perspectives*. Curr Gene Ther, 2001. 1(3): p. 237-51.

49. Skuse, G. R., et al., *The neurofibromatosis type I messenger RNA undergoes base-modification RNA editing*. Nucleic Acids Res, 1996. 24(3): p. 478-85.

50. Mukhopadhyay, D., et al., *C->U editing of neurofibromatosis I mRNA occurs in tumors that express both the type II transcript and apobec-1, the catalytic subunit of the apolipoprotein B mRNA-editing enzyme*. Am J Hum Genet, 2002. 70(1): p. 38-50.

51. Sowden, M., J. K. Hamm, and H. C. Smith, *Overexpression of APOBEC-1 results in mooring sequence-dependent promiscuous RNA editing*. J Biol Chem, 1996. 271(6): p. 3011-7.

52. Yamanaka, S., et al., *Apolipoprotein B mRNA-editing protein induces hepatocellular carcinoma and dysplasia in transgenic animals*. Proc Natl Acad Sci USA, 1995. 92(18): p. 8483-7.

53. Anant, S. and N. O. Davidson, *An AU-rich sequence element (UUUN[A/U]U) downstream of the edited C in apolipoprotein B mRNA is a high-affinity binding site for Apobec-1: binding of Apobec-1 to this motif in the 3' untranslated region of c-myc increases mRNA stability*. Mol Cell Biol, 2000. 20(6): p. 1982-92.

54. Bransteitter, R., et al., *Activation-induced cytidine deaminase deaminates deoxycylidine on single-stranded DNA but requires the action of RNase*. Proc Natl Acad Sci USA, 2003. 100(7): p. 4102-7.

55. Pham, P., et al., *Processive AID-catalysed cytosine deamination on single-stranded DNA simulates somatic hypermutation*. Nature, 2003.

56. Ramiro, A. R., et al., *Transcription enhances AID-mediated cytidine deamination by exposing single-stranded DNA on the nontemplate strand*. Nat Immunol, 2003. 4(5): p. 452-6.

57. Chaudhuri, J., et al., *Transcription-targeted DNA deamination by the AID antibody diversification enzyme*. Nature, 2003. 422(6933): p. 726-30.

58. Dickerson, S. K., et al., *AID mediates hypermutation by deaminating single stranded DNA*. J Exp Med, 2003. 197 (10): p. 1291-6.

59. Barchi, J. J., Jr., et al., *Improved synthesis of zebularine [1-(beta-D-ribofuranosyl)-dihydropyrimidin-2-one] nucleotides as inhibitors of human deoxycytidylate deaminase*. J Enzyme Inhib, 1995. 9(2): p. 147-62.

60. Wedekind, J. E. and D. B. McKay, *Purification, crystallization, and X-ray diffraction analysis of small ribozymes*. Methods Enzymol, 2000. 317: p. 149-68.

61. Mathews, D. H. and D. H. Turner, *Dynalign: an algorithm for finding the secondary structure common to two RNA sequences*. J Mol Biol, 2002. 317(2): p. 191-203.

62. Jansen, B. and U. Zangemeister-Wittke, *Antisense therapy for cancer—the time of truth*. Lancet Oncol, 2002. 3(11): p. 672-83.

63. Juliano, R. L. and H. Yoo, *Aspects of the transport and delivery of antisense oligonucleotides*. Curr Opin Mol Ther, 2000. 2(3): p. 297-303.

64. Zhao, Q., et al., *Cellular distribution of phosphorothioate oligonucleotide following intravenous administration in mice*. Antisense Nucleic Acid Drug Dev, 1998. 8(6): p. 451-8.

65. Gaddis, N. C., et al., *Comprehensive investigation of the molecular defect in vif-deficient human immunodeficiency virus type 1 virions*. J Virol, 2003. 77(10): p. 5810-20.

66. Yu, K., et al., (2003). *J. Biol. Chem*. 279, 6496-6500.

67. Arakawa, H. et al., *Requirement of the Activation-Induced Deaminase (AID) Gene for Immunoglobulin Gene Conversion*. Science, 2002. 295: 1301-6.

68. Doi, T. et al. *Inaugural Article: De novo protein synthesis is required for the activation-induced cytidine deaminase function in class-switch recombination* PNAS, March 2003. 100:2634-2638.

69. Eto, T. et al. *RNA-editing cytidine deaminase Apobec-1 is unable to induce somatic hypermutation in mammalian cell* PNAS, October 2003; 100:12895-12898.

70. Dance, G. et al. *APOBEC-1 dependent cytidine to uridine editing of apolipoprotein B RNA in yeast*. Nucleic Acids Res., January 2000; 28: 424-429.

71. Corsetti, J P, et al. *Metabolic syndrome best defines the multivariate distribution of blood variables in postinfarction patients* Atherosclerosis, December 2003; 171(2): 351-8.

72. Moss, A. J. (1999) *Circulation* 99, 2517-22).

72. Backus, J. W. (1990) *Biochem. Biophys. Res. Commun*. 170, 513-8.

73. Greeve, J. (2003) *J. Lipid Res*. 34, 1367-83.

74. Farese, Jr. R V et al. *Phenotypic analysis of mice expressing exclusively apolipoprotein B48 or apolipoprotein B100* PNAS, June 1996; 93: 6393-6398

75. Nakamuta, M. et al. *Complete Phenotypic Characterization of apobec-1 Knockout Mice with a Wild-type Genetic*

Background and a Human Apolipoprotein B Transgenic Background, and Restoration of Apolipoprotein B mRNA Editing by Somatic Gene Transfer of Apobec-1 J. Biol. Chem., October 1996; 271: 25981-25988.
76. Barbon, A. et al., Glutamate *receptor RNA editing: a molecular analysis of GluR2, GluR5 and GluR6 in human brain tissues and in NT2 cells following in vitro neural differentiation*. Brain Res. Mol. Brain. Res, October 2003; 117(2):168-78.
77. Sowden et al., (2000) *J. Cell Sci.* 115, 1027-39.
78. Zhang et al., *The cytidine deaminase CEM15 induces hypermutation in newly synthesized HIV-1 DNA*. Nature, July 2003; 424(6944): 94-8.
79. Lecossier et al., *Hypermutation of HIV-1 DNA in the Absence of the Vif Protein* Science, May 2003; 300: 1112.
80. George, C. X. & Samuel, C. E. *Human RNA-specific adenosine deaminase ADAR1 transcripts possess alternative exon 1 structures that initiate from different promoters, one constitutively active and the other interferon inducible* PNAS, April 1999; 96: 4621-4626.
81. Jayan, G. C. & Casey, J. I. *Inhibition of Hepatitis Delta Virus RNA Editing by Short Inhibitory RNA-Mediated Knockdown of ADAR1 but Not ADAR2 Expression* J. Virol., December 2002; 76: 12399-12404.
82. Casey, J. L. *RNA Editing in Hepatitis Delta Virus Genotype III Requires a Branched Double-Hairpin RNA Structure* J. Virol., August 2002; 76: 7385-7397.
83. Y. Z. Xu and E. T. Kool, Tetrahedron Lett., 1997, 38, 5595-5598.
84. Mariani, R. et al. *Species-specific exclusion of APOBEC3 G from HIV-1 virions by Vif.* Cell, July 2003; 114(1): 21-31.
85. Stopak, K. et al., *HIV-1 Vif blocks the antiviral activity of APOBEC3G by impairing both its translation and intracellular stability*. Mol Cell, September 2003; 12(3): 591-601.
86. Ohagen, A. and Gabuzda, D. *Role of Vif in Stability of the Human Immunodeficiency Virus Type I Core* J. Virol., December 2000; 74: 11055-11066
87. Zhang, H. et al., *Human Immunodeficiency Virus Type 1 Vif Protein Is an Integral Component of an mRNP Complex of Viral RNA and Could Be Involved in the Viral RNA Folding and Packaging Process* J. Virol., September 2000; 74: 8252-8261
88. Khan, M. A. et al., *Human Immunodeficiency Virus Type 1 Vif Protein Is Packaged into the Nucleoprotein Complex through an Interaction with Viral Genomic RNA* J. Virol., August 2001; 75: 7252-7265
89. Liu, B. et al., *Influence of Primate Lentiviral Vif and Proteasome Inhibitors on Human Immunodeficiency Virus Type I Virion Packaging of APOBEC3G* J. Virol., February 2004; 78: 2072-2081
90. Sheehy, A. M. et al., (2003) *Nat. Med.* 9, 1404-7.
91. Lambert, G. et al., *Nanoparticulate systems for the delivery of antisense oligonucleotides*. Adv Drug Deliv Rev, March 2001; 47(1): 99-112
92. Bachl, J. *Hypermutation targets a green fluorescent protein-encoding transgene in the presence of immunoglobulin enhancers*. Eur J Immunol, April 1999; 29(4): 1383-9
93. Gabay, C. *Somatic mutations and intraclonal variations in the rearranged Vkappa genes of B-non-Hodgkin's lymphoma cell lines*. Eur J Haematol, September 1999; 63(3):
94. Bachl, J. et al., *Increased Transcription Levels Induce Higher Mutation Rates in a Hypermutating Cell Line* J. Immunol., April 2001; 166: 5051-5057

---

What is claimed is:

1. A context-dependent cytidine deaminase inhibitor comprising a nucleoside incorporated in a polymeric substrate, wherein the polymeric substrate selectively targets a cytidine deaminase, further wherein the polymeric substrate comprises a mooring sequence.

2. The context-dependent cytidine deaminase inhibitor of claim 1, wherein the nucleoside comprises a base, wherein the base of the nucleoside is susceptible to nucleophilic attack.

3. The context-dependent cytidine deaminase inhibitor of claim 1, wherein the nucleoside comprises a base, wherein the base of the nucleoside comprises a sp2 carbon center susceptible to nucleophilic attack.

4. The context-dependent cytidine deaminase inhibitor of claim 3, wherein an electrophilic group is present at the sp2 carbon center.

5. The context-dependent cytidine deaminase inhibitor of claim 3, wherein the Sp2 carbon center is a carbonyl group, an imino group, or an alkenyl group.

6. The context-dependent cytidine deaminase inhibitor of claim 1, wherein the nucleoside is susceptible to nucleophilic attack by a metal-bound hydroxide.

7. The context-dependent cytidine deaminase inhibitor of claim 6, wherein the metal-bound hydroxide is zinc hydroxide.

8. The context-dependent cytidine deaminase inhibitor of claim 1, wherein the nucleoside comprises a pyrimidine.

9. The context-dependent cytidine deaminase inhibitor of claim 1, wherein when the nucleoside comprises a pyrimidine, and wherein nucleophilic attack occurs at C4 of the pyrimidine.

10. The context-dependent cytidine deaminase inhibitor of claim 9, wherein the pyrimidine has an electron-withdrawing group at C4.

11. The context-dependent cytidine deaminase inhibitor of claim 1, wherein the nucleoside comprises a base, wherein the base of the nucleoside has at least one Sp3 carbon center.

12. The context-dependent cytidine deaminase inhibitor of claim 11, wherein the sp3 carbon center has at least one —OR group, wherein R is hydrogen, alkyl, aryl, aralkyl, alkenyl, alkynyl, or acyl.

13. The context-dependent cytidine deaminase inhibitor of claim 1, wherein when the nucleoside comprises a pyrimidine, the nucleoside comprises a sp3 carbon center at C4 of the pyrimidine.

14. The context-dependent cytidine deaminase inhibitor of claim 1, wherein the nucleoside comprises a base, wherein the base of the nucleoside comprises at least one group capable of hydrogen bonding.

15. The context-dependent cytidine deaminase inhibitor of claim 1, wherein the nucleoside is selected from the group consisting of 4-fluorozebularine, 2'-deoxy, 2'-fluorozebularine, 3,4,5,6-tetrahydro-2'-deoxyuridine, nebularine; 8-azanebularine; coformycin; or zebularine.

16. The context-dependent cytidine deaminase inhibitor of claim 1, wherein the polymeric substrate comprises oligonucleotide residues.

17. The context-dependent cytidine deaminase inhibitor of claim 1, wherein the targeted cytidine deaminase is APOBEC-1.

18. The context-dependent cytidine deaminase inhibitor of claim 1, wherein the targeted cytidine deaminase is AID.

19. The context-dependent cytidine deaminase inhibitor of claim 18, comprising WRZY, wherein W is Adenine or Thymine, wherein R is a purine, wherein Z is the nucleoside, and wherein Y is a pyrimidine.

20. The context-dependent cytidine deaminase inhibitor of claim 1, wherein the targeted cytidine deaminase is CEM15.

21. A composition comprising the context-dependent cytidine deaminase inhibitor of claim 1 and a pharmaceutical carrier.

22. A cell comprising the context-dependent cytidine deaminase inhibitor of claim 1.

23. The context-dependent cytidine deaminase inhibitor of claim 1, wherein the targeted cytidine deaminase is APOBEC-3F.

24. The context-dependent cytidine deaminase inhibitor of claim 1, wherein the targeted cytidine deaminase is APOBEC-3B.

* * * * *

UNITED STATES PATENT AND TRADEMARK OFFICE
CERTIFICATE OF CORRECTION

| | | |
|---|---|---|
| PATENT NO. | : 8,158,770 B2 | |
| APPLICATION NO. | : 11/579660 | |
| DATED | : April 17, 2012 | |
| INVENTOR(S) | : Wedekind and Smith | |

It is certified that error appears in the above-identified patent and that said Letters Patent is hereby corrected as shown below:

Title page, item (54), and col. 1 the title should read:

-- CONTEXT DEPENDENT INHIBITORS OF CYTIDINE DEAMINASES AND USES THEREOF --

Signed and Sealed this
Nineteenth Day of June, 2012

David J. Kappos
*Director of the United States Patent and Trademark Office*

SEQUENCE LISTING

```
<160> NUMBER OF SEQ ID NOS: 22

<210> SEQ ID NO 1
<211> LENGTH: 236
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 1

Met Thr Ser Glu Lys Gly Pro Ser Thr Gly Asp Pro Thr Leu Arg Arg
1               5                   10                  15

Arg Ile Glu Pro Trp Glu Phe Asp Val Phe Tyr Asp Pro Arg Glu Leu
            20                  25                  30

Arg Lys Glu Ala Cys Leu Leu Tyr Glu Ile Lys Trp Gly Met Ser Arg
        35                  40                  45

Lys Ile Trp Arg Ser Ser Gly Lys Asn Thr Thr Asn His Val Glu Val
    50                  55                  60

Asn Phe Ile Lys Lys Phe Thr Ser Glu Arg Asp Phe His Pro Ser Ile
65                  70                  75                  80

Ser Cys Ser Ile Thr Trp Phe Leu Ser Trp Ser Pro Cys Trp Glu Cys
                85                  90                  95

Ser Gln Ala Ile Arg Glu Phe Leu Ser Arg His Pro Gly Val Thr Leu
            100                 105                 110

Val Ile Tyr Val Ala Arg Leu Phe Trp His Met Asp Gln Gln Asn Arg
        115                 120                 125
```

```
Gln Gly Leu Arg Asp Leu Val Asn Ser Gly Val Thr Ile Gln Ile Met
    130                 135                 140

Arg Ala Ser Glu Tyr Tyr His Cys Trp Arg Asn Phe Val Asn Tyr Pro
145                 150                 155                 160

Pro Gly Asp Glu Ala His Trp Pro Gln Tyr Pro Pro Leu Trp Met Met
                165                 170                 175

Leu Tyr Ala Leu Glu Leu His Cys Ile Ile Leu Ser Leu Pro Pro Cys
                180                 185                 190

Leu Lys Ile Ser Arg Arg Trp Gln Asn His Leu Thr Phe Phe Arg Leu
            195                 200                 205

His Leu Gln Asn Cys His Tyr Gln Thr Ile Pro Pro His Ile Leu Leu
        210                 215                 220

Ala Thr Gly Leu Ile His Pro Ser Val Ala Trp Arg
225                 230                 235

<210> SEQ ID NO 2
<211> LENGTH: 863
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 2
gatcccagag gaggaagtcc agagacagag caccatgact tctgagaaag gagaagaatc      60
gaaccctggg agtttgacgt cttctatgac cccagagaac ttcgtaaaga ggcctgtctg     120
ctctacgaaa tcaagtgggg catgagccgg aagatctggc gaagctcagg caaaaacacc     180
accaatcacg tggaagttaa ttttataaaa aaatttacgt cagaaagaga ttttcaccca     240
tccatcagct gctccatcac ctggttcttg tcctggagtc cctgctggga atgctcccag     300
gctattagag agtttctgag tcggcaccct ggtgtgactc tagtgatcta cgtagctcgg     360
cttttttggc acatggatca acaaaatcgg caaggtctca gggaccttgt taacagtgga     420
gtaactattc agattatgag agcatcagag tattatcact gctggaggaa ttttgtcaac     480
tacccacctg gggatgaagc tcactggcca caatacccac ctctgtggat gatgttgtac     540
gcactggagc tgcactgcat aattctaagt cttccaccct gtttaaagat ttcaagaaga     600
tggcaaaatc atcttacatt tttcagactt catcttcaaa actgccatta ccaaacgatt     660
ccgccacaca tccttttagc tacagggctg atacatcctt ctgtggcttg agatgaata      720 ggatgattcc gtgtgtgtac tgattcaaga acaagcaatg atgacccact aaagagtgaa     780
tgccatttag aatctagaaa tgttcacaag gtaccccaaa actctgtagc ttaaaccaac     840
aataaatatg tattacctct ggc                                             863

<210> SEQ ID NO 3
<211> LENGTH: 424
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 3

Met Gly Pro Phe Cys Leu Gly Cys Ser His Arg Lys Cys Tyr Ser Pro
1               5                   10                  15

Ile Arg Asn Leu Ile Ser Gln Glu Thr Phe Lys Phe His Phe Lys Asn
            20                  25                  30

Leu Gly Tyr Ala Lys Gly Arg Lys Asp Thr Phe Leu Cys Tyr Glu Val
```

```
                35                  40                  45
Thr Arg Lys Asp Cys Asp Ser Pro Val Ser Leu His His Gly Val Phe
 50                  55                  60
Lys Asn Lys Asp Asn Ile His Ala Glu Ile Cys Phe Leu Tyr Trp Phe
 65                  70                  75                  80
His Asp Lys Val Leu Lys Val Leu Ser Pro Arg Glu Glu Phe Lys Ile
                 85                  90                  95
Thr Trp Tyr Met Ser Trp Ser Pro Cys Phe Glu Cys Ala Glu Gln Ile
                100                 105                 110
Val Arg Phe Leu Ala Thr His His Asn Leu Ser Leu Asp Ile Phe Ser
                115                 120                 125
Ser Arg Leu Tyr Asn Val Gln Asp Pro Glu Thr Gln Gln Asn Leu Cys
130                 135                 140
Arg Leu Val Gln Glu Gly Ala Gln Val Ala Ala Met Asp Leu Tyr Glu
145                 150                 155                 160
Phe Lys Lys Cys Trp Lys Lys Phe Val Asp Gly Gly Arg Arg Phe Arg
                165                 170                 175
Pro Trp Lys Arg Leu Leu Thr Asn Phe Arg Tyr Gln Asp Ser Lys Leu
                180                 185                 190
Gln Glu Ile Leu Arg Pro Cys Tyr Ile Pro Val Pro Ser Ser Ser Ser
                195                 200                 205
Ser Thr Leu Ser Asn Ile Cys Leu Thr Lys Gly Leu Pro Glu Thr Arg
210                 215                 220
Phe Cys Val Glu Gly Arg Met Asp Pro Leu Ser Glu Glu Phe Tyr
225                 230                 235                 240
Ser Gln Phe Tyr Asn Gln Arg Val Lys His Leu Cys Tyr Tyr His Arg
                245                 250                 255
Met Lys Pro Tyr Leu Cys Tyr Gln Leu Glu Gln Phe Asn Gly Gln Ala
                260                 265                 270
Pro Leu Lys Gly Cys Leu Leu Ser Glu Lys Gly Lys Gln His Ala Glu
                275                 280                 285
Leu Phe Leu Asp Lys Ile Arg Ser Met Glu Leu Ser Gln Val Thr Ile
290                 295                 300
Thr Cys Tyr Leu Thr Trp Ser Pro Cys Pro Asn Cys Ala Trp Gln Leu
305                 310                 315                 320
Ala Ala Phe Lys Arg Asp Arg Pro Asp Leu Ile Leu His Ile Tyr Thr
                325                 330                 335
Ser Arg Leu Tyr Phe His Trp Lys Arg Pro Phe Lys Gly Leu Cys Ser
                340                 345                 350
Leu Trp Gln Ser Gly Ile Leu Val Asp Val Met Asp Leu Pro Gln Phe
                355                 360                 365
Thr Asp Cys Trp Thr Asn Phe Val Asn Pro Lys Arg Pro Phe Trp Pro
370                 375                 380
Trp Lys Gly Leu Glu Ile Ile Ser Arg Arg Thr Gln Arg Arg Leu Arg
385                 390                 395                 400
Arg Ile Lys Glu Ser Trp Leu Gln Asp Leu Val Asn Asp Phe Gly Asn
                405                 410                 415
Leu Gln Leu Gly Pro Pro Met Ser
                420

<210> SEQ ID NO 4
<211> LENGTH: 9229
<212> TYPE: DNA
<213> ORGANISM: Artificial Sequence
<220> FEATURE:
```

<223> OTHER INFORMATION: Description of Artificial Sequence; note = synthetic construct

<400> SEQUENCE: 4

```
ggtctctctg gttagaccag atttgagcct gggagctctc tggctaacta gggaacccac      60
tgcttaagcc tcaataaagc ttgccttgag tgcttcaagt agtgtgtgcc cgtctgttgt     120
gtgactctgg taactagaga tccctcagac cctttagtc agtgtggaaa atctctagca      180
gtggcgcccg aacagggact tgaaagcgaa agggaaacca gaggagctct ctcgacgcag     240
gactcggctt gctgaagcgc gcacggcaag aggcgagggg aggcgactgg tgagtacgcc     300
aaaaattttg actagcggag gctagaagga gagagatggg tgcgagagcg tcagtattaa     360
gcggggagag aattagatcga tgggaaaaaa ttcggttaag gccaggggga agaaaaaat     420
ataaattaaa acatatagta tgggcaagca gggagctaga acgattcgca gttaatcctg     480
gcctgttaga acatcagaa ggctgtagac aaatactggg acagctacaa ccatcccttc      540
agacaggatc agaagaactt agatcattat ataatacagt agcaaccctc tattgtgtgc     600
atcaaaggat agagataaaa gacaccaagg aagctttaga caagatagag gaagagcaaa     660
acaaaagtaa gaaaaaagca cagcaagcag cagctgacac aggacacagc agccaggtca     720
gccaaaatta ccctatagtg cagaacatcc aggggcaaat ggtacatcag gccatatcac     780
ctagaacttt aaatgcatgg gtaaaagtag tagaagagaa ggctttcagc ccagaagtga     840
tacccatgtt ttcagcatta tcagaaggag ccaccccaca agatttaaac accatgctaa     900
acacagtggg gggacatcaa gcagccatgc aaatgttaaa agagaccatc aatgaggaag     960
ctgcagaatg ggatagagtg catccagtgc atgcagggcc tattgcacca ggccagatga    1020
gagaaccaag gggaagtgac atagcaggaa ctactagtac ccttcaggaa caaataggat    1080
ggatgacaaa taatccacct atcccagtag gagaaattta taaaagatgg ataatcctgg    1140
gattaaataa aatagtaaga atgtatagcc ctaccagcat tctggacata agacaaggac    1200
caaaagaacc ctttagagac tatgtagacc ggttctataa aactctaaga gccgagcaag    1260
cttcacagga ggtaaaaaat tggatgacag aaaccttgtt ggtccaaaat gcgaacccag    1320
attgtaagac tattttaaaa gcattgggac cagcagctac actagaagaa atgatgacag    1380
catgtcaggg agtgggagga cccggccata aggcaagagt tttggctgaa gcaatgagcc    1440
aagtaacaaa ttcagctacc ataatgatgc aaagaggcaa ttttaggaac caaagaaaga    1500
ttgttaagtg tttcaattgt ggcaagaag ggcacatagc cagaaattgc agggccccta    1560
ggaaaaaggg ctgttggaaa tgtggaaagg aaggacacca aatgaaagat tgtactgaga    1620
gacaggctaa ttttttaggg aagatctggc cttcctacaa gggaaggcca gggaattttc    1680
ttcagagcag accagagcca acagccccac catttcttca gagcagacca gagccaacag    1740
ccccaccaga gagagcttc aggtctgggg tagagacaac aactccctct cagaagcagg    1800
agccgataga caaggaactg tatccttttaa cttccctcag atcactcttt ggcaacgacc    1860
cctcgtcaca ataaagatag gggggcaact aaaggaagct ctattagata caggagcaga    1920
tgatacagta ttagaagaaa tgagtttgcc aggaagatgg aaaccaaaaa tgataggggg    1980
aattggaggt tttatcaaag taagacagta tgatcagata ctcatagaaa tctgtggaca    2040
taaagctata ggtacagtat tagtaggacc tacacctgtc aacataattg gaagaaatct    2100
gttgactcag attggttgca ctttaaattt tcccattagt cctattgaaa ctgtaccagt    2160
aaaattaaag ccaggaatgg atggcccaaa agttaaacaa tggccattga cagaagaaaa    2220
aataaaagca ttagtagaaa tttgtacaga atggaaaag gaagggaaaa tttcaaaaat    2280
```

```
tgggcctgaa aatccataca atactccagt atttgccata aagaaaaaag acagtactaa      2340
atggagaaaa ttagtagatt tcagagaact taataagaga actcaagact tctgggaagt      2400
tcaattagga ataccacatc ccgcagggtt aaaaagaaa aaatcagtaa cagtactgga       2460
tgtgggtgat gcatattttt cagttccctt agatgaagac ttcaggaagt atactgcatt      2520
taccatacct agtataaaca atgagacacc agggattaga tatcagtaca atgtgcttcc      2580
acagggatgg aaaggatcac cagcaatatt ccaaagtagc atgacaaaaa tcttagagcc      2640
ttttagaaaa caaaatccag acatagttat ctatcaatac atggatgatt tgtatgtagg      2700
atctgactta gaaatagggc agcatagaac aaaaatagag gagctgagac aacatctgtt      2760
gaggtgggga cttaccacac cagacaaaaa acatcagaaa gaacctccat tcctttggat      2820
gggttatgaa ctccatcctg ataaatggac agtacagcct atagtgctgc cagaaaaaga      2880
cagctggact gtcaatgaca tacagaagtt agtgggaaaa ttgaattggg caagtcagat      2940
ttacccaggg attaaagtaa ggcaattatg taaactcctt agaggaacca aagcactaac      3000
agaagtaata ccactaacag aagaagcaga gctagaactg gcagaaaaca gagagattct      3060
aaaagaacca gtacatggag tgtattatga cccatcaaaa gacttaatag cagaaataca      3120
gaagcagggg caaggccaat ggacatatca aatttatcaa gagccattta aaaatctgaa      3180
aacaggaaaa tatgcaagaa cgaggggtgc ccacactaat gatgtaaaac aattaacaga      3240
ggcagtgcaa aaaataacca cagaaagcat agtaatatgg ggaaagactc ctaaatttaa      3300
actacccata caaaaggaaa catgggaaac atggtggaca gagtattggc aagccacctg      3360
gattcctgag tgggagtttg tcaatacccc tcctttagtg aaattatggt accagttaga      3420
gaaagaaccc atagtaggag cagaaacgtt ctatgtagat ggggcagcta gcagggagac      3480
taaattagga aaagcaggat atgttactaa tagaggaaga caaaaagttg tcaccctaac      3540
tgacacaaca aatcagaaga ctgagttaca agcaattcat ctagctttgc aggattcggg      3600
attagaagta aatatagtaa cagactcaca atatgcatta ggaatcattc aagcacaacc      3660
agataaaagt gaatcagagt tagtcaatca aataatagag cagttaataa aaaaggaaaa      3720
ggtctatctg gcatgggtac cagcacacaa aggaattgga ggaaatgaac aagtagataa      3780
attagtcagt gctggaatca ggaaagtact atttttagat ggaatagata aggcccaaga      3840
tgaacatgag aaatatcaca gtaattggag agcaatggct agtgatttta acctgccacc      3900
tgtagtagca aaagaaatag tagccagctg tgataaatgt cagctaaaag gagaagccat      3960
gcatggacaa gtagactgta gtccaggaat atggcaacta gattgtacac atttagaagg      4020
aaaagttatc ctggtagcag ttcatgtagc cagtggatat atagaagcag aagttattcc      4080
agcagaaaca gggcaggaaa cagcatactt tcttttaaaa ttagcaggaa gatggccagt      4140
aaaaacaata catacagaca atggcagcaa tttcaccagt actacggtta aggccgcctg      4200
ttggtgggcg ggaatcaagc aggaatttgg aattccctac aatccccaaa gtcaaggagt      4260
agtagaatct atgaataaag aattaaagaa aattataggc caggtaagag atcaggctga      4320
acatcttaag acagcagtac aaatggcagt attcatccac aattttaaaa gaaaaggggg      4380
gattgggggg tacagtgcag gggaaagaat agtagacata atagcaacag acatacaaac      4440
taaagaatta caaaaacaaa ttacaaaaat tcaaaatttt cgggtttatt acagggacag      4500
cagagatcca ctttggaaag gaccagcaaa gctcctctgg aaaggtgaag ggcagtagt       4560 aatacaagat aatagtgaca taaaagtagt gccaagaaga aaagcaaaga tcattaggga      4620
ttatggaaaa cagatggcag gtgatgattg tgtggcaagt agacaggatg aggattagaa      4680
```

```
catggaaaag tttagtaaaa caccatatgt atgtttcagg gaaagctagg ggatggtttt      4740
atagacatca ctatgaaagc cctcatccaa gaataagttc agaagtacac atcccactag      4800
gggatgctag attggtaata acaacatatt ggggtctgca tacaggagaa agagactggc      4860
atctgggtca gggagtctcc atagaatgga ggaaaaagag atatagcaca caagtagacc      4920
ctgaactagc agaccaacta attcatctgt attactttga ctgttttttca gactctgcta      4980 taagaaaggc cttattagga catatagtta gccctaggtg tgaatatcaa gcaggacata      5040
acaaggtagg atctctacaa tacttggcac tagcagcatt aataacacca aaaaagataa      5100
agccaccttt gcctagtgtt acgaaactga cagaggatag atggaacaag ccccagaaga      5160
ccaagggcca cagagggagc cacacaatga atggacacta gagcttttag aggagcttaa      5220
gaatgaagct gttagacatt ttcctaggat ttggctccat ggcttagggc aacatatcta      5280
tgaaacttat ggggatactt gggcaggagt ggaagccata ataagaattc tgcaacaact      5340
gctgtttatc catttcagaa ttgggtgtcg acatagcaga ataggcgtta ctcaacagag      5400
gagagcaaga aatggagcca gtagatccta gactagagcc ctggaagcat ccaggaagtc      5460
agcctaaaac tgcttgtacc acttgctatt gtaaaagtg ttgctttcat gccaagttt        5520 gtttcacaac aaaagcctta ggcatctcct atggcaggaa gaagcggaga cagcgacgaa      5580
gacctcctca aggcagtcag actcatcaag tttctctatc aaagcagtaa gtagtacatg      5640
taatgcaacc tatacaaata gcaatagcag cattagtagt agcaataata atagcaatag      5700
ttgtgtggtc catagtaatc atagaatata ggaaaatatt aagacaaaga aaaatagaca      5760
ggttaattga tagactaata gaaagagcag aagacagtgg caatgagagt gaaggagaaa      5820
tatcagcact tgtggagatg ggggtggaaa tggggcacca tgctccttgg gatattgatg      5880
atctgtagtg ctacagaaaa attgtgggtc acagtctatt atggggtacc tgtgtggaag      5940
gaagcaacca ccactctatt ttgtgcatca gatgctaaag catatgatac agaggtacat      6000
aatgtttggg ccacacatgc ctgtgtaccc acagacccca acccacaaga agtagtattg      6060
gtaaatgtga cagaaaattt taacatgtgg aaaaatgaca tggtagaaca gatgcatgag      6120
gatataatca gtttatggga tcaaagccta aagccatgtg taaaattaac cccactctgt      6180
gttagtttaa agtgcactga tttggggaat gctactaata ccaatagtag taataccaat      6240
agtagtagcg gggaaatgat gatggagaaa ggagagataa aaaactgctc tttcaatatc      6300
agcacaagca taagaggtaa ggtgcagaaa gaatatgcat ttttttataa acttgatata      6360
ataccaatag ataatgatac taccagctat acgttgacaa gttgtaacac ctcagtcatt      6420
acacaggcct gtccaaaggt atcctttgag ccaattccca tacattattg tgccccggct      6480
ggttttgcga ttctaaaatg taataataag acgttcaatg gaacaggacc atgtacaaat      6540
gtcagcacag tacaatgtac acatggaatt aggccagtag tatcaactca actgctgttg      6600
aatggcagtc tagcagaaga gaggtagta attagatctg ccaatttcac agacaatgct      6660
aaaaccataa tagtacagct gaaccaatct gtagaaatta ttgtacaag acccaacaac      6720 aatacaagaa aaagtatccg tatccagagg ggaccaggga gagcatttgt tacaatagga      6780
aaaataggaa atatgagaca agcacattgt aacattagta gagcaaaatg gaatgccact      6840
ttaaaacaga tagctagcaa attaagagaa caatttggaa ataataaaac aataatcttt      6900
aagcaatcct caggagggga cccagaaatt gtaacgcaca gttttaattg tggaggggaa      6960 ttttttctact gtaattcaac acaactgttt aatagtactt ggtttaatag tacttggagt      7020
actgaagggt caaataacac tgaaggaagt gacacaatca cactcccatg cagaataaaa      7080
```

```
caatttataa acatgtggca ggaagtagga aaagcaatgt atgcccctcc catcagcgga    7140
caaattagat gttcatcaaa tattacaggg ctgctattaa caagagatgg tggtaataac    7200
aacaatgggt ccgagatctt cagacctgga ggaggagata tgagggacaa ttggagaagt    7260
gaattatata aatataaagt agtaaaaatt gaaccattag gagtagcacc caccaaggca    7320
aagagaagag tggtgcagag agaaaaaaga gcagtgggaa taggagcttt gttccttggg    7380
ttcttgggag cagcaggaag cactatgggc gcacggtcaa tgacgctgac ggtacaggcc    7440
agacaattat tgtctggtat agtgcagcag cagaacaatt tgctgagggc tattgaggcg    7500
caacagcatc tgttgcaact cacagtctgg ggcatcaagc agctccaggc aagaatcctg    7560
gctgtggaaa gatacctaaa ggatcaacag ctcctgggga tttggggttg ctctggaaaa    7620
ctcatttgca ccactgctgt gccttggaat gctagttgga gtaataaatc tctggaacag    7680
atttggaata acatgacctg gatggagtgg gacagagaaa ttaacaatta cacaagctta    7740
atacattcct taattgaaga atcgcaaaac cagcaagaaa agaatgaaca agaattattg    7800
gaattagata aatgggcaag tttgtggaat tggtttaaca taacaaattg gctgtggtat    7860
ataaaaatat tcataatgat agtaggaggc ttggtaggtt taagaatagt ttttgctgta    7920
ctttctatag tgaatagagt taggcaggga tattcaccat tatcgtttca gacccacctc    7980
ccaaccccga gggacccga caggcccgaa ggaatagaag aagaaggtgg agagagagac    8040
agagacagat ccattcgatt agtgaacgga tccttagcac ttatctggga cgatctgcgg    8100
agcctgtgcc tcttcagcta ccaccgcttg agagacttac tcttgattgt aacgaggatt    8160
gtggaacttc tgggacgcag ggggtgggaa gccctcaaat attggtggaa tctcctacag    8220
tattggagtc aggaactaaa gaatagtgct gttagcttgc tcaatgccac agccatagca    8280
gtagctgagg ggacagatag ggttatagaa gtagtacaag gagcttgtag agctattcgc    8340
cacataccta gaagaataag acagggcttg gaaaggattt tgctataaga tgggtggcaa    8400
gtggtcaaaa agtagtgtgg ttggatggcc tactgtaagg gaaagaatga gacgagctga    8460
gccagcagca gatggggtgg gagcagcatc tcgagacctg gaaaaacatg gagcaatcac    8520
aagtagcaat acagcagcta ccaatgctgc ttgtgcctgg ctagaagcac aagaggagga    8580
ggaggtgggt tttccagtca cacctcaggt acctttaaga ccaatgactt acaaggcagc    8640
tgtagatctt agccactttt taaaagaaaa gggggggactg gaagggctaa ttcactccca    8700
acgaagacaa gatatccttg atctgtggat ctaccacaca caaggctact ccctgattg     8760 gcagaactac acaccagggc cagggtcag atatccactg acctttggat ggtgctacaa    8820
gctagtacca gttgagccag ataaggtaga agaggccaat aaaggagaga acaccagctt    8880
gttacaccct gtgagcctgc atggaatgga tgaccctgag agagaagtgt tagagtggag    8940
gtttgacagc cgcctagcat ttcatcacgt ggcccgagag ctgcatccgg agtacttcaa    9000
gaactgctga catcgagctt gctacaaggg actttccgct ggggactttc cagggaggcg    9060
tggcctgggc gggactgggg agtggcgagc cctcagatgc tgcatataag cagctgcttt    9120
ttgcctgtac tgggtctctc tggttagacc agatttgagc ctgggagctc tctggctaac    9180
tagggaaccc actgcttaag cctcaataaa gcttgccttg agtgcttca                9229
```

<210> SEQ ID NO 5
<211> LENGTH: 198
<212> TYPE: PRT
<213> ORGANISM: Artificial Sequence
<220> FEATURE:
<223> OTHER INFORMATION: Description of Artificial Sequence; note = synthetic construct

<400> SEQUENCE: 5

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 6
<211> LENGTH: 597
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 6
atggacagcc tcttgatgaa ccggaggaag tttctttacc aattcaaaaa tgtccgctgg      60
gctaagggtc ggcgtgagac ctacctgtgc tacgtagtga agaggcgtga cagtgctaca     120
tccttttcac tggactttgg ttatcttcgc aataagaacg gctgccacgt ggaattgctc     180
ttcctccgct acatctcgga ctgggaccta gaccctggcc gctgctaccg cgtcacctgg     240
ttcacctcct ggagcccctg ctacgactgt gcccgacatg tggccgactt tctgcgaggg     300
aaccccaacc tcagtctgag gatcttcacc gcgcgcctct acttctgtga ggaccgcaag     360
gctgagcccg aggggctgcg gcggctgcac cgcgccgggg tgcaaatagc catcatgacc     420
ttcaaagatt attttttactg ctggaatact tttgtagaaa accatgaaag aactttcaaa     480
gcctgggaag gctgcatga aaattcagtt cgtctctcca gacagcttcg gcgcatcctt     540
ttgcccctgt atgaggttga tgacttacga gacgcatttc gtactttggg actttga        597

<210> SEQ ID NO 7
<211> LENGTH: 4
<212> TYPE: PRT
<213> ORGANISM: Artificial Sequence
<220> FEATURE:

<223> OTHER INFORMATION: Description of Artificial Sequence; note = synthetic construct

<400> SEQUENCE: 7

Trp Arg Glx Tyr
 1

<210> SEQ ID NO 8
<211> LENGTH: 1770
<212> TYPE: DNA
<213> ORGANISM: Artificial Sequence
<220> FEATURE:
<223> OTHER INFORMATION: Description of Artificial Sequence; note = synthetic construct

<400> SEQUENCE: 8

| | | |
|---|---|---|
| ctcaatggaa tcaaatcaca aatccgggga tggattgagc ggcactcaga aggaagcagc | 60 |
| cctccgcgca ctggtccagc gcacaggata tagcttggtc caggaaaatg acaaagaaa | 120 |
| atatggtggc cctccacctg gttgggatgc tgcacccct gaaagggggct gtgaaatttt | 180 |
| tattggaaaa cttccccgag accttttga ggatgagctt ataccattat gtgaaaaat | 240 |
| cggtaaaatt tatgaaatga gaatgatgat ggatttaat ggcaacaata gaggatatgc | 300 |
| atttgtaaca ttttcaaata aagtggaagc caagaatgca atcaagcaac ttaataatta | 360 |
| tgaaattaga aatgggcgcc tcttaggggt ttgtgccagt gtggacaact gccgattatt | 420 |
| tgttggggc atcccaaaaa ccaaaaagag agaagaatc ttatcggaga tgaaaaggt | 480 |
| tactgaaggt gttgtcgatg tcatcgtcta cccaagcgct gcagataaaa ccaaaaaccg | 540 |
| aggctttgcc ttcgtggagt atgagagtca tcgagcagct gccatggcga ggaggaaact | 600 |
| gctaccagga agaattcagt tatggggaca tggtattgca gtagactggg cagagccaga | 660 |
| agtagaagtt gatgaagata caatgtcttc agtgaaaatc ctatatgtaa gaaatcttat | 720 |
| gctgtctacc tctgaagaga tgattgaaaa ggaattcaac aatatcaaac caggtgctgt | 780 |
| ggagagggtg aagaaaattc gagactatgc ttttgtgcac ttcagtaacc gagaagatgc | 840 |
| agttgaggct atgaaagctt taatggcaa ggtgctggat ggttccccca ttgaagtcac | 900 |
| cctagcaaaa ccagtggaca aggacagtta tgttaggtat acccgaggca caggtggaag | 960 |
| gggcaccatg ctgcaaggag agtataccta ctctttgggc caagtttatg atcccaccac | 1020 |
| aacctacctt ggagctcctg tcttctatgc ccccagacc tatgcagcaa ttcccagtct | 1080 |
| tcatttccca gccaccaaag acatctcag caacagagcc attatccgag ccccttctgt | 1140 |
| tagaggggct gcgggagtga gaggactggg cggccgtggc tatttggcat acacaggcct | 1200 |
| gggtcgagga taccaggtca aaggagacaa aagagaagac aaactctatg acattttacc | 1260 |
| tgggatggag ctcacccaa tgaatcctgt cacattaaaa ccccaaggaa ttaaactcgc | 1320 |
| tccccagata ttagaagaga tttgtcaaa aaataactgg ggacagccag tgtaccagct | 1380 |
| gcactctgct attggacaag accaaagaca gctattcttg tacaaaataa ctattcctgc | 1440 |
| tctagccagc cagaatcctg caatccaccc tttcacacct ccaaagctga gtgcctttgt | 1500 |
| ggatgaagca aagacgtatg cagccgaata caccctgcag accctgggca tccccactga | 1560 |
| tggaggcgat ggcaccatgg ctactgctgc tgctgctgct actgctttcc caggatatgc | 1620 |
| tgtccctaat gcaactgcac ccgtgtctgc agcccagctc aagcaagcgg taaccccttgg | 1680 |
| acaagactta gcagcatata caacctatga ggtctaccca acttttgcag tgactgcccg | 1740 |
| agggatgga tatggcacct tctgaagatg | 1770 |

<210> SEQ ID NO 9
<211> LENGTH: 1717
<212> TYPE: DNA
<213> ORGANISM: Artificial Sequence
<220> FEATURE:
<223> OTHER INFORMATION: Description of Artificial Sequence; note = synthetic construct

<400> SEQUENCE: 9

```
ctgccagggg gagggcccca gagaaaacca gaaagagggt gagagactga ggaagataaa     60
gcgtcccagg gcctcctaca ccagcgcctg agcaggaagc gggaggggcc atgactacga    120
ggccctggga ggtcactttta gggagggctg tcctaaaacc agaagcttgg agcagaaagt    180
gaaaccctgg tgctccagac aaagatctta gtcgggacta gccggccaag gatgaagcct    240
cacttcagaa acacagtgga gcgaatgtat cgagacacat tctcctacaa ctttttataat    300
agacccatcc tttctcgtcg gaataccgtc tggctgtgct acgaagtgaa acaaagggt    360
ccctcaaggc cccctttgga cgcaaagatc tttcgaggcc aggtgtattc cgaacttaag    420
taccacccag agatgagatt cttccactgg ttcagcaagt ggaggaagct gcatcgtgac    480
caggagtatg aggtcacctg gtacatatcc tggagcccct gcacaaagtg tacaagggat    540
atggccacgt tcctggccga ggacccgaag gttaccctga ccatcttcgt tgcccgcctc    600
tactacttct gggacccaga ttaccaggag gcgcttcgca gcctgtgtca gaaaagagac    660
ggtccgcgtg ccaccatgaa gatcatgaat tatgacgaat tcagcactg ttggagcaag    720
ttcgtgtaca gccaaagaga gctatttgag ccttggaata tctgcctaa atattatata    780
ttactgcaca tcatgctggg ggagattctc agacactcga tggatccacc cacattcact    840
ttcaactttta acaatgaacc ttgggtcaga ggacggcatg agacttacct gtgttatgag    900
gtggagcgca tgcacaatga cacctgggtc ctgctgaacc agcgcagggg ctttctatgc    960
aaccaggctc cacataaaca cggtttcctt gaaggccgcc atgcagagct gtgcttcctg   1020
gacgtgattc ccttttggaa gctggacctg accaggact acagggttac ctgcttcacc   1080
tcctggagcc cctgcttcag ctgtgcccag gaaatggcta aattcatttc aaaaaacaaa   1140
cacgtgagcc tgtgcatctt cactgcccgc atctatgatg atcaaggaag atgtcaggag   1200
gggctgcgca ccctggccga ggctggggcc aaaatttcaa taatgacata cagtgaattt   1260
aagcactgct gggacacctt tgtggaccac caggatgtc ccttccagcc tgggatgga   1320
ctagatgagc acagccaaga cctgagtggg aggctgcggg ccattctcca gaatcaggaa   1380
aactgaagga tgggcctcag tctctaagga aggcagagac ctgggttgag cctcagaata   1440
aaagatcttc ttccaagaaa tgcaaacagg ctgttcacca ccatctccag ctgatcacag   1500
acaccagcaa agcaatgcac tcctgaccaa gtagattctt ttaaaaatta gagtgcatta   1560
ctttgaatca aaatttatt tatatttcaa gaataaagta ctaagattgt gctcaataca   1620
cagaaaagtt tcaaacctac taatccagcg acaatttgaa tcggttttgt aggtagagga   1680
ataaaatgaa atactaaatc tttctgtaaa aaaaaaa                            1717
```

<210> SEQ ID NO 10
<211> LENGTH: 384
<212> TYPE: PRT
<213> ORGANISM: Artificial Sequence
<220> FEATURE:
<223> OTHER INFORMATION: Description of Artificial Sequence; note = synthetic construct

<400> SEQUENCE: 10

Met Lys Pro His Phe Arg Asn Thr Val Glu Arg Met Tyr Arg Asp Thr

```
                1               5                  10                 15
            Phe Ser Tyr Asn Phe Tyr Asn Arg Pro Ile Leu Ser Arg Arg Asn Thr
                            20                  25                  30

Val Trp Leu Cys Tyr Glu Val Lys Thr Lys Gly Pro Ser Arg Pro Pro
                            35                  40                  45

Leu Asp Ala Lys Ile Phe Arg Gly Gln Val Tyr Ser Glu Leu Lys Tyr
                50                  55                  60

His Pro Glu Met Arg Phe His Trp Phe Ser Lys Trp Arg Lys Leu
            65                  70                  75                  80

His Arg Asp Gln Glu Tyr Glu Val Thr Trp Tyr Ile Ser Trp Ser Pro
                            85                  90                  95

Cys Thr Lys Cys Thr Arg Asp Met Ala Thr Phe Leu Ala Glu Asp Pro
                            100                 105                 110

Lys Val Thr Leu Thr Ile Phe Val Ala Arg Leu Tyr Tyr Phe Trp Asp
                            115                 120                 125

Pro Asp Tyr Gln Glu Ala Leu Arg Ser Leu Cys Gln Lys Arg Asp Gly
                130                 135                 140

Pro Arg Ala Thr Met Lys Ile Met Asn Tyr Asp Glu Phe Gln His Cys
            145                 150                 155                 160

Trp Ser Lys Phe Val Tyr Ser Gln Arg Glu Leu Phe Glu Pro Trp Asn
                            165                 170                 175

Asn Leu Pro Lys Tyr Tyr Ile Leu Leu His Ile Met Leu Gly Glu Ile
                            180                 185                 190

Leu Arg His Ser Met Asp Pro Pro Thr Phe Thr Phe Asn Phe Asn Asn
                            195                 200                 205

Glu Pro Trp Val Arg Gly Arg His Glu Thr Tyr Leu Cys Tyr Glu Val
                210                 215                 220

Glu Arg Met His Asn Asp Thr Trp Val Leu Leu Asn Gln Arg Arg Gly
            225                 230                 235                 240

Phe Leu Cys Asn Gln Ala Pro His Lys His Gly Phe Leu Glu Gly Arg
                            245                 250                 255

His Ala Glu Leu Cys Phe Leu Asp Val Ile Pro Phe Trp Lys Leu Asp
                            260                 265                 270

Leu Asp Gln Asp Tyr Arg Val Thr Cys Phe Thr Ser Trp Ser Pro Cys
                            275                 280                 285

Phe Ser Cys Ala Gln Glu Met Ala Lys Phe Ile Ser Lys Asn Lys His
                290                 295                 300

Val Ser Leu Cys Ile Phe Thr Ala Arg Ile Tyr Asp Asp Gln Gly Arg
            305                 310                 315                 320

Cys Gln Glu Gly Leu Arg Thr Leu Ala Glu Ala Gly Ala Lys Ile Ser
                            325                 330                 335

Ile Met Thr Tyr Ser Glu Phe Lys His Cys Trp Asp Thr Phe Val Asp
                            340                 345                 350

His Gln Gly Cys Pro Phe Gln Pro Trp Asp Gly Leu Asp Glu His Ser
                            355                 360                 365

Gln Asp Leu Ser Gly Arg Leu Arg Ala Ile Leu Gln Asn Gln Glu Asn
                370                 375                 380

<210> SEQ ID NO 11
<211> LENGTH: 8
<212> TYPE: RNA
<213> ORGANISM: Artificial Sequence
<220> FEATURE:
<223> OTHER INFORMATION: Description of Artificial Sequence; note =
      synthetic construct
<220> FEATURE:
```

```
<221> NAME/KEY: misc_feature
<222> LOCATION: 4
<223> OTHER INFORMATION: n can be a or u
<220> FEATURE:
<221> NAME/KEY: misc_feature
<222> LOCATION: 6
<223> OTHER INFORMATION: n can be a, g, c, or t(u)

<400> SEQUENCE: 11 uuununuu                                                                    8

<210> SEQ ID NO 12
<211> LENGTH: 18
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 12 caauugauc aguauauu                                                         18

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence; note =
      synthetic construct
<220> FEATURE:
<221> NAME/KEY: misc_feature
<222> LOCATION: 5
<223> OTHER INFORMATION: n can be a g, c, or t(u)

<400> SEQUENCE: 13
gauanaauuu gaucaguaua u                                                    21

<210> SEQ ID NO 14
<211> LENGTH: 31
<212> TYPE: RNA
<213> ORGANISM: Artificial Sequence
<220> FEATURE:
<223> OTHER INFORMATION: Description of Artificial Sequence; note =
      synthetic construct
<220> FEATURE:
<221> NAME/KEY: misc_feature
<222> LOCATION: 10
<223> OTHER INFORMATION: n can be a, g, c or t(u)

<400> SEQUENCE: 14
ccuuuauuan gaauugugau cacauccucu g                                         31

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence; note =
      synthetic construct
<220> FEATURE:
<221> NAME/KEY: misc_feature
<222> LOCATION: 10
<223> OTHER INFORMATION: n can be a, g, c or t(u)

<400> SEQUENCE: 15
aagcaagttn tttgatcagt ttactcaaac a                                         31

<210> SEQ ID NO 16
<211> LENGTH: 31
<212> TYPE: DNA
```

```
<213> ORGANISM: Artificial Sequence
<220> FEATURE:
<223> OTHER INFORMATION: Description of Artificial Sequence; note =
      synthetic construct
<220> FEATURE:
<221> NAME/KEY: misc_feature
<222> LOCATION: 10
<223> OTHER INFORMATION: n can be a, g, c or t(u)

<400> SEQUENCE: 16
aaatgctgcn agaaattgat cagaataagg a                                31

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence; note =
      synthetic construct
<220> FEATURE:
<221> NAME/KEY: misc_feature
<222> LOCATION: 10
<223> OTHER INFORMATION: n can be a, g, c or t(u)

<400> SEQUENCE: 17
ttacttgcan caaactgatc agttttgaga g                                31

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence; note =
      synthetic construct
<220> FEATURE:
<221> NAME/KEY: misc_feature
<222> LOCATION: 10
<223> OTHER INFORMATION: n can be a, g, c or t(u)

<400> SEQUENCE: 18
aggtacgttn tggatgatca gtacacaagt tc                               32

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 19

Trp Arg Cys Tyr
 1

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 1, 2, 7, 8
<223> OTHER INFORMATION: Xaa = any amino acid

<400> SEQUENCE: 20

Xaa Xaa Trp Arg Glx Tyr Xaa Xaa
 1               5
```

```
<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 5, 8, 14
<223> OTHER INFORMATION: Xaa = any amino acid

<400> SEQUENCE: 21

Arg Gly Thr Trp Xaa Trp Arg Xaa Tyr Arg Gly Thr Trp Xaa
 1               5                   10

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence; note =
      synthetic construct
<220> FEATURE:
<221> NAME/KEY: misc_feature
<222> LOCATION: 1, 8
<223> OTHER INFORMATION: n can be a, g, c, or t(u)

<400> SEQUENCE: 22
nagctagnta agttat                                                    16
```